US007598289B2

(12) United States Patent
Ralston et al.

(10) Patent No.: US 7,598,289 B2
(45) Date of Patent: Oct. 6, 2009

(54) KETONES AND REDUCED KETONES AS THERAPEUTIC AGENTS FOR THE TREATMENT OF BONE CONDITIONS

(75) Inventors: Stuart H. Ralston, Edinburgh (GB); Iain R. Greig, Aberdeen (GB); Aymen I. I. Mohamed, Edinburgh (GB); Robert J. Van 'T Hof, Edinburgh (GB)

(73) Assignee: The University Court of the University of Aberdeen, Aberdeen (GB)

( * ) Notice: Subject to any disclaimer, the term of this patent is extended or adjusted under 35 U.S.C. 154(b) by 0 days.

(21) Appl. No.: 12/193,855

(22) Filed: Aug. 19, 2008

(65) Prior Publication Data

US 2008/0312186 A1 Dec. 18, 2008

Related U.S. Application Data

(62) Division of application No. 10/555,738, filed as application No. PCT/GB2004/001958 on May 6, 2004.

(30) Foreign Application Priority Data

May 7, 2003 (GB) .................................. 0310463.5
Oct. 29, 2003 (GB) .................................. 0325259.0

(51) Int. Cl.
*A61K 31/185* (2006.01)
*A61K 31/22* (2006.01)
*A61K 31/15* (2006.01)
*A61K 31/12* (2006.01)
*C07C 49/00* (2006.01)
*C07C 207/00* (2006.01)

(52) U.S. Cl. .................. 514/436; 514/546; 514/640; 514/679; 568/303; 568/306; 568/335; 568/336

(58) Field of Classification Search ................ 514/436, 514/546, 640, 679; 568/303, 306, 335, 336
See application file for complete search history.

(56) References Cited

U.S. PATENT DOCUMENTS

| 4,017,416 | A | 4/1977 | Inukai et al. |
| 5,859,047 | A | 1/1999 | Kluender et al. |
| 2005/0119305 | A1 | 6/2005 | Naka et al. |

FOREIGN PATENT DOCUMENTS

| EP | 1 215 203 | 6/2002 |
| JP | 11-80107 | 3/1999 |
| JP | 2001-352978 A | 12/2001 |
| WO | WO 97/10247 | 3/1997 |
| WO | WO 97/41099 | 11/1997 |
| WO | WO 02/074298 | 9/2002 |
| WO | WO 02/092588 | 11/2002 |
| WO | WO 03/037321 | 5/2003 |

OTHER PUBLICATIONS

Baud, V. et al, 1999, "Signaling by proinflammatory cytokines: oligomerization of TRAF2 and TRAF6 is sufficient for JNK and IKK activation and target gene induction via an amino-terminal effector domain", *Genes Dev.*, vol. 13, pp. 1297-1308.

Brennan, F.M. et al, 1989, "Inhibitory effect of TNF alpha antibodies on synovial cell interleukin-1 production in rheumatoid arthritis", *Lancet*, vol. 334, pp. 244-247.

Brennan, F.M. et al, 1996, "Cytokines in autoimmunity", *Curr. Opin. Immunol.*, vol. 8, pp. 872-877.

Brennan, F.M. et al, 1992, "Enhanced expression of tumor necrosis factor receptor mRNA and protein in mononuclear cells isolated from rheumatoid arthritis synovial joints", *Eur. J. Immunol.*, vol. 22, pp. 1907-1912.

Corey, E.J. et al, 1988, "An efficient and catalytically enantioselective route to (S)-(-)-Phenyloxirane," *J. Org. Chem.*, vol. 53, pp. 2861-2863.

Elliott, M.J. et al, 1994, "Randomised double-blind comparison of chimeric monoclonal antibody to tumour necrosis factor alpha (cA2) versus placebo in rheumatoid arthritis", *Lancet*, vol. 344, pp. 1105-1110.

Feldmann, M. et al, 1994, "TNF alpha as a therapeutic target in rheumatoid arthritis," *Circ. Shock*, vol. 43, pp. 179-184.

Feldmann, M. et al, 2001, "The role of TNF alpha and IL-1 in rheumatoid arthritis," *Curr. Dir. Autoimmun.*, vol. 3, pp. 188-199.

Feldmann, M. et al, 1996, "Rheumatoid arthritis", *Cell*, vol. 85, pp. 307-310.

Firestein, G.S. et al, 1996, "Invasive fibroblast-like synoviocytes in rheumatoid arthtitis. Passive responders or transformed aggressors?", *Arthritis Rheum.*, vol. 39, pp. 1781-1790.

Firestein, G.S. et al, 2005, "Immunologic mechanisms in the pathogenesis of rheumatoid arthritis", *J. Clin. Rheumatol.*, vol. 11. pp. S39-S44.

(Continued)

*Primary Examiner*—Raymond J Henley, III
(74) *Attorney, Agent, or Firm*—Nixon & Vanderhye P.C.

(57) ABSTRACT

The present invention pertains to certain ketones and reduced ketones and derivatives thereof which, inter alia, inhibit osteoclast survival, formation, and/or activity; and/or inhibit bone resorption, and more particularly to compounds of the formulae and pharmaceutically acceptable salts, amides, esters, and ethers thereof, wherein: Ar1, $R^{alk}$, —ORO, and -Q are as defined herein:

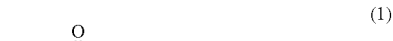

(1)

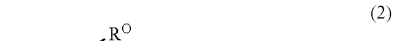

(2)

The present invention also pertains to pharmaceutical compositions comprising such compounds. The compounds inhibit osteoclast survival, formation, and/or activity, and inhibit conditions mediated by osteoclasts and/or characterised by bone resorption, and are useful in the treatment of bone disorders such as osteoporosis, rheumatoid arthritis, cancer associated bone disease, Paget's disease, aseptic loosening of prosthetic implants, and the like; and/or in the treatment of conditions associated with inflammation or activation of the immune system.

52 Claims, 3 Drawing Sheets

OTHER PUBLICATIONS

Firestein, G.S. et al, 1999, "Signal transduction and transcription factors in rheumatic disease", *Arthritis Rheum.*, vol. 42, pp. 609-621.
Gottlieb, A.B., 2005, "Psoriasis: Emerging Therapeutic Strategies", *Nat. Rev. Drug Disc.*, vol. 4, pp. 19-34.
"Chapter 4: Protection for the Carbonyl Group", pp. 293-368 in *Protective Groups in Organic Synthesis*, Third Edition (Green, T.W. and Wuts, P.G.M., editors) (John Wiley & Sons, Inc., 1999).
Jimi, E. et al, 2004, "Selective inhibition of NF-kappa B blocks osteoclastogenesis and prevents inflammatory bone destruction in vivo", *Nat. Med.*, vol. 10, pp. 617-624.
Joosten, L.A. et al, 1996, "Anticytokine treatment of established type II collagen-induced arthritis in DBA/1 mice. A comparative study using anti-TNF alpha, anti-IL-1 alpha/beta, and IL-1Ra," *Arthritis Rheum.*, vol. 39, pp. 797-809.
Klareskog, L. et al, 2006, "A long-term, open-label trial of the safety and efficacy of etanercept (Enbrel) in patients with rheumatoid arthritis not treated with other disease-modifying antirheumatic drugs", *Ann. Rheum. Dis.*, vol. 65, pp. 1578-1584.
Klareskog, L. et al, 2006, "Mechanisms of disease: Genetic susceptibility and environmental triggers in the development of rheumatoid arthritis," *Nat. Clin. Pract. Rheumatol.*, vol. 2, pp. 425-433.
Korzenik, J.R. et al, 2006, "Evolving knowledge and therapy of inflammatory bowel disease," *Nat. Rev. Drug Disc.*, vol. 5, pp. 197-209.
Liu, Z.G., 2005, "Molecular mechanism of TNF signaling and beyond," *Cell Res.*, vol. 15, pp. 24-27.
McInnes, I.B. et al, 2005, "Targeting cytokines beyond tumor necrosis factor-alpha and interleukin-1 in rheumatoid arthritis", *Curr. Pain Headache Rep.*, vol. 9, pp. 405-411.
Mount, C. et al, 2005, "Rheumatoid arthritis market", *Nat. Rev. Drug Disc.*, vol. 4, pp. 11-12.
Ramachandran, P.V. et al, 1995, "Chiral synthesis via organoboranes. 40. Selective reductions. 55. A simple on-pot synthesis of the enantiomers of (trifluoromethyl)oxirane. A general synthesis in high optical purities of alpha trifluoromethyl secondary alcohols via the ring-cleavage reactions of the epoxide", *J. Org. Chem.*, vol. 60, pp. 41-46.
Roodman, G.D., 2006, "Regulation of osteoclast differentiation", *Ann. N. Y. Acad. Sci.*, vol. 1068, pp. 100-109.
Smolen, J.S. et al, 2003, "Therapeutic Strategies for Rheumatoid Arthritis", *Nat. Rev. Drug Disc.*, vol. 2, pp. 473-488.
Tanaka, S. et al, 2003, "Signal transduction pathways regulating osteoclast differentiation and function," *J. Bone Miner. Metab.*, vol. 21, pp. 123-133.
Ueno, K., et al., 1969, "A new synthesis of Vitamin $B_6$ group", *Tetrahedron Letters*, No. 16, pp. 1283-1286.
van den Berg, W.B., 2002, "Is there a rationale for combined TNF and IL-1 blocking in arthritis?", *Clin. Exp. Rheumatol.*, vol. 20, pp. S21-S25.
van den Berg, W.B. et al, 1999, "Pathogenesis of joint damage in rheumatoid arthritis: evidence of a dominant role for interleukin-I", *Baillieres Best Pract. Res. Clin. Rheumatol.*, vol. 13, pp. 577-597.
Weissmann, G., 2006, "The pathogenesis of rheumatoid arthritis," *Bull. Hosp. Jt. Dis.*, vol. 64, pp. 12-15.
Ziff, M., 1990, "Rheumatoid arthritis—it's present and future", *J. Rheumatol.*, vol. 17, pp. 127-133.
Armour K.J., et al., 2001, "Inhibition of bone resorption in vitro and prevention of ovariectomy-induced bone loss in vivo by flurbiprofen nitroxybutylester (HCT1026)," *Arthritis and Rheumatism*, vol. 44, No. 9, pp. 2185-2192.
Boots, M.R., et al., 1973, "Hypocholesterolemic Agents II: Inhibition of β-Hydroxy-β-Methylglutaryl Coenzyme A Reductase by Arylalkyl Hydrogen Succinates and Glutarates", *J. Pharm. Sci.*, vol. 62, No. 6, pp. 952-957.
Boots, M.R., et al, 1976, "Hypocholesterolemic Agents IV: Inhibition of β-Hydroxy-β- Methylglutaryl Coenzyme A Reductase by Arylalkenyl and Arylepoxy Hydrogen Succinates and Glutarates", *J. Pharm. Sci.*, vol. 65, No. 5, pp. 724-727.
Coxon, F.P., et al., 2000, "Protein geranylgeranylation is required for osteoclast formation, function, and survival: inhibition by bisphosphonates and GGTI-298," *J.Bone Miner.Res.*, vol. 15, pp. 1467-1476.
Degenhardt, C.R., et al., 1986, "Synthesis of Ethenylidenebis(phosphonic acid) and its Tetraalkyl Esters," *J. Org. Chem.*, vol. 51, pp. 3488-3490.
Eberhard, A., et al., 1965, "Hydrolysis of Phostonates," *J. Amer. Chem. Soc.*, vol. 87, pp. 253-260.
Herczegh, P., et al, 2002, "Osteoadsorptive Bisphosphonate Derivatives of Fluoroquinolone Antibacterials," *J. Med. Chem.*, vol. 45, pp. 2338-2341.
Hughes, D.E., et al., 1997, "Apoptosis in bone physiology and disease," *Molecular Pathology*, vol. 50, pp. 132-137.
Kong, Y.Y., et al., 1999, "OPGL is a key regulator of osteoclastogenesis, lymphocyte development and lymph-node organogenesis," *Nature*, vol. 397, pp. 315-323.
Kudo, O., et al., 2003, "Interleukin-6 and interleukin-11 support human osteoclast formation by a RANKL-independent mechanism", *Bone*, vol. 32, No. 1, pp. 1-7.
Kusano, K., et al, 1998, "Regulation of matrix metalloproteinases (MMP-2, -3, -9, and -13) by interleukin-1 and interleukin-6 in mouse calvaria: association of MMP induction with bone resorption", *Endocrinology*, vol. 139, No. 3, pp. 1338-1345.
Luckman, et al., 1998, "Heterocycle-containing bisphosphonates cause apoptosis and inhibit bone resorption by preventing protein prenylation: evidence from structure- activity relationships in J774 macrophages," *J. Bone Miner.Res.*, vol. 13, pp. 1668-1678.
MacPherson, H; et al., 1999, "Expression and functional role of nitric oxide synthase isoforms in human osteoblast-like cells," *Bone*, vol. 24, pp. 179-185.
Mai, A., et al, 1997, "Arylketotetramethylene analogues of disoxaril and anti-human rhinovirus 14 activity", *Antiviral Chemistry & Chemotherapy*, vol. 8, No. 3, pp. 235-242.
Mundy, G.R., 1996, "Chapter 1: Bone Remodeling", in *Bone Remodeling and its disorders* (2nd edition), London, (Ed. Martin Dunitz), pp. 1-11.
Nociari, M.N., et al., 1998, "A novel one-step, highly sensitive fluorimetric assay to evaluate cell-mediated cytotoxicity," *Journal of Immunological Methods*, vol. 213, pp. 157-167.
Raisz, L.G., 1988, "Local and systemic factors in the pathogenesis of osteoporosis," *N. Engl. J. Med.*, vol. 318, pp. 818-828.
Ralston, S.H., 1997, "Science, Medicine and the Future: Osteoporosis," *Br. Med. J.*, vol. 315, pp. 469-472.
Rodan, G.A., et al., 1997, "The missing bone," *Cell*, vol. 89, pp. 677-680.
Takahashi, N.; et al., 1988, "Osteoblastic cells are involved in osteoclast formation," *Endocrinology*, vol. 123, pp. 2600-2602.
van't Hof, R.J., et a;., 1997, "Cytokine-induced nitric oxide inhibits bone resorption by inducing apoptosis of osteoclast progenitors and suppressing osteoclast activity," *J. Bone & Miner. Res.*, vol. 12, pp. 1797-1804.
Yasuda, H., et al, 1998, "Identity of osteoclastogenesis inhibitory factor (OCIF) and osteoprotegerin (OPG): a mechanism by which OPG/OCIF inhibits osteoclastogenesis in vitro," *Endocrinology*, vol. 139, pp. 1329-1337.
Yuan, Y.F. et al, 2000, "Studies on Volatile Oil in Ligusticum Chuanxiong by Supercritical Fluid Extraction", *Zhongguo Yaoxue Zazhi* (Beijing) (Clin. Pharm. J. (Beijing), vol. 35, No. 2, pp. 84-87 (with English abstract).
United Kingdom Patent Office Search Report for GB 0310463.5.
United Kingdom Patent Office Search Report for GB 0325259.0.
International Search Report (ISR) for PCT/GB2004/001958.
International Preliminary Report on Patentability (IPRP) for PCT/GB2004/001958.

KETONES AND REDUCED KETONES AS THERAPEUTIC AGENTS FOR THE TREATMENT OF BONE CONDITIONS

This application is a divisional of application Ser. No. 10/555,738, filed Jul. 14, 2006 (pending), which is the US national phase of international application PCT/GB2004/001958 filed 6 May 2004, which designated the U.S. and claims priority to GB 0310463.5 filed 7 May 2003, and GB 0325259.0 filed 29 Oct. 2003, the entire contents of each of which are hereby incorporated by reference.

TECHNICAL FIELD

The present invention pertains generally to the field of therapeutic compounds for treating bone conditions, and more specifically to certain ketones and reduced ketones and derivatives thereof which, inter alia, inhibit osteoclast survival, formation, and/or activity; and/or inhibit bone resorption. The present invention also pertains to pharmaceutical compositions comprising such compounds, and the use of such compounds and compositions, both in vitro and in vivo, to inhibit osteoclast survival, formation, and/or activity, and to inhibit conditions mediated by osteoclasts and/or characterised by bone resorption, in the treatment of bone disorders such as osteoporosis, rheumatoid arthritis, cancer associated bone disease, Paget's disease, aseptic loosening of prosthetic implants, and the like; and/or in the treatment of conditions associated with inflammation or activation of the immune system.

BACKGROUND

Throughout this specification, including the claims which follow, unless the context requires otherwise, the word "comprise," and variations such as "comprises" and "comprising," will be understood to imply the inclusion of a stated integer or step or group of integers or steps but not the exclusion of any other integer or step or group of integers or steps.

It must be noted that, as used in the specification and the appended claims, the singular forms "a," "an," and "the" include plural referents unless the context clearly dictates otherwise. Thus, for example, reference to "a pharmaceutical carrier" includes mixtures of two or more such carriers, and the like.

Ranges are often expressed herein as from "about" one particular value, and/or to "about" another particular value. When such a range is expressed, another embodiment includes from the one particular value and/or to the other particular value. Similarly, when values are expressed as approximations, by the use of the antecedent "about," it will be understood that the particular value forms another embodiments.

Functions of Bone

The function of bone is to provide mechanical support for joints, tendons and ligaments, to protect vital organs from damage and to act as a reservoir for calcium and phosphate in the preservation of normal mineral homeostasis. Diseases of bone compromise these functions, leading to clinical problems such as bone pain, bone deformity, fracture and abnormalities of calcium and phosphate homeostasis.

Types of Bone

The normal skeleton contains two types of bone: cortical or compact bone, which makes up most of shafts (diaphysis) of the long bones such as the femur and tibia, and trabecular or spongy bone which makes up most of the vertebral bodies and the ends of the long bones.

Trabecular bone has a greater surface area than cortical bone and because of this is remodeled more rapidly. This means that conditions associated with increased bone turnover tend to affect trabecular bone more quickly and more profoundly than cortical bone. Cortical bone is arranged in so-called Haversian systems which consists of a series of concentric lamellae of collagen fibres surrounding a central canal that contains blood vessels. Nutrients reach the central parts of the bone by an interconnecting system of canaliculi that run between osteocytes buried deep within bone matrix and lining cells on the bone surface. Trabecular bone has a similar structure, but here the lamellae run in parallel to the bone surface, rather than concentrically as in cortical bone.

Bone Composition

The organic component of bone matrix comprises mainly of type I collagen; a fibrillar protein formed from three protein chains, wound together in a triple helix. Collagen type I is laid down by bone forming cells (osteoblasts) in organised parallel sheets (lamellae) and subsequently the collagen chains become cross-linked by specialised covalent bonds which help to give bone its tensile strength. When bone is formed rapidly (for example in Paget's disease, or in bone metastases), the lamellae are laid down in a disorderly fashion giving rise to "woven bone", which is mechanically weak and easily fractured. Bone matrix also contains small amounts of other collagens and several non-collagenous proteins and glycoproteins. Some of these, such as osteocalcin, are specific to bone, whereas others, such as osteopontin and fibronectin and various peptide growth factors are also found in other connective tissues. The function of non-collagenous bone proteins is unclear, but it is thought that they are involved in mediating the attachment of bone cells to bone matrix, and in regulating bone cell activity during the process of bone remodelling. The organic component of bone forms a framework upon which mineralisation occurs. During bone formation, osteoblasts lay down uncalcified bone matrix (osteoid) which contains the components described above and small amounts of other proteins, which are adsorbed from extracellular fluid. After a lag phase of about 10 days, the matrix becomes mineralised, as hydroxyapatite (($Ca_{10}(PO_4)_6(OH)_2$) crystals are deposited in the spaces between collagen fibrils. Mineralisation confers upon bone the property of mechanical rigidity, which complements the tensile strength, and elasticity derived from bone collagen.

Bone Cell Function and Bone Remodelling

The mechanical integrity of the skeleton is maintained by the process of bone remodelling, which occurs throughout life, in order that damaged bone can be replaced by new bone. Remodelling can be divided into four phases; resorption; reversal, formation and quiescence (see, e.g., Raisz, 1988; Mundy, 1996). At any one time approximately 10% of bone surface in the adult skeleton is undergoing active remodelling whereas the remaining 90% is quiescent.

Osteoclast Formation and Differentiation

Remodelling commences with attraction of bone resorbing cells (osteoclasts) to the site, which is to be resorbed. These are multinucleated phagocytic cells, rich in the enzyme tartrate-resistant acid phosphatase, which are formed by fusion of precursors derived from the cells of monocyte/macrophage lineage. Recent work has identified several molecules that are of key importance in the regulation of osteoclast differentiation (see, e.g., Ralston, 1997). The transcription factor PU-1 which is expressed in early osteoclast precursors is necessary for the initial stages of osteoclast and monocyte differentiation, whereas other transcription factors including c-fos and NFkB play an essential role in stimulating differentiation of committed precursors to mature osteoclasts. Osteoclast formation and activation is also dependent on close contact between osteoclast precursors and bone marrow stromal cells. Stromal cells secrete the cytokine M-CSF (macrophage colony stimulating factor), which is essential for differentiation of both osteoclasts and macrophages from a common precursor. Stromal cells also express a molecule called RANK ligand (RANKL) on the cell surface, which interacts with another cell surface receptor present on osteoclast precursors called RANK (Receptor Activator of Nuclear Factor Kappa B) to promote differentiation of osteoclast precursors to mature osteoclasts. The RANK-RANKL interaction is blocked by another molecule called Osteoprotegerin (OPG), which is a "decoy" ligand for RANK and which acts a potent inhibitor of osteoclast formation (see, e.g., Kong et al., 1999; Yasuda et al., 1998). Recent work suggests that many of the factors that promote osteoclast formation and bone resorption do so by regulating expression of these molecules.

Mature osteoclasts form a tight seal over the bone surface and resorb bone by secreting hydrochloric acid and proteolytic enzymes through the "ruffled border" into a space beneath the osteoclast (Howship's lacuna). Formation of this ruffled border is critically dependent on the presence of c-src, a cell membrane associated signalling protein. The hydrochloric acid secreted by osteoclasts dissolves hydroxyapatite and allows proteolytic enzymes (mainly Cathepsin K and matrix metalloproteinases) to degrade collagen and other matrix proteins. Molecules which have been identified as being important in regulating osteoclast activity include; carbonic anhydrase II (Ca-II) which catalyses formation of hydrogen ions within osteoclasts; TCIRG1, which encodes a subunit of the osteoclast proton pump, and Cathepsin K which degrades collagen and other non-collagenous proteins. Deficiency of these proteins causes osteopetrosis which is a disease associated with increased bone density and osteoclast dysfunction. After resorption is completed osteoclasts undergo programmed cell death (apoptosis), in the so-called reversal phase which heralds the start of bone formation. It has recently been discovered that many of the drugs, which are used clinically to inhibit bone resorption, such as bisphosphonates and oestrogen do so by promoting osteoclast apoptosis (see, e.g., Hughes et al., 1997).

Osteoblast Formation and Differentiation

Bone formation begins with attraction of osteoblast precursors, which are derived from mesenchymal stem cells in the bone marrow, to the bone surface. Although these cells have the potential to differentiate into many cell types including adipocytes, myocytes, and chondrocytes it is now known that the key trigger for osteoblast differentiation is expression of a regulatory molecule called Cbfa1 in pre-osteoblasts (see, e.g., Rodan et al., 1997). Cbfa1 is a transcription factor that activates co-ordinated expression of genes characteristic of the osteoblast phenotype such as osteocalcin, type I collagen and alkaline phosphatase. In contrast, expression of the transcription factor PPARg promotes the cells towards adipocyte differentiation. It is currently thought that some cases of osteoporosis may occur because there is an imbalance between the rate of osteoblast and adipocyte differentiation in bone. Mature osteoblasts are plump cuboidal cells, which are responsible for the production of bone matrix. They are rich in the enzyme alkaline phosphatase and the protein osteocalcin, which are used clinically as serum markers of osteoblast activity. Osteoblasts lay down bone matrix which is initially unmineralised (osteoid), but which subsequently becomes calcified after about 10 days to form mature bone. During bone formation, some osteoblasts become trapped within the matrix and differentiate into osteocytes, whereas others differentiate into flattened "lining cells" which cover the bone surface. Osteocytes connect with one another and with lining cells on the bone surface by an intricate network of cytoplasmic processes, running through cannaliculi in bone matrix. Osteocytes appear to act as sensors of mechanical strain in the skeleton, and release signalling molecules such as prostaglandins and nitric oxide (NO), which modulate the function of neighbouring bone cells.

Regulation of Bone Remodeling

Bone remodelling is a highly organised process, but the mechanisms which determine where and when remodelling occurs are poorly understood. Mechanical stimuli and areas of micro-damage are likely to be important in determining the sites at which remodelling occurs in the normal skeleton. Increased bone remodelling may result from local or systemic release of inflammatory cytokines like interleukin-1 and tumour necrosis factor in inflammatory diseases. Calciotropic hormones such as parathyroid hormone (PTH) and 1,25-dihydroxyvitamin D, act together to increase bone remodelling on a systemic basis allowing skeletal calcium to be mobilised for maintenance of plasma calcium homeostasis. Bone remodelling is also increased by other hormones such as thyroid hormone and growth hormone, but suppressed by oestrogen, androgens and calcitonin.

Common Bone Diseases

Osteoporosis is a common disease characterized by reduced bone density, deterioration of bone tissue and increase risk of fracture. Many factors contribute to the pathogenesis of osteoporosis including poor diet, lack of exercise, smoking and excessive alcohol intake. Osteoporosis may also arise in association with inflammatory diseases such as rheumatoid arthritis, endocrine diseases such as thyrotoxicosis and with certain drug treatments such as glucocorticoids. However one of the most important factors in the pathogenesis of osteoporosis is heredity.

Paget's disease of bone is a common condition of unknown cause, characterized by increased bone turnover and disorganized bone remodelling, with areas of increased osteoclastic and osteoblast activity. Although Pagetic bone is often denser than normal, the abnormal architecture causes the bone to be mechanically weak, resulting in bone deformity and increased susceptibility to pathological fracture.

Multiple Myeloma is a cancer of plasma cells. In contrast to most other haematological malignancies, the tumour cells do not circulate in the blood, but accumulate in the bone marrow where they give rise to high levels of cytokines that activate osteoclastic bone resorption (e.g., interleukin-6). The disease accounts for approximately 20% of all haematological cancers and is mainly a disease of elderly people.

Bone Resorption Inhibitors

Several common diseases, such as osteoporosis and rheumatoid arthritis, are characterised by bone loss due to excess bone resorption by osteoclasts. At present the most commonly used types of drugs used to suppress osteoclast activity in these diseases are bisphosphonates (BPs) and non-steroidal anti-inflammatory drugs (NSAIDs).

Bisphosphonates (also know as diphosphonates) are an important class of drugs used in the treatment of bone diseases involving excessive bone destruction or resorption, e.g., Paget's disease, tumour-associated osteolysis, and post-menopausal osteoporosis. Bisphosphonates are structural analogues of naturally occurring pyrophosphate.

Whereas pyrophosphate consists of two phosphate groups linked by an oxygen atom (P—O—P), bisphosphonates have two phosphate groups linked by a carbon atom (P—C—P). This makes bisphosphonates very stable and resistant to degradation. Furthermore, like pyrophosphate, bisphosphonates have very high affinity for calcium and therefore target to bone mineral in vivo. The carbon atom that links the two phosphate groups has two side chains attached to it, which can be altered in structure. This gives rise to a multitude of bisphosphonate compounds with different anti-resorptive potencies. Bone resorption is mediated by highly specialised, multinucleated osteoclast cells. Bisphosphonate drugs specifically inhibit the activity and survival of these cells. Firstly, after intravenous or oral administration, the bisphosphonates are rapidly cleared from the circulation and bind to bone mineral. As the mineral is then resorbed and dissolved by osteoclasts, it is thought that the drug is released from the bone mineral and is internalised by osteoclasts. Intracellular accumulation of the drugs inhibits the ability of the cells to resorb bone (probably by interfering with signal transduction pathways or cellular metabolism) and causes osteoclast apoptosis.

NSAIDs are widely used in the treatment of inflammatory diseases, but often cause severe gastro-intestinal (GI) side effects. NSAIDs developed by Nicox SA (Sophia Antipolis, France), that contain a nitric oxide (NO)-donor group (NO-NSAID) exhibit anti-inflammatory properties without causing GI side effects. An example of such a compound is HCT 1026, which is a nitrosylated derivative of the NSAID flurbiprofen (see, for example, Armour et al., 2001).

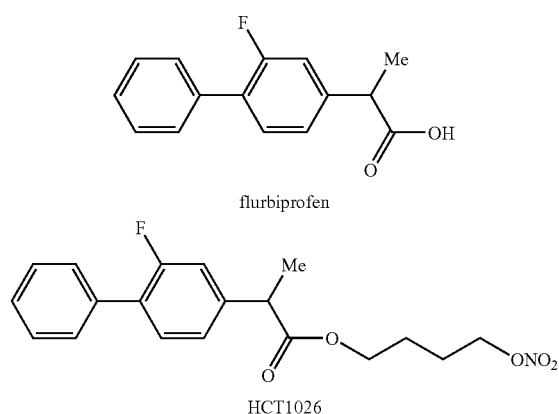

flurbiprofen

HCT1026

Ralston et al., 2003, describe alkane diol derivatives, including alkane diol esters and diesters, for use as therapeutic agents in the treatment of bone conditions.

Barta et al., 2002, describe certain aromatic sulfone hydroxamates apparently useful as protease inhibitors, including, for example, the following compound (IIA-31 on page 35 therein):

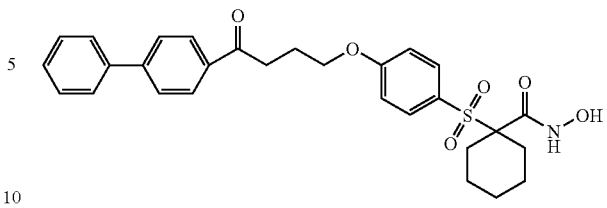

Naka et al., 2002, describe certain N-acylaminoalkane hydroxamic acids apparently useful as IL-6 production inhibitors, including, for example, the following compound:

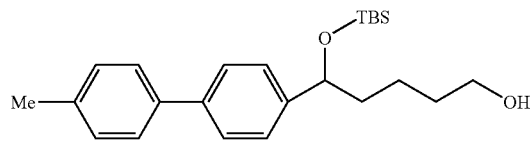

Inukai et al., 1977, describe certain 4-alkylbiphenyls, including, for example, the following compound:

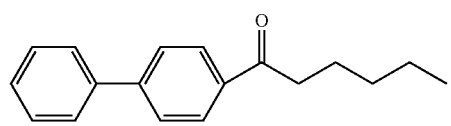

Boots et al., 1976, describe certain arylalkenylcarbinols, apparently useful as hypocholesterolemic agents in the treatment of atherosclerosis, including, for example, the following compound:

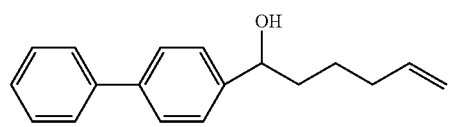

Boots et al., 1973, describe certain arylalkenylcarbinols, apparently useful as hypocholesterolemic agents in the treatment of atherosclerosis, including, for example, the following compound:

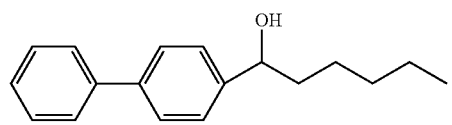

Additional documents which disclose aryl ketones compounds include: Shibata et al., 1999; Hickey et al., 1997; Tew et al., 1997; Mai et al., 1997; Yuan et al., 2000; Konno et al., 2002.

There is a recognized need for more and better treatments for bone-related diseases which offer, for example, one or more the following benefits:

(a) improved activity;

(b) improved efficacy;

(c) improved specificity;

(d) reduced toxicity (e.g., cytotoxicity);

(e) complement the activity of other treatments (e.g., chemotherapeutic agents);

(f) reduced intensity of undesired side-effects;

(g) fewer undesired side-effects;

(h) simpler methods of administration (e.g., route, timing, compliance);

(i) reduction in required dosage amounts;

(j) reduction in required frequency of administration;

(k) increased ease of synthesis, purification, handling, storage, etc.;

(l) reduced cost of synthesis, purification, handling, storage, etc.

Thus, one aim of the present invention is the provision of active compounds which offer one or more of the above benefits.

SUMMARY OF THE INVENTION

One aspect of the invention pertains to active compounds, specifically, certain ketones and reduced ketones and derivatives thereof, as described herein.

Another aspect of the invention pertains to a composition comprising an active compound as described herein and a pharmaceutically acceptable carrier or diluent.

Another aspect of the invention pertains to a method of inhibiting osteoclast survival, formation, and/or activity, in vitro or in vivo, comprising contacting an osteoclast with an effective amount of an active compound, as described herein.

Another aspect of the invention pertains to a method of inhibiting bone resorption, in vitro or in vivo, comprising contacting cells in the bone microenvironment with a therapeutically-effective amount of an active compound, as described herein.

Another aspect of the present invention pertains to a method for the treatment comprising administering to a subject in need of treatment a therapeutically-effective amount of an active compound, as described herein, preferably in the form of a pharmaceutical composition.

Another aspect of the present invention pertains to an active compound as described herein for use in a method of treatment of the human or animal body by therapy.

Another aspect of the present invention pertains to use of an active compound, as described herein, in the manufacture of a medicament for use in treatment.

In one embodiment, the treatment is treatment of a bone disorder, for example, a condition mediated by osteoclasts and/or characterised by bone resorption, as described herein. In one embodiment, the treatment is treatment of a condition mediated by osteoclasts, as described herein. In one embodiment, the treatment is treatment of a condition characterised by bone resorption, as described herein.

In one embodiment, the treatment is treatment of osteoporosis, rheumatoid arthritis, cancer associated bone disease, Paget's disease, or aseptic loosening of prosthetic implants.

In one embodiment, the treatment is treatment of a condition associated with inflammation or activation of the immune system, as described herein.

Another aspect of the present invention pertains to a kit comprising (a) an active compound, as described herein, preferably provided as a pharmaceutical composition and in a suitable container and/or with suitable packaging; and (b) instructions for use, for example, written instructions on how to administer the active compound.

Another aspect of the present invention pertains to compounds obtainable by a method of synthesis as described herein, or a method comprising a method of synthesis as described herein.

Another aspect of the present invention pertains to compounds obtained by a method of synthesis as described herein, or a method comprising a method of synthesis as described herein.

Another aspect of the present invention pertains to novel intermediates, as described herein, which are suitable for use in the methods of synthesis described herein.

Another aspect of the present invention pertains to the use of such novel intermediates, as described herein, in the methods of synthesis described herein.

As will be appreciated by one of skill in the art, features and preferred embodiments of one aspect of the invention will also pertain to other aspect of the invention.

DETAILED DESCRIPTION OF THE INVENTION

Figure 1:
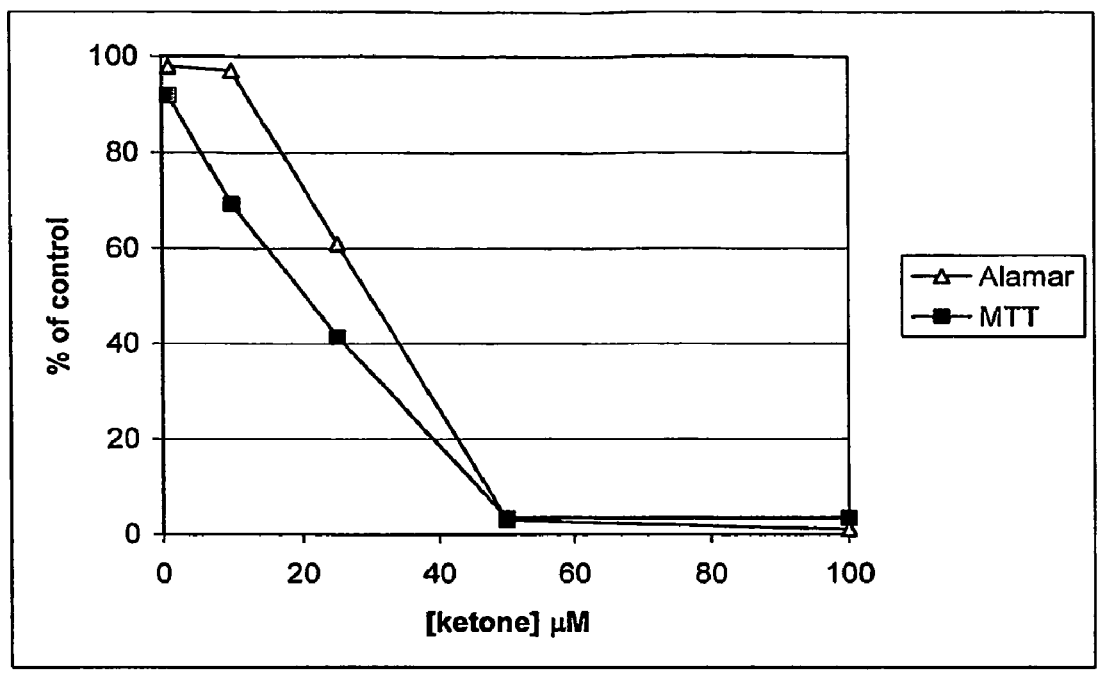
FIG. 1 is a graph of macrophage viability, as measured by the MTT (■) and Alamar Blue (Δ) macrophage J774 viability assays, expressed as percent (%) of control, after 72 hours exposure to 6-hydroxy-1-(4-biphenyl) hexan-1-one (ABD-68) as a function of compound concentration.

One aspect of the present invention pertains to compounds which may be described as "aryl alkyl ketones and aryl alkyl reduced ketones and derivatives thereof", and their surprising and unexpected osteoclast-inhibitory and resorption-inhibitory effects.

One aspect of the present invention pertains to compounds of the following formulae, and pharmaceutically acceptable salts, solvates, amides, esters, ethers, chemically protected forms, or prodrugs thereof:

$$Ar^1-\overset{O}{\underset{\|}{C}}-R^{alk}-Q \quad (1)$$

$$Ar^1-\underset{H}{\overset{O^{R^O}}{\underset{|}{C}}}-R^{alk}-Q \quad (2)$$

In one embodiment, the compounds are compounds of formula (1) ("ketones"), and pharmaceutically acceptable salts, solvates, amides, esters, ethers, chemically protected forms, or prodrugs thereof.

In one embodiment, the compounds are compounds of formula (2) ("reduced ketones"), and pharmaceutically acceptable salts, solvates, amides, esters, ethers, chemically protected forms, or prodrugs thereof.

The Group $Ar^1$

In one embodiment, $Ar^1$ is independently a $C_{5-20}$aryl group, and is optionally substituted (e.g., with one or more groups as defined for $R^P$).

In one embodiment, $Ar^1$ is independently phenyl, naphthyl, phenanthryl, fluorenyl, anthracenyl; furanyl, thienyl, pyrrolyl, imidazolyl, pyrazolyl, oxazolyl, thiazolyl; pyridyl, pyrazinyl, pyrimidinyl, pyridazinyl; indolyl; benzimidazolyl, benzothiofuranyl; quinolinyl; acridinyl, or carbazolyl; and is optionally substituted.

In one embodiment, $Ar^1$ is independently a C aryl group, and is optionally substituted.

In one embodiment, $Ar^1$ is independently phenyl, furanyl, thienyl, pyrrolyl, imidazolyl, pyrazolyl, oxazolyl, thiazolyl; pyridyl, pyrazinyl, pyrimidinyl, or pyridazinyl; and is optionally substituted.

In one embodiment, $Ar^1$ is independently a $C_{5-20}$-carboaryl group, and is optionally substituted.

The Group $Ar^1$: Optionally Substituted Phenyl

In one embodiment, $Ar^1$ is independently an optionally substituted phenyl group of the following formula:

wherein each $R^P$ is independently a phenyl substituent; and p is independently an integer from 0 to 5.

In one embodiment, p is an integer from 0 to 4; 0 to 3; 0 to 2; 0 or 1; 0.

In one embodiment, p is an integer from 1 to 4; 1 to 3; 1 or 2; 1.

The Group $Ar^1$: Optionally Substituted Biphenyl, Phenanthryl, Fluorenyl, Carbazolyl In one embodiment, $Ar^1$ is independently biphenyl, phenanthyl, fluorenyl, or carbazolyl (e.g., derived from biphenyl, phenanthrene, fluorene, or carbazole, respectively), and is optionally substituted.

biphenyl    phenanthrene fluorene    carbazole

The Group $Ar^1$: Optionally Substituted Biphenyl

In one embodiment, $Ar^1$ is independently an optionally substituted biphenyl group of the following formula:

wherein:

each $R^P$ is independently a phenyl substituent;

q is independently an integer from 0 to 4; and r is independently an integer from 0 to 5.

In one embodiment, q is an integer from 0 to 4; 0 to 3; 0 to 2; 0 or 1; 0.

In one embodiment, q is an integer from 1 to 4; 1 to 3; 1 or 2; 1.

In one embodiment, r is an integer from 0 to 5; 0 to 4; 0 to 3; 0 to 2; 0 or 1; 0.

In one embodiment, r is an integer from 1 to 5; 1 to 4; 1 to 3; 1 or 2; 1.

In one embodiment, q is 0, and $Ar^1$ is an optionally substituted biphenyl group of the following formula (e.g., biphenyl-2-yl, biphenyl-3-yl, biphenyl-4-yl):

The Group Ar¹: Optionally Substituted Biphenyl-4-yl

In one embodiment, Ar¹ is independently an optionally substituted biphenyl-4-yl group of the following formula:

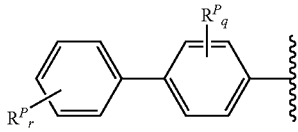

In one embodiment, Ar¹ is independently is an optionally substituted biphenyl-4-yl group of the following formula:

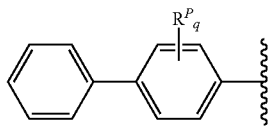

In one embodiment, Ar¹ is independently an optionally substituted biphenyl-4-yl group of the following formula:

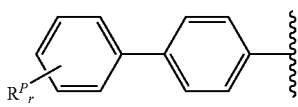

The Group Ar¹: 4'-Substituted Biphenyl-4-yl

In one embodiment, Ar¹ is independently a 4'-substituted biphenyl-4-yl group of the following formula:

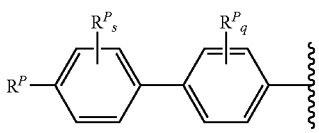

wherein s is independently an integer from 0 to 4.

In one embodiment, s is an integer from 0 to 4; 0 to 3; 0 to 2; 0 or 1; 0.

In one embodiment, s is an integer from 1 to 4; 1 to 3; 1 to 2; 1.

In one embodiment, Ar¹ is independently a 4'-substituted biphenyl-4-yl group of the following formula:

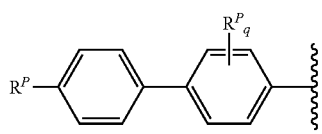

In one embodiment, Ar¹ is independently a 4'-substituted biphenyl-4-yl group of the following formula:

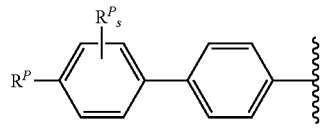

In one embodiment, Ar¹ is independently a 4'-substituted biphenyl-4-yl group of the following formula:

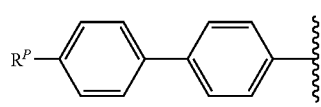

The Group Ar¹: 3'-Substituted Biphenyl-4-yl

In one embodiment, Ar¹ is independently a 3'-substituted biphenylyl group of the following formula:

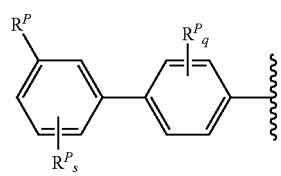

In one embodiment, Ar¹ is independently a 3'-substituted biphenyl-4-yl group of the following formula:

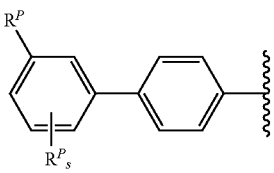

In one embodiment, Ar¹ is independently a 3'-substituted biphenyl-4-yl group of the following formula:

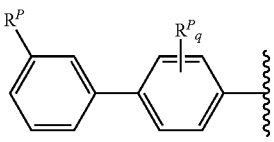

In one embodiment, Ar¹ is independently a 3'-substituted biphenyl-4-yl group of the following formula:

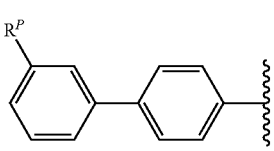

The Group Ar¹: 3',4'-Disubstituted Biphenyl-4-yl

In one embodiment, Ar¹ is independently a 3',4'-disubstituted biphenyl-4-yl group of the following formula:

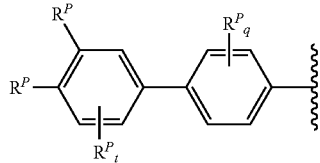

wherein t is independently an integer from 0 to 3.

In one embodiment, t is an integer from 0 to 3; 0 to 2; 0 or 1; 0.

In one embodiment, t is an integer from 1 to 3; 1 or 2; 1.

In one embodiment, Ar¹ is independently a 3',4'-disubstituted biphenylyl group of the following formula:

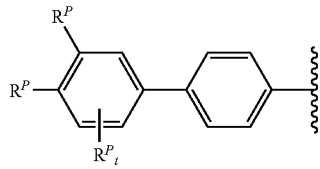

In one embodiment, Ar¹ is independently a 3',4'-disubstituted biphenyl-4-yl group of the following formula:

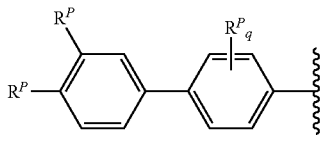

In one embodiment, Ar¹ is independently a 3',4'-disubstituted biphenyl-4-yl group of the following formula:

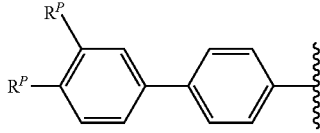

The Group Ar¹: 2'-Substituted Biphenyl-4-yl

In one embodiment, Ar¹ is independently a 2'-substituted biphenyl-4-yl group of the following formula:

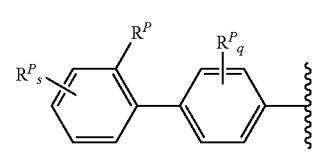

In one embodiment, Ar¹ is independently a 2'-substituted biphenyl-4-yl group of the following formula:

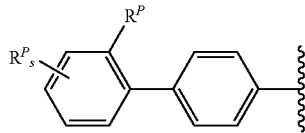

In one embodiment, Ar¹ is independently a 2'-substituted biphenyl-4-yl group of the following formula:

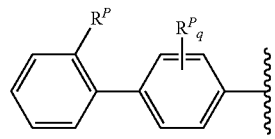

In one embodiment, Ar¹ is independently a 2'-substituted biphenyl-4-yl group of the following formula:

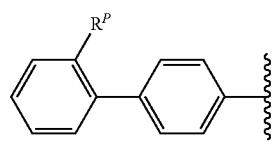

The Group Ar¹: 2',4'-Disubstituted Biphenyl-4-yl

In one embodiment, Ar¹ is independently a 2',4'-disubstituted biphenyl-4-yl group of the following formula:

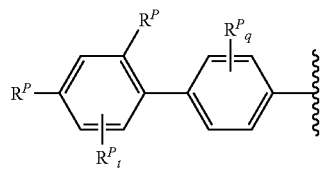

In one embodiment, Ar¹ is independently a 2',4'-disubstituted biphenyl-4-yl group of the following formula:

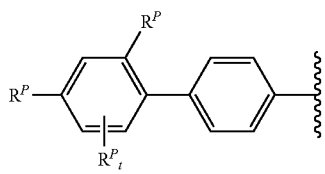

In one embodiment, Ar¹ is independently a 2',4'-disubstituted biphenyl-4-yl group of the following formula:

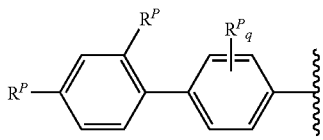

In one embodiment, Ar¹ is independently a 2',4'-disubstituted biphenyl-4-yl group of the following formula:

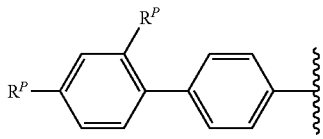

The Group Ar¹: Unsubstituted Biphenyl-4-yl

In one embodiment, Ar¹ is independently an unsubstituted biphenyl-4-yl group of the following formula:

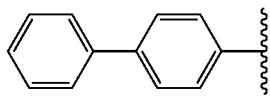

The Group Ar¹: Optionally Substituted Phenanthryl

In one embodiment, Ar¹ is independently phenanthyl (e.g., phenanthr-2-yl), and is optionally substituted.

In one embodiment, Ar¹ is independently an optionally substituted phenanthyl group of the following formula:

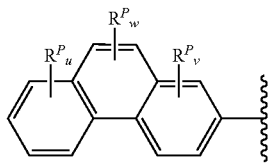

wherein:

each $R^P$ is independently a phenanthyl substituent (as defined herein for phenyl substituents);

u is independently an integer from 0 to 4;

v is independently an integer from 0 to 3; and w is independently an integer from 0 to 2.

In one embodiment, w is an integer from 0 to 2; 0 or 1; 0.
In one embodiment, w is an integer from 1 or 2; 1.

The Group Ar¹: Optionally Substituted Fluorenyl

In one embodiment, Ar¹ is independently fluorenyl (e.g., fluoren-2-yl), and is optionally substituted.

In one embodiment, Ar¹ is independently an optionally substituted fluorenyl group of the following formula:

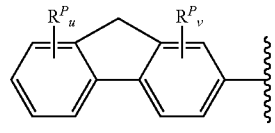

wherein:

each $R^P$ is independently a fluorenyl substituent (as defined herein for phenyl substituents);

u is independently an integer from 0 to 4; and v is independently an integer from 0 to 3.

In one embodiment, u is an integer from 0 to 4; 0 to 3; 0 to 2; 0 or 1; 0.
In one embodiment, u is an integer from 1 to 4; 1 to 3; 1 or 2; 1.
In one embodiment, v is an integer from 0 to 3; 0 to 2; 0 or 1; 0.
In one embodiment, v is an integer from 1 to 3; 1 or 2; 1.

The Group Ar¹: Optionally Substituted Carbazolyl

In one embodiment, Ar¹ is independently carbazolyl (e.g., carbazol-2-yl), and is optionally substituted.

In one embodiment, Ar¹ is independently an optionally substituted carbazolyl group of the following formula:

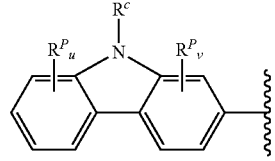

wherein:

each $R^P$ is independently a carbazolyl substituent (as defined herein for phenyl substituents);

u is independently an integer from 0 to 4;

v is independently an integer from 0 to 3; and $R^c$ is independently —H or as defined in (4), (17), (20), (21), (22) or (23) below.

In one embodiment, u is an integer from 0 to 4; 0 to 3; 0 to 2; 0 or 1; 0.
In one embodiment, u is an integer from 1 to 4; 1 to 3; 1 or 2; 1.
In one embodiment, v is an integer from 0 to 3; 0 to 2; 0 or 1; 0.
In one embodiment, v is an integer from 1 to 3; 1 or 2; 1.

Phenyl Substituents, $R^P$

Examples of phenyl substituents, $R^P$, include, but are not limited to, those described below under the heading "substituents."

In one embodiment, each of the substituents (e.g., $R^P$) is independently selected from: (1) carboxylic acid; (2) ester; (3) amido; (4) acyl; (5) halo; (6) cyano; (7) nitro; (8) hydroxy; (9) ether; (10) thiol; (11) thioether; (12) acyloxy; (13) amino; (14) acylamino; (15) aminoacylamino; (16) sulfonamino; (17) sulfonyl; (18) sulfonate; (19) sulfonamido; (20)

$C_{5-20}$aryl-$C_{1-7}$alkyl; (21) $C_{5-20}$aryl; (22) $C_{3-20}$heterocyclyl; (23) $C_{1-7}$alkyl; (24) oxo; (25) imino; (26) hydroxyimino; (27) phosphate.

In one embodiment, each of the substituents (e.g., $R^P$) is independently selected from:

(1) —C(=O)OH;

(2) —C(=O)OR$^1$, wherein R$^1$ is independently as defined in (20), (21), (22) or (23);

(3) —C(=O)NR$^2$R$^3$ or —C(=S)NR$^2$R$^3$, wherein each of R$^2$ and R$^3$ is independently —H; or as defined in (20), (21), (22) or (23); or R$^2$ and R$^3$ taken together with the nitrogen atom to which they are attached form a ring having from 3 to 7 ring atoms;

(4) —C(=O)R$^4$, wherein R$^4$ is independently as defined in (20), (21), (22) or (23);

(5) —F, —Cl, —Br, —I;

(6) —CN;

(7) —NO$_2$;

(8) —OH;

(9) —OR$^5$, wherein R$^5$ is independently as defined in (20), (21), (22) or (23);

(10) —SH;

(11) —SR$^6$, wherein R$^6$ is independently as defined in (20), (21), (22) or (23);

(12) —OC(=O)R$^7$, wherein R$^7$ is independently as defined in (20), (21), (22) or (23);

(13) —NR$^8$R$^9$, wherein each of R$^8$ and R$^9$ is independently —H; or as defined in (20), (21), (22) or (23); or R$^6$ and R$^9$ taken together with the nitrogen atom to which they are attached form a ring having from 3 to 7 ring atoms;

(14) —NR$^{10}$C(=O)R$^{11}$ or —NR$^{10}$C(=S)R$^{11}$, wherein R10 is independently —H; or as defined in (20), (21), (22) or (23); and R$^{11}$ is independently —H, or as defined in (20), (21), (22) or (23);

(15) —NR$^{12}$C(=O)NR$^{13}$R$^{14}$ or —NR$^{12}$C(=S)NR$^{13}$R$^{14}$, wherein R$^{12}$ is independently —H; or as defined in (20), (21), (22) or (23); and each of R$^{13}$ and R$^{14}$ is independently —H; or as defined in (20), (21), (22) or (23); or R$^{13}$ and R$^{14}$ taken together with the nitrogen atom to which they are attached form a ring having from 3 to 7 ring atoms;

(16) —NR$^{15}$SO$_2$R$^{16}$, wherein R$^5$ is independently —H; or as defined in (20), (21), (22) or (23); and R$^{16}$ is independently —H, or as defined in (20), (21), (22) or (23);

(17) —SO$_2$R$^{17}$, wherein R$^{17}$ is independently as defined in (20), (21), (22) or (23);

(18) —OSO$_2$R$^{18}$ and wherein R$^{18}$ is independently as defined in (20), (21), (22) or (23);

(19) —SO$_2$NR$^{19}$R$^{20}$, wherein each of R$^{19}$ and R$^{20}$ is independently —H; or as defined in (20), (21), (22) or (23); or R$^{19}$ and R$^{20}$ taken together with the nitrogen atom to which they are attached form a ring having from 3 to 7 ring atoms;

(20) $C_{5-20}$aryl-$C_{1-7}$alkyl, for example, wherein $C_{5-20}$aryl is as defined in (21); unsubstituted or substituted with one or more groups as defined in (1) to (27);

(21) $C_{5-20}$aryl, including $C_{6-20}$carboaryl and $C_{5-20}$heteroaryl; unsubstituted or substituted with one or more groups as defined in (1) to (27);

(22) $C_{3-20}$heterocyclyl; unsubstituted or substituted with one or more groups as defined in (1) to (27);

(23) $C_{1-7}$alkyl, including:
unsaturated $C_{1-7}$alkyl, e.g., $C_{2-7}$alkenyl and $C_{2-7}$alkynyl;
cyclic $C_{1-7}$alkyl, e.g., $C_{3-7}$cycloalkyl $C_{3-7}$cycloalkenyl, $C_{3-7}$cycloalkynyl;

$C_{1-7}$alkyl substituted with one or more groups as defined in (1) to (22) and (24) to (27),
e.g., halo-$C_{1-7}$alkyl;
e.g., amino-$C_{1-7}$alkyl (e.g., —(CH$_2$)$_w$-amino, w is 1, 2, 3, or 4);
e.g., carboxy-$C_{1-7}$alkyl (e.g., —(CH$_2$)$_w$—COOH, w is 1, 2, 3, or 4);
e.g., hydroxy-$C_{1-7}$alkyl (e.g., —(CH$_2$)$_w$—OH, w is 1, 2, 3, or 4);
e.g., $C_{1-7}$alkoxy-$C_{1-7}$alkyl (e.g., —(CH$_2$)$_w$—O—$C_{1-7}$alkyl, w is 1, 2, 3, or 4);

(24) =O;

(25) =NR$^{21}$, wherein R$^{21}$ is independently —H; or as defined in (20), (21), (22) or (23);

(26)=NOH;

(27) —P(=O)(OR$^{22}$)$_2$ and —OP(=O)(OR$^{22}$)$_2$, wherein R$^{22}$ is independently —H; or as defined in (20), (21), (22) or (23).

In one embodiment, each of the substituents (e.g., R$^A$) is independently selected from:

(1) —C(=O)OH;

(2) —C(=O)OMe, —C(=O)OEt, —C(=O)O(iPr), —C(=O)O(tBu); —C(=O)O(cPr); —C(=O)OCH$_2$CH$_2$OH, —C(=O)OCH$_2$CH$_2$OMe, —C(=O)OCH$_2$CH$_2$OEt; —C(=O)OPh, —C(=O)OCH$_2$Ph;

(3) —(C=O)NH$_2$, —(C=O)NMe$_2$, —(C=O)NEt$_2$, —(C=O)N(iPr)$_2$, —(C=O)N(CH$_2$CH$_2$OH)$_2$; —(C=O)-morpholino, —(C=O)NHPh, —(C=O)NHCH$_2$Ph;

(4) —(C=O)Me, —(C=O)Et, —(C=O)(tBu), —(C=O)-cHex, —(C=O)Ph; —(C=O)CH$_2$Ph;

(5) —F, —Cl, —Br, —I;

(6) —CN;

(7) —NO$_2$;

(8) —OH;

(9) —OMe, —OEt, —O(iPr), —O(tBu), —OPh, —OCH$_2$Ph; —OCF$_3$, —OCH$_2$CF$_3$; —OCH$_2$CH$_2$OH, —OCH$_2$CH$_2$OMe, —OCH$_2$CH$_2$OEt; —OCH$_2$CH$_2$NH$_2$, —OCH$_2$CH$_2$NMe$_2$, —OCH$_2$CH$_2$N(iPr)$_2$; —OPh-Me, —OPh-OH, —OPh-OMe, —OPh-F, —OPh-Cl, —OPh-Br, —OPh-I;

(10) —SH;

(11) —SMe, —SEt, —SPh, —SCH$_2$Ph;

(12) —OC(=O)Me, —OC(=O)Et, —OC(=O)(iPr), —OC(=O)(tBu); —OC(=O)(cPr); —OC(=O)CH$_2$CH$_2$OH, —OC(=O)CH$_2$CH$_2$OMe, —OC(=O)CH$_2$CH$_2$OEt; —OC(=O)Ph, —OC(=O)CH$_2$Ph;

(13) —NH$_2$, —NHMe, —NHEt, —NH(iPr), —NMe$_2$, —NEt$_2$, —N(iPr)$_2$, —N(CH$_2$CH$_2$OH)$_2$; —NHPh, —NHCH$_2$Ph; piperidino, piperazino, morpholino;

(14) —NH(C=O)Me, —NH(C=O)Et, —NH(C=O)Ph, —NHC(=O)CH$_2$Ph; —NMe(C=O)Me, —NMe(C=O)Et, —NMe(C=O)Ph, —NMeC(=O)CH$_2$Ph;

(15) —NH(C=O)NH$_2$, —NH(C=O)NHMe, —NH(C=O)NHEt, —NH(C=O)NPh, —NH(C=O)NHCH$_2$Ph; —NH(C=S)NH$_2$, —NH(C=S)NHMe, —NH(C=S)NHEt, —NH(C=S)NPh, —NH(C=S)NHCH$_2$Ph;

(16) —NHSO$_2$Me, —NHSO$_2$Et, —NHSO$_2$Ph, —NHSO$_2$PhMe, —NHSO$_2$CH$_2$Ph; —NMeSO$_2$Me, —NMeSO$_2$Et, —NMeSO$_2$Ph, —NMeSO$_2$PhMe, —NMeSO$_2$CH$_2$Ph;

(17) —SO$_2$Me, —SO$_2$CF$_3$, —SO$_2$Et, —SO$_2$Ph, —SO$_2$PhMe, —SO$_2$CH$_2$Ph;

(18) —OSO$_2$Me, —OSO$_2$CF$_3$, —OSO$_2$Et, —OSO$_2$Ph, —OSO$_2$PhMe, —OSO$_2$CH$_2$Ph;

(19) —SO$_2$NH$_2$, —SO$_2$NHMe, —SO$_2$NHEt, —SO$_2$NMe$_2$, —SO$_2$NEt$_2$, —SO$_2$-morpholino, —SO$_2$NHPh, —SO$_2$NHCH$_2$Ph;
(20) —CH$_2$Ph, —CH$_2$Ph-Me, —CH$_2$Ph-OH, —CH$_2$Ph-F, —CH$_2$Ph-Cl;
(21) -Ph, -Ph-Me, -Ph-OH, -Ph-OMe, -Ph-F, -Ph-Cl, -Ph-Br, -Ph-I; pyridyl, pyrazinyl, pyrimidinyl, pyridazinyl; furanyl, thiophenyl, pyrrolyl, imidazolyl, pyrazolyl, oxazolyl, thiazolyl;
(22) pyrrolidinyl, piperidinyl, azepinyl, tetrahydropyranyl, morpholinyl, azetidinyl, piperazinyl, imidazolinyl, piperazinedionyl, and oxazolinonyl;
(23) -Me, -Et, -nPr, -iPr, -nBu, -iBu, -sBu, -tBu, -nPe;
-cPr, -cHex; —CH=CH$_2$, —CH$_2$—CH=CH$_2$;
—CF$_3$, —CHF$_2$, —CH$_2$F, —CCl, —CBr$_3$, —CH$_2$CH$_2$F, —CH$_2$CHF$_2$, and —CH$_2$CF$_3$;
—CH$_2$OH, —CH$_2$OMe, —CH$_2$OEt, —CH$_2$NH$_2$, —CH$_2$NMe$_2$;
—CH$_2$CH$_2$OH, —CH$_2$CH$_2$OMe, —CH$_2$CH$_2$OEt, —CH$_2$CH$_2$CH$_2$NH$_2$, —CH$_2$CH$_2$NMe$_2$;
(24) =O;
(25) =NH, =NMe; =NEt;
(26) =NOH;
(27) —OP(=O)(OH)$_2$, —P(=O)(OH)$_2$, —OP(=O)(OMe)$_2$, —P(=O)(OMe)$_2$.

In one embodiment, each of the substituents (e.g., R$^P$) is independently selected from:
(1) —C(=O)OH;
(2) —C(=O)OMe, —C(=O)OEt, —C(=O)O(tBu), —C(=O)OPh;
(3) —C(=O)NH$_2$, —C(=O)NHMe, —C(=O)NMe$_2$, —C(=O)NHPh;
(4) —C(=O)Me;
(5) —F, —Cl, —Br, —I;
(6) —CN;
(7) —NO$_2$;
(8) —OH;
(9) —OMe, —OEt, —O(iPr), —O(nPr), —O(tBu), —OPh, —OBn;
(11) —SMe;
(12) —OC(C=O)Me, —OC(C=O)Et, —OC(C=O)(tBu), —OC(C=O)Ph;
(13) —NH$_2$, —NHMe, —NMe$_2$, —NHEt, —NEt$_2$;
(14) —NHC(=O)Me, —NHC(=O)Et, —NHC(=O)Ph;
(17) —S(=O)$_2$Me, —S(=O)$_2$Et, —S(=O)$_2$Ph.
(19) —SO$_2$NH$_2$,
(21) -Ph;
(23) -Me, -Et, -iPr, -nPr, -cPr, -tBu, —CF$_3$;
(27) —P(=O)(OMe)$_2$.

In one embodiment, each of the substituents (e.g., R$^P$) is independently selected from: -Me, —F, —Cl, —Br, —I, —OH, —OMe, —NH$_2$, —NMe$_2$, —NO$_2$, and —CN.

In one embodiment, each of the substituents (e.g., R$^P$) is independently selected from: -Me, —F, —Cl, —OH, —OMe, —NH$_2$, —NMe$_2$, —NO$_2$, and —CN.

In one embodiment, each of the substituents (e.g., R$^P$) is independently selected from: —F, —Cl, —Br, —I, —NO$_2$, and —OH.

In one embodiment, each of the substituents (e.g., R$^P$) is independently selected from: —F, —Cl, —Br, and —I, —NO$_2$.

In one embodiment, each of the substituents (e.g., R$^P$) is independently selected from: —F, —Cl, —Br, —I.

In one embodiment, each of the substituents (e.g., R$^P$) is independently selected from: —F and —Br.

In one embodiment, each of the substituents (e.g., R$^P$) is: —F.

Examples of Some Preferred Fluoro-Substituted Phenyl Ar$^1$ Groups

Some examples of substituted phenyl groups, suitable as Ar$^1$, include the following:

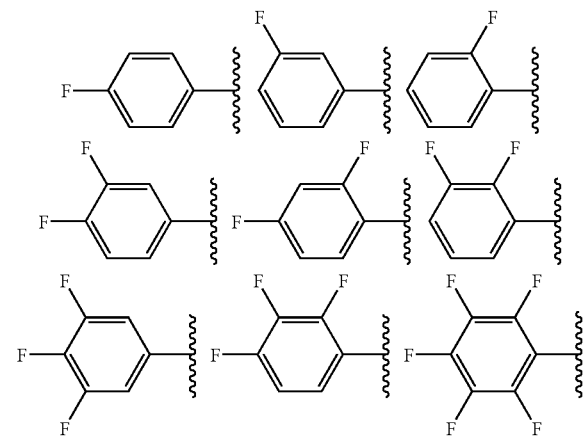

One especially preferred substituted phenyl group, suitable as Ar$^1$, is:

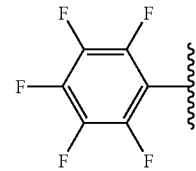

Examples of Some Preferred Substituted Biphenyl-4-yl Ar$^1$ Groups

Some examples of substituted biphenyl-4-yl groups, suitable as Ar$^1$, include the following:

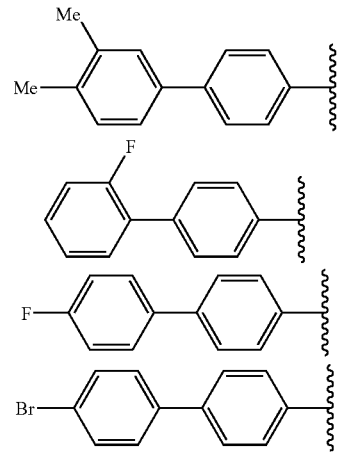

-continued
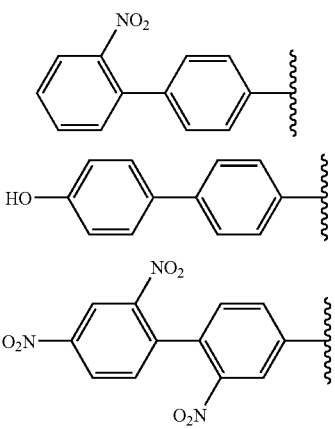
Examples of Some Preferred Fluoro-Substituted
Biphenyl-4-yl Ar¹ Groups
Some examples of substituted biphenyl-4-yl groups, suitable as Ar¹, include the following:
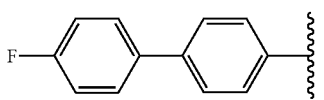
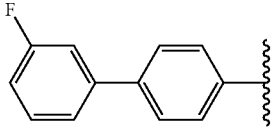
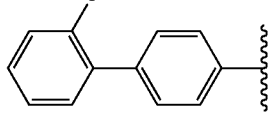
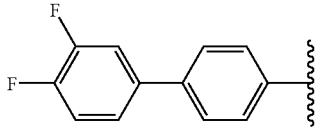
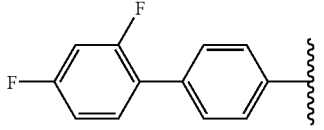
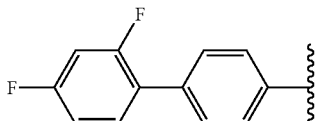
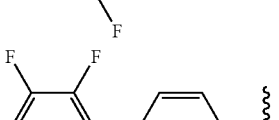
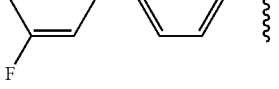
-continued
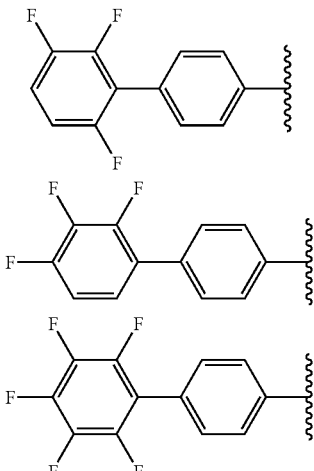
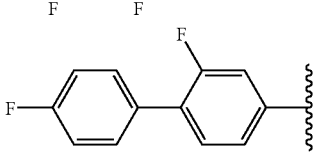
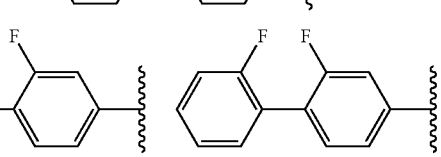
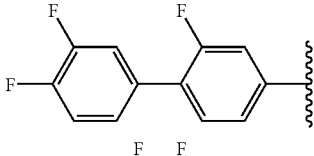
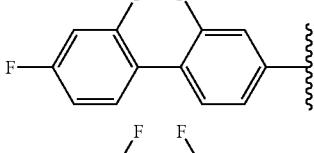
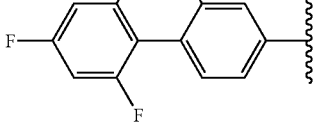
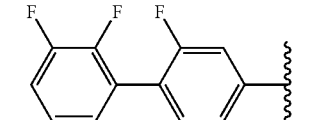
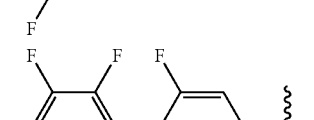
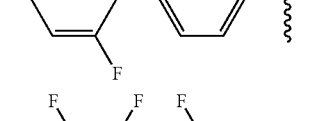

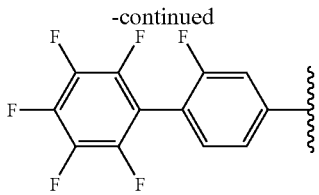

Additional examples of biphenyl-4-yl groups, suitable as Ar¹, appear in the "Examples of Specific Embodiments" below.

The Group R$^{alk}$

The alkylene group, R$^{alk}$, is a C$_{2-10}$alkylene group, and is optionally substituted.

The term "C$_{2-10}$alkylene," as used herein, pertains to a bidentate moiety obtained by removing two hydrogen atoms, either both from the same carbon atom, or one from each of two different carbon atoms, of a hydrocarbon compound having from 2 to 10 carbon atoms, which may be aliphatic or alicyclic, or a combination thereof, and which may be saturated, partially unsaturated, or fully unsaturated. The prefix (i.e., "C$_{2-10}$") denotes the number of carbon atoms in the moiety.

In one embodiment, R$^{alk}$ is C$_{3-10}$alkylene; C$_{4-10}$alkylene;

In one embodiment, R$^{alk}$ is C$_{2-8}$alkylene; C$_{3-4}$alkylene; C$_{4-8}$alkylene.

In one embodiment, R$^{alk}$ is C$_{2-7}$alkylene; C$_{3-7}$alkylene; C$_{4-7}$alkylene.

In one embodiment, R$^{alk}$ is C$_{2-6}$alkylene; C$_{3-4}$alkylene; C$_{4-6}$alkylene.

In one embodiment, R$^{alk}$ is C$_3$alkylene; C$_4$alkylene; C$_5$alkylene; C$_6$alkylene.

In one embodiment, R$^{alk}$ is an aliphatic group.
In one embodiment, R$^{alk}$ is a branched group.
In one embodiment, R$^{alk}$ is a linear group.
In one embodiment, R$^{alk}$ is a partially unsaturated aliphatic group.
In one embodiment, R$^{alk}$ is a fully saturated aliphatic group.
In one embodiment, R$^{alk}$ is a partially unsaturated branched group.

Examples of such groups include, but are not limited to, the following:

—C(Me)=CH—, —CH=C(Me)—, —C(Me)=C(Me)—,

—C(Et)=CH—, —CH=C(Et)-, —C(Et)=C(Et)-,

—C(Me)=CH—CH$_2$—, —CH=C(Me)-CH$_2$—, —CH=CH—CH(Me)—,

—C(Et)=CH—CH$_2$—, —CH=C(Et)-CH$_2$—, —CH=CH—CH(Et)-,

—C(Me)=CH—CH$_2$CH$_2$—, —CH=C(Me)-CH$_2$CH$_2$—, —CH=CH—CH(Me)CH$_2$—,

—C(Et)=CH—CH$_2$CH$_2$—, —CH=C(Et)-CH$_2$CH$_2$—, and —CH=CH—CH(Et)CH$_2$—.

In one embodiment, R$^{alk}$ is a fully saturated branched group.

Examples of such groups include, but are not limited to, the following:

—CH(Me)—, —CH(Et)-,

—CH(Me)CH$_2$—, —CH(Et)CH$_2$—, —CH$_2$CH(Me)—, —CH$_2$CH(Et)-,

—CH(Me)CH$_2$CH$_2$—, —CH$_2$CH(Me)CH$_2$, —CH$_2$CH$_2$CH(Me)—,

—CH(Et)CH$_2$CH$_2$—, —CH$_2$CH(Et)CH$_2$—, —CH$_2$CH$_2$CH(Et)-,

—CH(Me)CH$_2$CH$_2$CH$_2$—, —CH$_2$CH(Me)CH$_2$CHr,

—CH(Et)CH$_2$CH$_2$CH$_2$—, and —CH$_2$CH(Et)CH$_2$CH$_2$—.

In one embodiment, R$^{alk}$ is a partially unsaturated linear group.

Examples of such groups include, but are not limited to, the following:

—CH=CH— (vinylene),

—CH=CH—CH$_2$—, —CH$_2$—CH=CH—,

—CH=CH—CH$_2$—CH$_2$—, —CH$_2$—CH—CH=CH—, —CH=CH—CH=CH—, —CH=CH—CH$_2$—CH$_2$—CH$_2$—,

—CH=CH—CH=CH—CH$_2$—, —CH=CH—CH$_2$—CH=CH—, —CH=CH—CH=CH—CH$_2$—CH$_2$—, and

—CH=CH—CH$_2$—CH$_2$CH=CH—.

In one embodiment, R$^{alk}$ is a fully saturated linear group.

Examples of such groups include —(CH$_2$)$_2$— (ethylene), —(CH$_2$)$_3$— (propylene), —(CH$_2$)$_4$—, (butylene), —(CH$_2$)$_5$— (pentylene), —(CH$_2$)$_6$— (hexylene), —(CH$_2$)$_7$— (heptylene), —(CH$_2$)$_8$— (octylene), —(CH$_2$)$_9$— (nonylene), and —(CH$_2$)$_{10}$— (decylene).

In one embodiment, R$^{alk}$ is —(CH$_2$)$_n$— where n is an integer from 2 to 10.

In one embodiment, n is from 2 to 10; from 3 to 10; from 4 to 10.

In one embodiment, n is from 2 to 8; from 3 to 8; from 4 to 8.

In one embodiment, n is from 2 to 7; from 3 to 7; from 4 to 7.

In one embodiment, n is from 2 to 6; from 3 to 6; from 4 to 6.

In one embodiment, R$^{alk}$ is —(CH$_2$)$_4$— or —(CH$_2$)$_6$—.
In one embodiment, R$^{alk}$ is —(CH$_2$)$_3$—.
In one embodiment, R$^{alk}$ is —(CH$_2$)$_4$—.
In one embodiment, R$^{alk}$ is —(CH$_2$)$_5$—.
In one embodiment, R$^{alk}$ is —(CH$_2$)$_6$—.

In one embodiment, R$^{alk}$ is optionally substituted (i.e., unsubstituted or substituted).

In one embodiment, R$^{alk}$ is unsubstituted.
In one embodiment, R$^{alk}$ is substituted.
In one embodiment, R$^{alk}$ is optionally substituted with one or more substituents selected from: halogen, hydroxy, ether (e.g., C$_{1-7}$alkoxy), amino, and amido.

In one embodiment, R$^{alk}$ is optionally substituted with one or more substituents selected from: —F, —Cl, —Br, and —I.

In one embodiment, R$^{alk}$ is optionally substituted with one or more —F groups.

In one embodiment, R$^{alk}$ is:

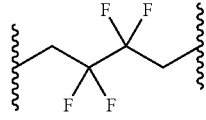

In one embodiment, one or more carbon atoms of the backbone chain of R$^{alk}$ is replaced with a moiety selected from: —O—, —S—, —S(=O), —S(=O)$_2$, and —NH—. In one embodiment, only one carbon atom is replaced.

In one embodiment, $R^{alk}$ is —$(CH_2)_n$— where n is an integer from 2 to 10; and one or more —$CH_2$— groups is replaced with a moiety selected from: —O—, —S—, —S(=O)—, —S(=O)$_2$, and —NH— (e.g., e.g., —$CH_2$—O—$CH_2$—). In one embodiment, only one —$CH_2$— group is replaced.

In one embodiment, the replaced carbon atom, or replaced —$CH_2$— group, is not at a terminal position within $R^{alk}$ (e.g., —$CH_2$—O—$CH_2$— but not —O—$CH_2$—$CH_2$— or —$CH_2$—$CH_2$—O—).

The Group Q: —OH or —$OR^{OT}$

In one embodiment, Q is independently —OH or —$OR^{OT}$.

In one embodiment, Q is independently —OH.

In one embodiment, the group —$OR^{OT}$, if present, is independently selected from:

—O—$R^{E1}$;

—O—C(=O)—$R^{E2}$;

—O—C(=O)—O—$R^{E3}$;

—O—C(=O)—O—$SO_3R^{E4}$;

—O—C(=O)—O—$(CH_2)_n$—$COOR^{E5}$;

—O—C(=O)—$(CH_2)_n$—$NR^{N1}R^{N2}$;

—O—C(=O)—$(CH_2)_n$—NH—C(=O)$R^{E1}$;

—O—C(=O)—$(CH_2)_n$—C(=O)—$NR^{N3}R^{N4}$;

—O—P(=O)($OR^{E7}$)($OR^{E8}$);

—O—$R^{PA}$;

wherein:

each of $R^{E1}$, $R^{E2}$, $R^{E3}$, $R^{E4}$, $R^{E5}$, $R^{E6}$, $R^{E7}$, and $R^{E8}$ is independently as defined in (20), (21), (22) or (23) above; and each of $R^{E2}$, $R^{E4}$, $R^{E5}$, $R^{E7}$, and $R^{E6}$ may additionally be —H; and each of —$NR^{N1}R^{N2}$ and —$NR^{N3}R^{N4}$ is independently as defined for —$NR^8R^9$.

In one embodiment:

each of $R^{E1}$, $R^{E2}$, $R^{E3}$, $R^{E4}$, $R^{E5}$, $R^{E6}$, $R^{E7}$, and $R^{E8}$ is independently as defined in (23) above; and each of $R^{E2}$, $R^{E4}$, $R^{E5}$, $R^{E7}$ and $R^{E8}$ may additionally be —H; and each of —$NR^{N1}R^{N2}$ and —$NR^{N3}R^{N4}$ is independently as defined for —$NR^5R^9$.

In one embodiment, the group —$OR^{OT}$, if present, is as defined above, but with the further proviso that if —$OR^{OT}$ is —O—$R^{E1}$, then $R^{E1}$ is not a phenyl group substituted with a sulfonyl group (—$SO_2R$).

In one embodiment, the group —$OR^{OT}$, if present, is as defined above, but with the further proviso that —$OR^{OT}$ is not an aryl ether (e.g., is not aryloxy).

In one embodiment, the group —$OR^{OT}$, if present, is as defined above, but with the further proviso that —$OR^{OT}$ is not —O—$R^{E1}$.

The Group Q: Other Groups

In one embodiment, Q is independently selected from:

—H;

—C(=O)—OH;

—C(=O)—$R^{F1}$;

—NH—C(=O)—$R^{F2}$;

—NH—C(=O)—$NR^{N5}R^{N6}$;

—NH—C(=S)—$NR^{N7}R^{N8}$;

—NH—C(=NH)—$NR^{N9}R^{N10}$;

—NH—S(=O)$_2R^{F3}$;

—NH—C(=NH)—$R^{F4}$;

—NH—C(=NH)—S—$R^{F5}$;

—NH—CN;

—S—C(=NH)—$R^{F6}$;

—S—C(=NH)—S—$R^{F7}$;

—S—C(=NH)—$NR^{N11}R^{N12}$;

—C(CN)$_2$;

—P(=O)($OR^{F8}$)($OR^{F9}$);

—$R^{PA}$;

wherein:

each of $R^{F1}$, $R^{F2}$, $R^{F3}$, $R^{F4}$, $R^{F5}$, $R^{F6}$, $R^{F7}$, $R^{F8}$, and $R^{F9}$ is independently as defined in (20), (21), (22) or (23) above; and each of $R^{F4}$, $R^{F5}$, $R^{F6}$, $R^{F7}$, $R^{F8}$ and $R^{F9}$ may additionally be —H; and each of $NR^{N5}R^{N6}$, —$NR^{N7}R^{N8}$, $NR^{N9}RN^{10}$ and —$NR^{N11}R^{N12}$ is independently as defined for —$NR^8R^9$.

The Group $R^{PA}$

The group $R^{PA}$, if present, is an organic group incorporating a phosphonic acid group.

Without wishing to be bound by any particular theory, it is believed that phosphonic acid groups act as bone targeting moieties, and improve delivery of the compound to the bone environment.

Examples of bisphosphonate compounds currently in use for the treatment of osteoporosis, Paget's disease, and cancer associated bone disease include the following:

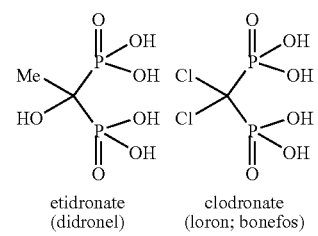

etidronate (didronel)   clodronate (loron; bonefos)

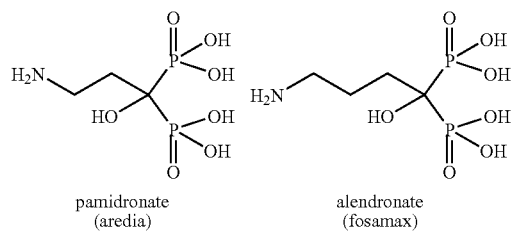

pamidronate (aredia)   alendronate (fosamax)

-continued

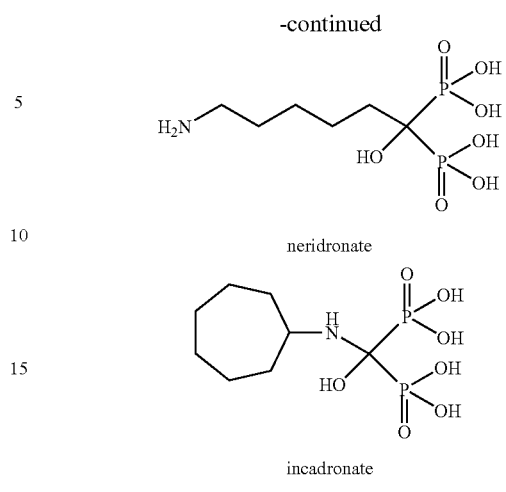

neridronate incadronate

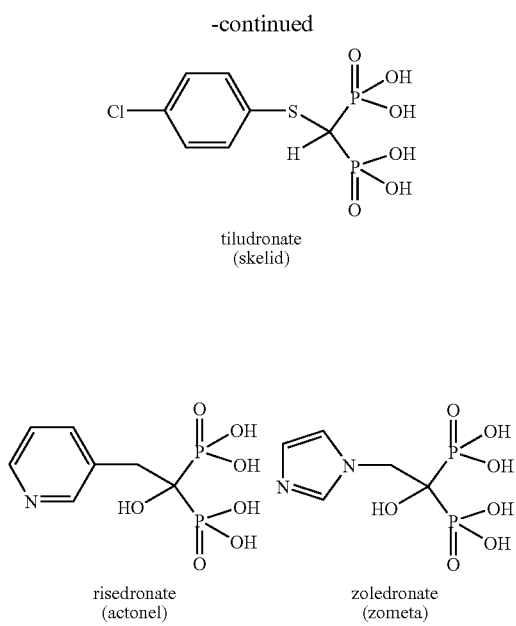

tiludronate
(skelid)

risedronate
(actonel)

zoledronate
(zometa)

Examples of bisphosphonate compounds currently in development include the following:

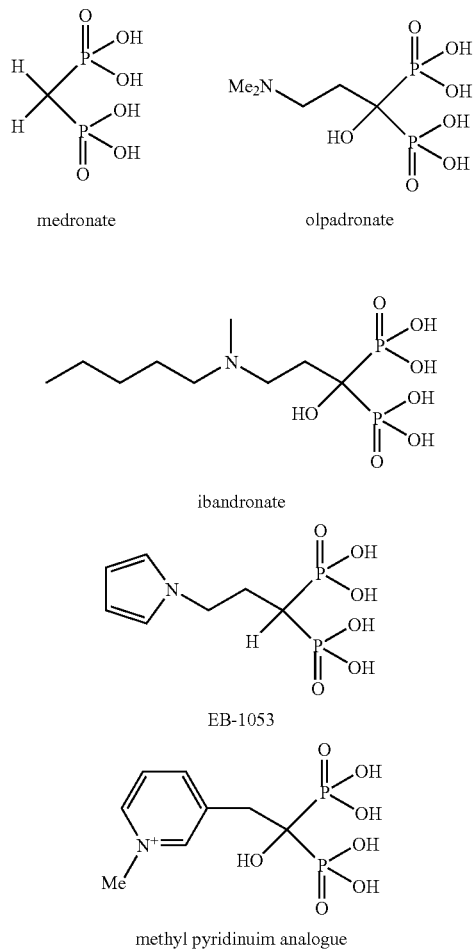

medronate olpadronate ibandronate

EB-1053 methyl pyridinuim analogue

In one embodiment, Q is independently —$R^{PA}$ or —$OR^{PA}$, wherein $R^{PA}$ is an organic group incorporating a phosphonic acid group.

The term "phosphonic acid group," as used herein, pertains to phosphonic acid, and groups derived therefrom, for example: phosphonic acid, and salts (e.g. phosphonates) and esters (e.g., phosphonate esters) thereof.

Examples of such groups are shown below. For the phosphonate esters, the groups $R^1$ and $R^2$ are independently $C_{1-7}$alkyl, $C_{3-20}$heterocyclyl, or $C_{5-20}$aryl, preferably $C_{1-7}$alkyl, e.g., ethyl.

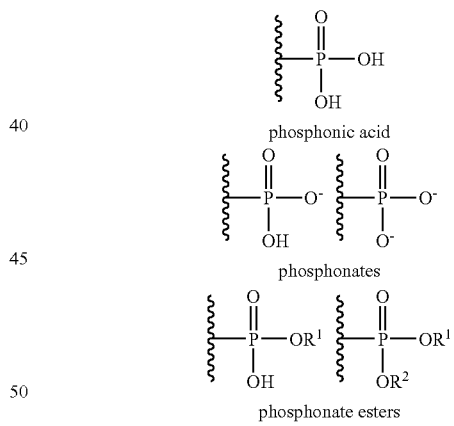

phosphonic acid phosphonates phosphonate esters

Where the group is a phosphonate bearing a charge of (−1) or (−2), it will be associated with a suitable number of cation or cations of suitable charge. Examples of suitable cations are discussed below.

In one embodiment, $R^{PA}$, if present, is an organic group (i.e., a group comprising at least carbon and hydrogen) having from 5 to 40 atoms, preferably from 5 to 30 atoms, preferably from 5 to 20 atoms, selected from carbon, nitrogen, oxygen, sulfur, phosphorus, fluorine, chloride, bromine, and iodine (and excluding hydrogen), preferably selected from carbon, nitrogen, oxygen, sulfur, and phosphorus, preferably selected from carbon, oxygen, and phosphorus; and incorporates a phosphonic acid group.

In one embodiment, $R^{PA}$, if present, independently incorporates one phosphonic acid group.

In one embodiment, $R^{PA}$, if present, independently incorporates two phosphonic acid groups.

In one embodiment, $R^{PA}$, if present, independently incorporates the following group, or a salt or ester thereof:

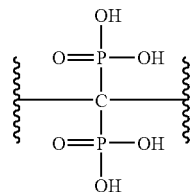

In one embodiment, $R^{PA}$, if present, is the following group, or a salt or ester thereof:

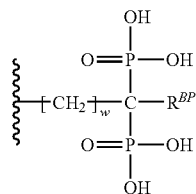

wherein:

w is an integer from 0 to 5; and $R^{BP}$ is —H, —OH, halo, or $C_{1-7}$alkyl (e.g., as defined in (23) above).

In one embodiment, w is an integer from 0 to 3.

In one embodiment, w is 0, 1, or 2.

In one embodiment, $R^{BP}$ is —H. For example (here the group $R^{PA}$ has 9, 10, and 11 atoms, respectively, selected from carbon, oxygen, and phosphorus):

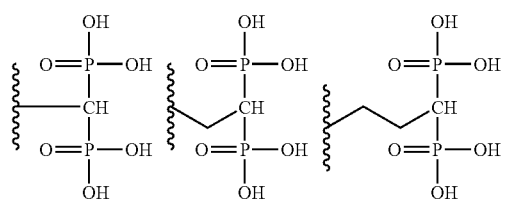

In one embodiment, $R^{BP}$ is —OH. For example (here the group $R^{PA}$ has 12 atoms selected from carbon, oxygen, and phosphorus):

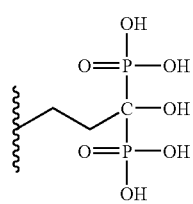

In one embodiment, $R^{BP}$ is —CH$_2$CH$_2$COOH. For example (here the group $R^{PA}$ has 16 atoms selected from carbon, oxygen, and phosphorus):

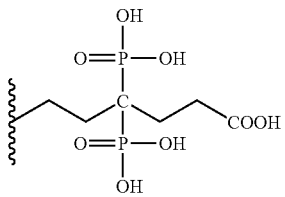

The Group $R^O$

In one embodiment, —OR$^O$, if present, is independently —OH or a protected hydroxy group (e.g., a prodrug).

In one embodiment, —OR$^O$, if present, is other than siloxy.

In one embodiment, —OR$^O$, if present, is independently —OH or OR$^K$.

In one embodiment, —OR$^O$, if present, is independently —OH.

In one embodiment, the group —OR$^K$, if present, is independently selected from:

—O—R$^{K1}$;

—O—C(=O)R$^{K2}$;

—O—C(=O)OR$^{K3}$;

—O—S(=O)$_2$OR$^{K4}$;

wherein:

each of R$^{K1}$, R$^{K2}$, R$^{K3}$, and R$^{K4}$ is independently as defined in (20), (21), (22) or (23) above; and each of R$^{K3}$ and R$^{K4}$ may additionally be —H.

In one embodiment:

each of R$^{K1}$, R$^{K2}$, R$^{K3}$, and R$^{K4}$ is independently as defined in (23) above; and each of R$^{K3}$ and R$^{K4}$ may additionally be —H.

Protected Ketones

In one embodiment, the carbonyl group in formula (1) is present in a protected form (e.g., as a prodrug).

In one embodiment, the carbonyl group (—C(=O)—) in formula (1) is replaced with a group selected from the following, wherein each R is independently as defined in (20), (21), (22) or (23) above:

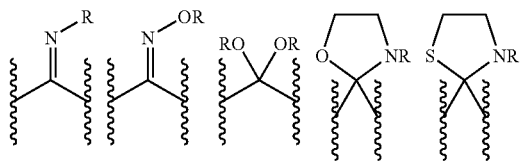

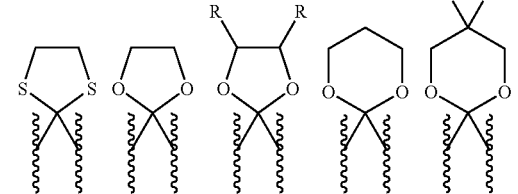

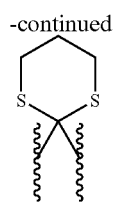
Examples of Specific Embodiments
Some individual embodiments of the present invention include the following compounds (e.g., "ketones" with Q as —OH or —OR$^{OT}$).
ABD-68
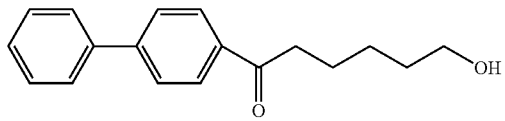
ABD-81
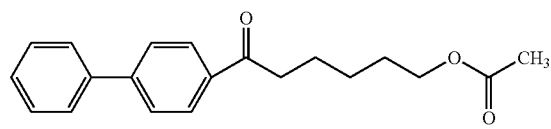
ABD-227
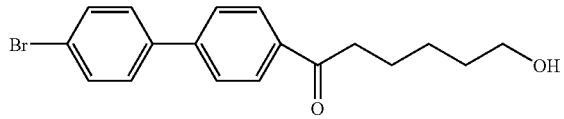
ABD-228
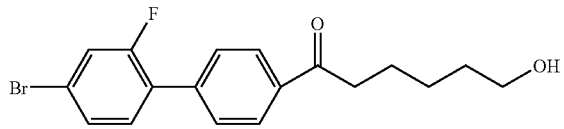
ABD240
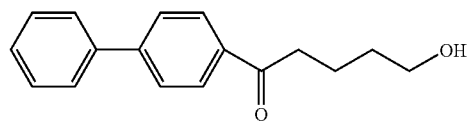
ABD-241
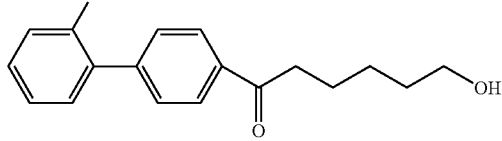
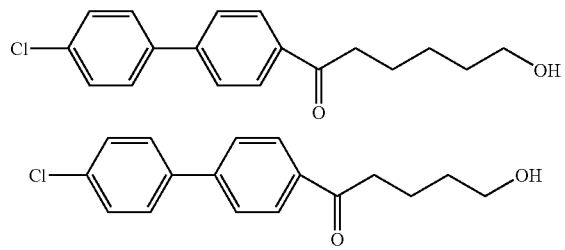
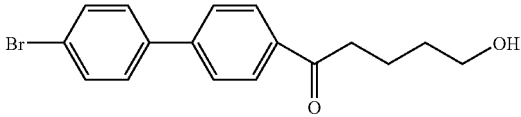
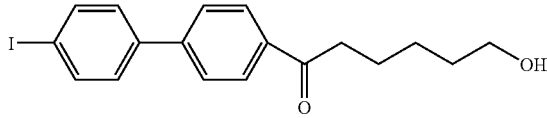
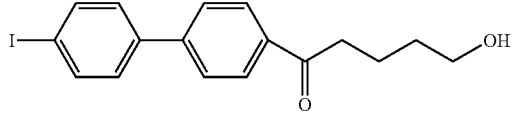
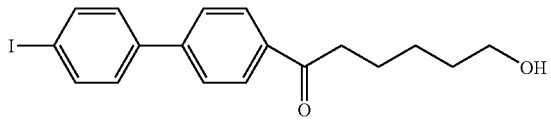
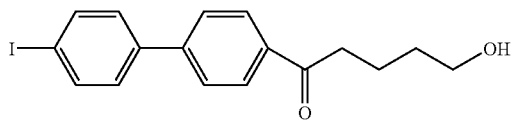
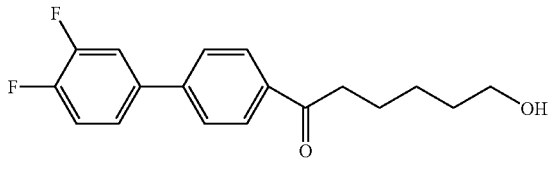
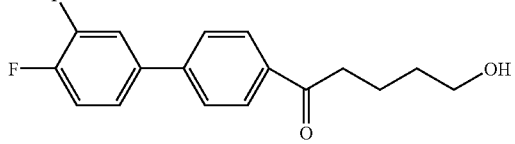
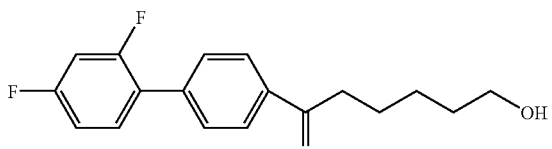
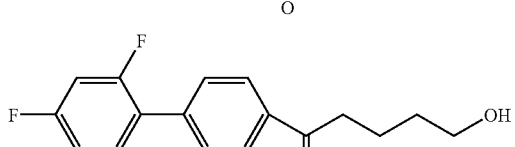
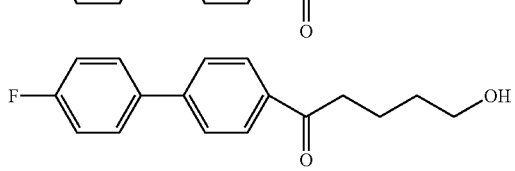

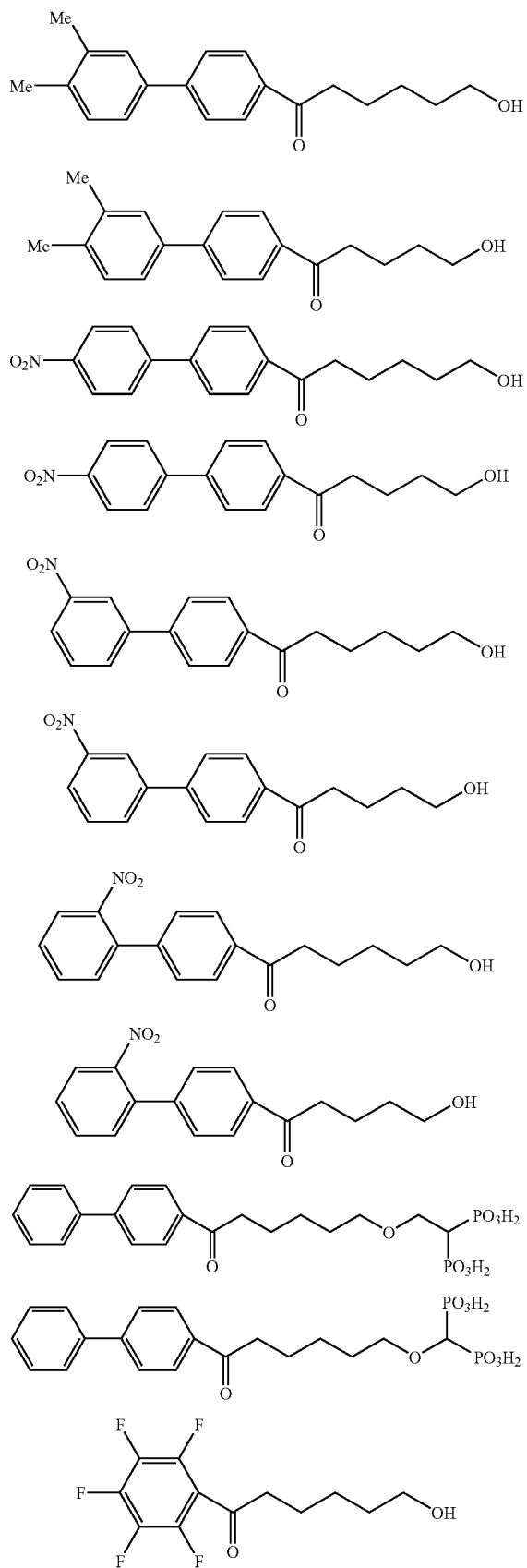
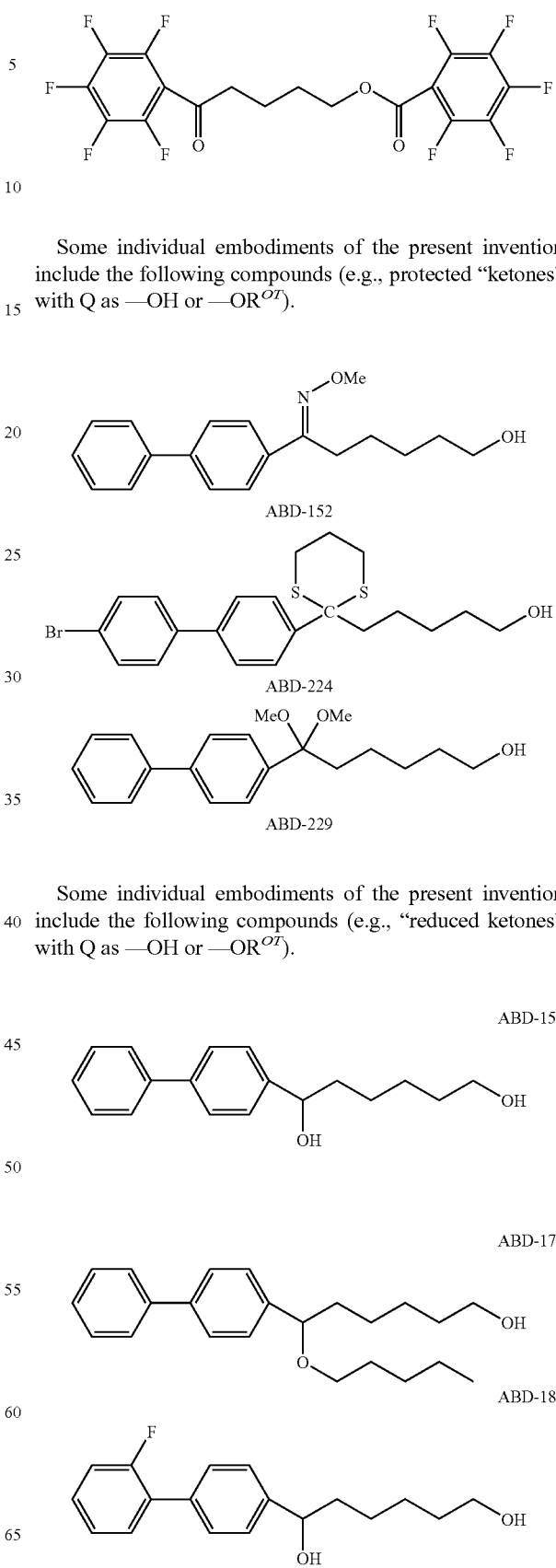
Some individual embodiments of the present invention include the following compounds (e.g., protected "ketones" with Q as —OH or —OR$^{OT}$).
Some individual embodiments of the present invention include the following compounds (e.g., "reduced ketones" with Q as —OH or —OR$^{OT}$).

ABD-191
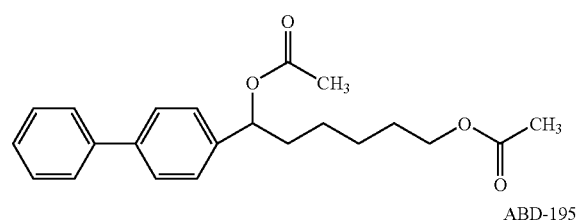
ABD-195
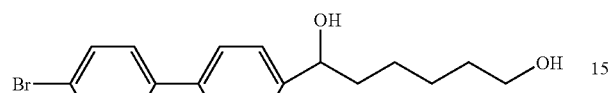
ABD-217
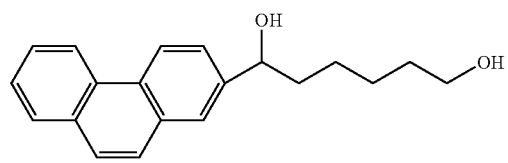
ABD-220
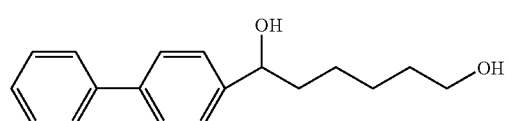
ABD-235
ABD-236
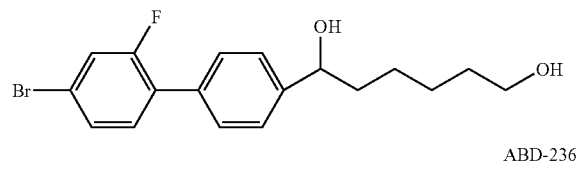
ABD-237
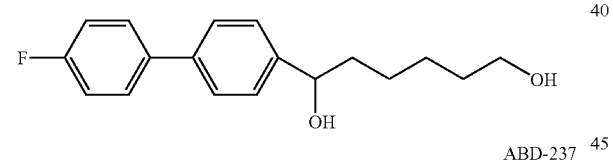
ABD-239
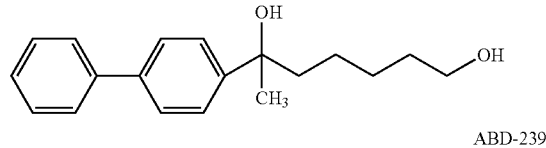
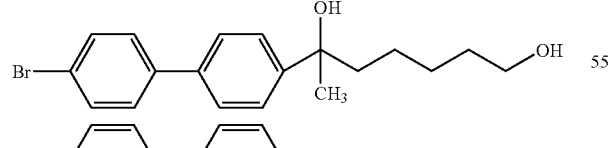
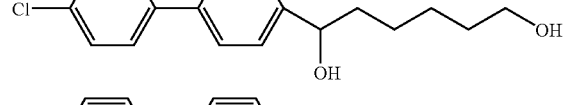
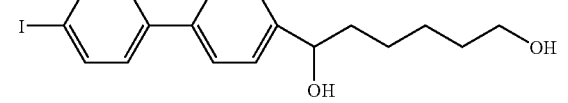
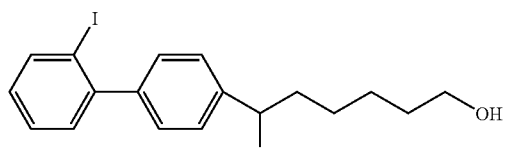
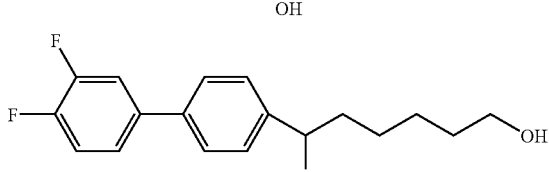
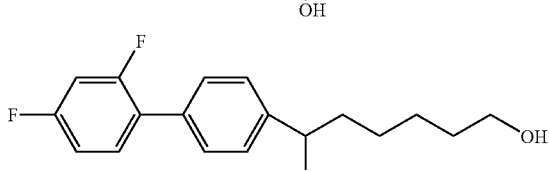
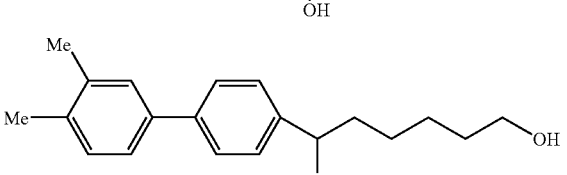
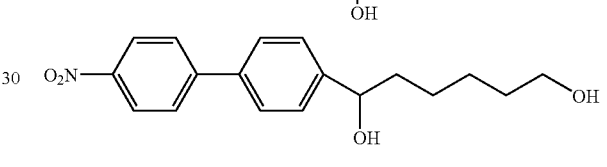
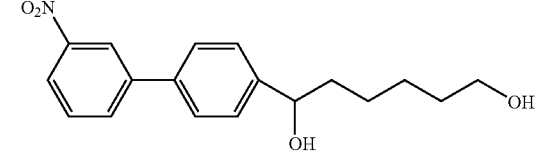
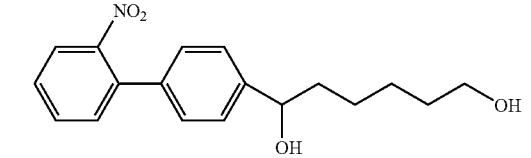
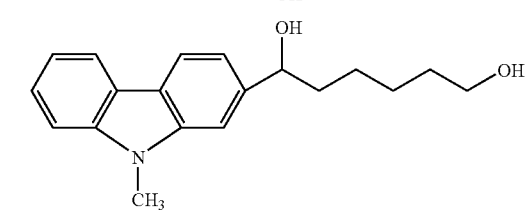
Some individual embodiments of the present invention include the following compounds (e.g., "ketones" with other Q groups).
ABD-133
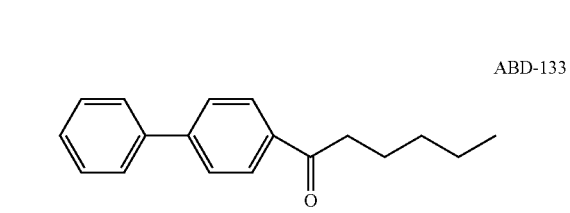

-continued

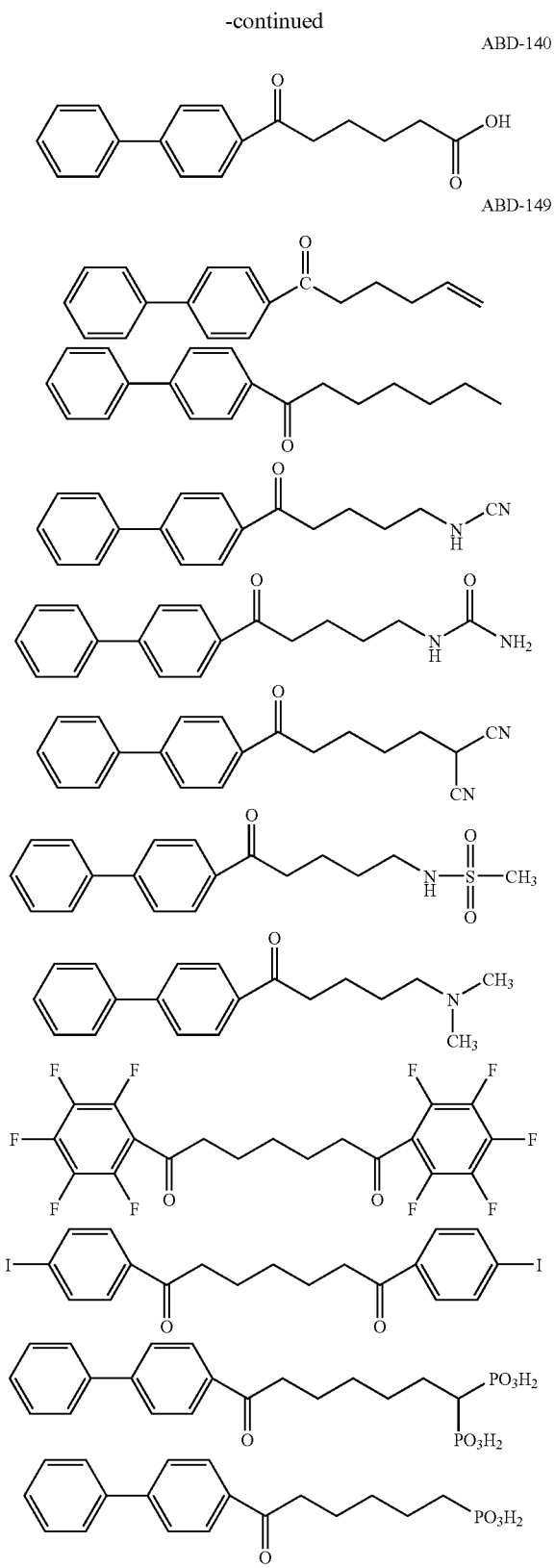

Some individual embodiments of the present invention include the following compounds (e.g., "reduced ketones" with other Q groups).

Chemical Terms

The term "carbo," "carbyl," "hydrocarbon" and "hydrocarbyl," as used herein, pertain to compounds and/or groups which have only carbon and hydrogen atoms (but see "carbocyclic" below).

The term "hetero," as used herein, pertains to compounds and/or groups which have at least one heteroatom, for example, multivalent heteroatoms (which are also suitable as ring heteroatoms) such as boron, silicon, nitrogen, phosphorus, oxygen, sulfur, and selenium (more commonly nitrogen, oxygen, and sulfur) and monovalent heteroatoms, such as fluorine, chlorine, bromine, and iodine.

The term "saturated," as used herein, pertains to compounds and/or groups which do not have any carbon-carbon double bonds or carbon-carbon triple bonds.

The term "unsaturated," as used herein, pertains to compounds and/or groups which have at least one carbon-carbon double bond or carbon-carbon triple bond.

The term "aliphatic," as used herein, pertains to compounds and/or groups which are linear or branched, but not cyclic (also known as "acyclic" or "open-chain" groups).

The term "ring," as used herein, pertains to a closed ring of from 3 to 10 covalently linked atoms, more preferably 3 to 8 covalently linked atoms, yet more preferably 5 to 6 covalently linked atoms. A ring may be an alicyclic ring or an aromatic ring. The term "alicyclic ring," as used herein, pertains to a ring which is not an aromatic ring.

The term "carbocyclic ring," as used herein, pertains to a ring wherein all of the ring atoms are carbon atoms.

The term "heterocyclic ring," as used herein, pertains to a ring wherein at least one of the ring atoms is a multivalent ring heteroatom, for example, nitrogen, phosphorus, silicon, oxygen, or sulfur, though more commonly nitrogen, oxygen, or sulfur. Preferably, the heterocyclic ring has from 1 to 4 heteroatoms.

The term "cyclic compound," as used herein, pertains to a compound which has at least one ring. The term "cyclyl," as used herein, pertains to a monovalent moiety obtained by removing a hydrogen atom from a ring atom of a cyclic compound.

Where a cyclic compound has two or more rings, they may be fused (e.g., as in naphthalene), bridged (e.g., as in norbornane), spiro (e.g., as in spiro[3.3]heptane), or a combination thereof. Cyclic compounds with one ring may be referred to as "monocyclic" or "mononuclear," whereas cyclic compounds with two or more rings may be referred to as "polycyclic" or "polynuclear."

The term "carbocyclic compound," as used herein, pertains to a cyclic compound which has only carbocyclic ring(s).

The term "heterocyclic compound," as used herein, pertains to a cyclic compound which has at least one heterocyclic ring.

The term "aromatic compound," as used herein, pertains to a cyclic compound which has at least one aromatic ring.

The term "carboaromatic compound," as used herein, pertains to a cyclic compound which has only carboaromatic ring(s).

The term "heteroaromatic compound," as used herein, pertains to a cyclic compound which has at least one heteroaromatic ring.

The term "monodentate substituents," as used herein, pertains to substituents which have one point of covalent attachment.

The term "monovalent monodentate substituents," as used herein, pertains to substituents which have one point of covalent attachment, via a single bond. Examples of such substituents include halo, hydroxy, and alkyl.

The term "multivalent monodentate substituents," as used herein, pertains to substituents which have one point of covalent attachment, but through a double bond or triple bond. Examples of such substituents include oxo, imino, alkylidene, and alklidyne.

The term "bidentate substituents," as used herein, pertains to substituents which have two points of covalent attachment, and which act as a linking group between two other moieties. Examples of such substituents include alkylene and arylene.

Substituents

The phrase "optionally substituted," as used herein, pertains to a parent group which may be unsubstituted or which may be substituted.

Unless otherwise specified, the term "substituted," as used herein, pertains to a parent group which bears one or more substitutents. The term "substituent" is used herein in the conventional sense and refers to a chemical moiety which is covalently attached to, appended to, or if appropriate, fused to, a parent group. A wide variety of substituents are well known, and methods for their formation and introduction into a variety of parent groups are also well known.

The substituents are described in more detail below.

Alkyl: The term "alkyl," as used herein, pertains to a monovalent moiety obtained by removing a hydrogen atom from a carbon atom of a hydrocarbon compound having from 1 to 20 carbon atoms (unless otherwise specified), which may be aliphatic or alicyclic, and which may be saturated, partially unsaturated, or fully unsaturated. Thus, the term "alkyl" includes the sub-classes alkenyl, alkynyl, cycloalkyl, etc., discussed below.

In this context, the prefixes (e.g., $C_{1-4}$, $C_{1-7}$, $C_{1-20}$, $C_{2-7}$, $C_{3-7}$, etc.) denote the number of carbon atoms, or range of number of carbon atoms. For example, the term "$C_{1-4}$alkyl," as used herein, pertains to an alkyl group having from 1 to 4 carbon atoms. Examples of groups of alkyl groups include $C_{1-4}$alkyl ("lower alkyl"), $C_{1-7}$alkyl, and $C_{1-20}$alkyl.

Examples of (unsubstituted) saturated alkyl groups include, but are not limited to, methyl ($C_1$), ethyl ($C_2$), propyl ($C_3$), butyl ($C_4$), pentyl ($C_5$), hexyl ($C_6$), heptyl ($C_7$), octyl ($C_8$), nonyl ($C_9$), decyl ($C_{10}$), n-undecyl ($C_{11}$), dodecyl ($C_{12}$), tridecyl ($C_{13}$), tetradecyl ($C_{14}$), pentadecyl ($C_{15}$), and eicodecyl ($C_{20}$).

Examples of (unsubstituted) saturated linear alkyl groups include, but are not limited to, methyl ($C_1$), ethyl ($C_2$), n-propyl ($C_3$), n-butyl ($C_4$), n-pentyl (amyl) ($C_5$), n-hexyl ($C_6$), and n-heptyl ($C_7$).

Examples of (unsubstituted) saturated branched alkyl groups include iso-propyl ($C_3$), iso-butyl ($C_4$), sec-butyl ($C_4$), tert-butyl ($C_4$), isopentyl ($C_5$), and neo-pentyl ($C_5$).

Cycloalkyl: The term "cycloalkyl," as used herein, pertains to an alkyl group which is also a cyclyl group; that is, a monovalent moiety obtained by removing a hydrogen atom from an alicyclic ring atom of a cyclic hydrocarbon (carbocyclic) compound, which moiety has from 3 to 20 ring atoms (unless otherwise specified). Preferably, each ring has from 3 to 7 ring atoms.

Examples of (unsubstituted) saturated cylcoalkyl groups include, but are not limited to, those derived from: cyclopropane ($C_3$), cyclobutane ($C_4$), cyclopentane ($C_5$), cyclohexane ($C_8$), cycloheptane ($C_7$), norbornane ($C_7$), norpinane ($C_7$), adamantane ($C_{10}$), and decalin (decahydronaphthalene) ($C_{10}$).

Examples of (substituted) saturated cycloalkyl groups, which are also referred to herein as "alkyl-cycloalkyl" groups, include, but are not limited to, methylcyclopropyl, dimethylcyclopropyl, methylcyclobutyl, dimethylcyclobutyl, methylcyclopentyl, dimethylcyclopentyl, methylcyclohexyl, and dimethylcyclohexyl.

Examples of (substituted) unsaturated cyclic alkenyl groups, which are also referred to herein as "alkyl-cycloalkenyl" groups, include, but are not limited to, methylcyclopropenyl, dimethylcyclopropenyl, methylcyclobutenyl, dimethylcyclobutenyl, methylcyclopentenyl, dimethylcyclopentenyl, methylcyclohexenyl, and dimethylcyclohexenyl.

Examples of (substituted) cycloalkyl groups, with one or more other rings fused to the parent cycloalkyl group, include, but are not limited to, those derived from: indene ($C_9$), indan (e.g., 2,3-dihydro-1H-indene) ($C_9$), tetraline (1,2,3,4-tetrahydronaphthalene ($C_{10}$), fluorene ($C_{13}$), phenalene ($C_{13}$). For example, 2H-inden-2-yl is a $C_5$cycloalkyl group with a substituent (phenyl) fused thereto.

Alkenyl: The term "alkenyl," as used herein, pertains to an alkyl group having one or more carbon-carbon double bonds. Examples of groups of alkenyl groups include $C_{2-4}$alkenyl, $C_{2-7}$alkenyl, $C_{2-20}$alkenyl.

Examples of (unsubstituted) unsaturated alkenyl groups include, but are not limited to, ethenyl (vinyl, —CH=CH$_2$), 1-propenyl (—CH=CH—CH$_3$), 2-propenyl (allyl, —CH—CH=CH$_2$), isopropenyl (—C(CH$_3$)=CH$_2$), butenyl ($C_4$), pentenyl ($C_5$), and hexenyl ($C_6$).

Examples of (unsubstituted) unsaturated cyclic alkenyl groups, which are also referred to herein as "cycloalkenyl" groups, include, but are not limited to, cyclopropenyl ($C_3$), cyclobutenyl ($C_4$), cyclopentenyl ($C_5$), and cyclohexenyl (Ce).

Alkynyl: The term "alkynyl," as used herein, pertains to an alkyl group having one or more carbon-carbon triple bonds. Examples of groups of alkynyl groups include $C_{2-4}$alkynyl, $C_{2-7}$alkynyl, $C_{2-20}$alkynyl.

Examples of (unsubstituted) unsaturated alkynyl groups include, but are not limited to, ethynyl (ethinyl, —C≡CH) and 2-propynyl (propargyl, —CH₂—C≡CH).

Alkylidene: The term "alkylidene," as used herein, pertains to a divalent monodentate moiety obtained by removing two hydrogen atoms from a carbon atom of a hydrocarbon compound having from 1 to 20 carbon atoms (unless otherwise specified), which may be aliphatic or alicyclic, or a combination thereof, and which may be saturated, partially unsaturated, or fully unsaturated. Examples of groups of alkylidene groups include $C_{1-4}$alkylidene, $C_{1-7}$alkylidene, $C_{1-20}$alkylidene.

Examples of alkylidene groups include, but are not limited to, methylidene (=CH₂), ethylidene (=CH—CH₃), vinylidene (=C=CH₂), and isopropylidene (=C(CH₃)₂).

Alkylidyne: The term "alkylidyne," as used herein, pertains to a trivalent monodentate moiety obtained by removing three hydrogen atoms from a carbon atom of a hydrocarbon compound having from 1 to 20 carbon atoms (unless otherwise specified), which may be aliphatic or alicyclic, or a combination thereof, and which may be saturated, partially unsaturated, or fully unsaturated. Examples of groups of alkylidyne groups include $C_{1-4}$alkylidyne, $C_{1-7}$alkylidyne, $C_{1-20}$alkylidyne.

Examples of alkylidyne groups include, but are not limited to, methylidyne (≡CH) and ethylidyne (≡C—CH₃).

Carbocyclyl: The term "carbocyclyl," as used herein, pertains to a monovalent moiety obtained by removing a hydrogen atom from a ring atom of a carbocyclic compound, which moiety has from 3 to 20 ring atoms (unless otherwise specified). Preferably, each ring has from 3 to 7 ring atoms.

In this context, the prefixes (e.g., $C_{3-20}$, $C_{3-7}$, $C_{5-8}$, etc.) denote the number of ring atoms, or range of number of ring atoms. For example, the term "$C_{5-6}$carbocyclyl," as used herein, pertains to a carbocyclyl group having 5 or 6 ring atoms. Examples of groups of carbocyclyl groups include $C_{3-20}$carbocyclyl, $C_{3-10}$-carbocyclyl, $C_{5-10}$-carbocyclyl, $C_{3-7}$carbocyclyl, and $C_{5-7}$carbocyclyl.

Examples of carbocyclic groups include, but are not limited to, those described above as cycloalkyl groups; those described below as carboaryl groups.

Heterocyclyl: The term "heterocyclyl," as used herein, pertains to a monovalent moiety obtained by removing a hydrogen atom from a ring atom of a heterocyclic compound, which moiety has from 3 to 20 ring atoms (unless otherwise specified), of which from 1 to 10 are ring heteroatoms. Preferably, each ring has from 3 to 7 ring atoms, of which from 1 to 4 are ring heteroatoms.

In this context, the prefixes (e.g., $C_{3-20}$, $C_{3-7}$, $C_{5-6}$, etc.) denote the number of ring atoms, or range of number of ring atoms, whether carbon atoms or heteroatoms. For example, the term "$C_{5-6}$heterocyclyl," as used herein, pertains to a heterocyclyl group having 5 or 6 ring atoms. Examples of groups of heterocyclyl groups include $C_{3-20}$heterocyclyl, $C_{3-7}$heterocyclyl, $C_{5-7}$heterocyclyl.

Examples of (non-aromatic) monocyclic heterocyclyl groups include, but are not limited to, those derived from:

$N_1$: aziridine ($C_3$), azetidine ($C_4$), pyrrolidine (tetrahydropyrrole) ($C_5$), pyrroline (e.g., 3-pyrroline, 2,5-dihydropyrrole) ($C_5$), 2H-pyrrole or 3H-pyrrole (isopyrrole, isoazole) ($C_5$), piperidine ($C_6$), dihydropyridine ($C_6$), tetrahydropyridine ($C_6$), azepine ($C_7$);

$O_1$: oxirane ($C_3$), oxetane ($C_4$), oxolane (tetrahydrofuran) ($C_5$), oxole (dihydrofuran) ($C_5$), oxane (tetrahydropyran) ($C_6$), dihydropyran ($C_6$), pyran ($C_6$), oxepin ($C_7$);

$S_1$: thiirane ($C_3$), thietane ($C_4$), thiolane (tetrahydrothiophene) ($C_5$), thiane (tetrahydrothiopyran) ($C_6$), thiepane ($C_7$);

$O_2$: dioxolane ($C_5$), dioxane ($C_6$), and dioxepane ($C_7$);

$O_3$: trioxane ($C_6$);

$N_2$: imidazolidine ($C_5$), pyrazolidine (diazolidine) ($C_5$), imidazoline ($C_5$), pyrazoline (dihydropyrazole) ($C_5$), piperazine ($C_6$);

$N_1O_1$: tetrahydrooxazole ($C_5$), dihydrooxazole ($C_5$), tetrahydroisoxazole ($C_5$), dihydroisoxazole ($C_5$), morpholine ($C_6$), tetrahydrooxazine (CO), dihydrooxazine ($C_6$), oxazine ($C_6$);

$N_2S_1$: thiazoline ($C_5$), thiazolidine ($C_5$), thiomorpholine ($C_6$);

$N_2O_1$: oxadiazine ($C_6$);

$O_1S_1$: oxathiole ($C_5$) and oxathiane (thioxane) ($C_6$); and, $N_1O_1S_1$: oxathiazine ($C_6$).

Examples of substituted (non-aromatic) monocyclic heterocyclyl groups include saccharides, in cyclic form, for example, furanoses ($C_5$), such as arabinofuranose, lyxofuranose, ribofuranose, and xylofuranse, and pyranoses ($C_6$), such as allopyranose, altropyranose, glucopyranose, mannopyranose, gulopyranose, idopyranose, galactopyranose, and talopyranose.

Examples of heterocyclyl groups which are also heteroaryl groups are described below with aryl groups.

Aryl: The term "aryl," as used herein, pertains to a monovalent moiety obtained by removing a hydrogen atom from an aromatic ring atom of an aromatic compound, which moiety has from 3 to 20 ring atoms (unless otherwise specified). Preferably, each ring has from 5 to 7 ring atoms.

In this context, the prefixes (e.g., $C_{3-20}$, $C_{5-7}$, $C_{5-6}$, etc.) denote the number of ring atoms, or range of number of ring atoms, whether carbon atoms or heteroatoms. For example, the term "$C_{5-6}$aryl," as used herein, pertains to an aryl group having 5 or 6 ring atoms. Examples of groups of aryl groups include $C_{3-20}$aryl, $C_{3-12}$aryl, $C_{3-12}$aryl, $C_{5-7}$aryl, and $C_{5-6}$aryl.

The ring atoms may be all carbon atoms, as in "carboaryl groups" (e.g., $C_{5-20}$carboaryl).

Examples of carboaryl groups include, but are not limited to, those derived from benzene (i.e., phenyl) ($C_6$), naphthalene ($C_{10}$), azulene ($C_{10}$), anthracene ($C_{14}$), phenanthrene ($C_{14}$), naphthacene ($C_{18}$), and pyrene ($C_{16}$).

Examples of aryl groups which comprise fused rings, at least one of which is an aromatic ring, include, but are not limited to, groups derived from indene ($C_9$), isoindene ($C_9$), and fluorene ($C_{13}$).

Alternatively, the ring atoms may include one or more heteroatoms, as in "heteroaryl groups" (e.g., $C_{5-20}$heteroaryl).

Examples of monocyclic heteroaryl groups include, but are not limited to, those derived from:

$N_1$: pyrrole (azole) ($C_5$), pyridine (azine) ($C_6$);

$O_1$: furan (oxole) ($C_5$);

$S_1$: thiophene (thiole) ($C_5$);

$N_1O_1$: oxazole ($C_5$), isoxazole ($C_5$), isoxazine ($C_6$);

$N_2O_1$: oxadiazole (furazan) ($C_5$);

$N_3O_1$: oxatriazole ($C_5$);

$N_1S_1$: thiazole ($C_5$), isothiazole ($C_5$);

$N_2$: imidazole (1,3-diazole) ($C_5$), pyrazole (1,2-diazole) ($C_5$), pyridazine (1,2-diazine) ($C_6$), pyrimidine (1,3-diazine) ($C_6$) (e.g., cytosine, thymine, uracil), pyrazine (1,4-diazine) ($C_6$);

$N_3$: triazole ($C_5$), triazine ($C_6$); and, $N_4$: tetrazole ($C_5$).

Examples of heterocyclic groups (some of which are also heteroaryl groups) which comprise fused rings, include, but are not limited to:

$C_9$heterocyclic groups (with 2 fused rings) derived from benzofuran ($O_1$), isobenzofuran ($O_1$), indole ($N_1$), isoindole ($N_1$), purine ($N_4$) (e.g., adenine, guanine), benzimidazole (N2), benzoxazole ($N_1O_1$), benzisoxazole ($N_1O_1$), benzodioxole ($O_2$), benzofurazan ($N_2O_1$), benzotriazole ($N_3$), benzothiofuran (S1), benzothiazole ($N_1S_1$), benzothiadiazole ($N_2S$);

$C_{10}$heterocyclic groups (with 2 fused rings) derived from benzodioxan ($O_2$), quinoline ($N_1$), isoquinoline ($N_1$), benzoxazine ($N_1O_1$), benzodiazine ($N_2$), pyridopyridine ($N_2$), quinoxaline ($N_2$), quinazoline ($N_2$), phthalazine ($N_2$), pteridine ($N_4$);

$C_{13}$heterocyclic groups (with 3 fused rings) derived from carbazole ($N_1$), dibenzofuran ($O_1$), dibenzothiophene ($S_1$); and, $C_{14}$heterocyclic groups (with 3 fused rings) derived from acridine ($N_1$), xanthene ($O_1$), phenoxathiin ($O_1S_1$), phenazine ($N_2$), phenoxazine ($N_1O_1$), phenothiazine ($N_1S_1$), thianthrene ($S_2$), phenanthridine ($N_1$), phenanthroline ($N_2$), phenazine ($N_2$).

Heterocyclic groups (including heteroaryl groups) which have a nitrogen ring atom in the form of an —NH— group may be N-substituted, that is, as —NR—. For example, pyrrole may be N-methyl substituted, to give N-methypyrrole. Examples of N-substitutents include, but are not limited to $C_{1-7}$alkyl, $C_{3-20}$heterocyclyl, $C_{5-20}$aryl, and acyl groups.

Heterocyclic groups (including heteroaryl groups) which have a nitrogen ring atom in the form of an —N=group may be substituted in the form of an N-oxide, that is, as —N(→O)= (also denoted —N$^+$(→O$^-$)=). For example, quinoline may be substituted to give quinoline N-oxide; pyridine to give pyridine N-oxide; benzofurazan to give benzofurazan N-oxide (also known as benzofuroxan).

Cyclic groups may additionally bear one or more oxo (=O) groups on ring carbon atoms. Monocyclic examples of such groups include, but are not limited to, those derived from:

$C_5$: cyclopentanone, cyclopentenone, cyclopentadienone;

$C_6$: cyclohexanone, cyclohexenone, cyclohexadienone;

$O_1$: furanone ($C_5$), pyrone ($C_6$);

$N_1$: pyrrolidone (pyrrolidinone) ($C_5$), piperidinone (piperidone) ($C_6$), piperidinedione ($C_6$);

$N_2$: imidazolidone (imidazolidinone) ($C_5$), pyrazolone (pyrazolinone) ($C_5$), piperazinone ($C_6$), piperazinedione ($C_6$), pyridazinone ($C_6$), pyrimidinone ($C_6$) (e.g., cytosine), pyrimidinedione ($C_6$) (e.g., thymine, uracil), barbituric acid ($C_6$);

$N_1S_1$: thiazolone ($C_5$), isothiazolone ($C_5$);

$N_1O_1$: oxazolinone ($C_5$).

Polycyclic examples of such groups include, but are not limited to, those derived from:

$C_9$: indenedione;

$C_{10}$: tetralone, decalone;

$N_1$: oxindole ($C_9$);

$O_1$: benzopyrone (e.g., coumarin, isocoumarin, chromone) ($C_{10}$);

$N_1O_1$: benzoxazolinone ($C_9$), benzoxazolinone ($C_{10}$);

$N_2$: quinazolinedione ($C_{10}$);

$N_4$: purinone ($C_9$) (e.g., guanine).

Still more examples of cyclic groups which bear one or more oxo (=O) groups on ring carbon atoms include, but are not limited to, those derived from:

cyclic anhydrides (—C(=O)—O—C(=O)— in a ring), including but not limited to maleic anhydride ($C_5$), succinic anhydride ($C_5$), and glutaric anhydride ($C_6$);

cyclic carbonates (—O—C(=O)—O— in a ring), such as ethylene carbonate ($C_5$) and 1,2-propylene carbonate ($C_5$);

imides (—C(=O)—NR—C(=O)— in a ring), including but not limited to, succinimide ($C_5$), maleimide ($C_5$), phthalimide, and glutarimide ($C_6$);

lactones (cyclic esters, —O—C(=O)— in a ring), including, but not limited to, β-propiolactone, γ-butyrolactone, δ-valerolactone (2-piperidone), and ε-caprolactone;

lactams (cyclic amides, —NR—C(=O)— in a ring), including, but not limited to, β-propiolactam ($C_4$), γ-butyrolactam (2-pyrrolidone) ($C_5$), δ-valerolactam ($C_6$), and ε-caprolactam ($C_7$);

cyclic carbamates (—O—C(=O)—NR— in a ring), such as 2-oxazolidone ($C_5$);

cyclic ureas (—NR—C(=O)—NR— in a ring), such as 2-imidazolidone ($C_5$) and pyrimidine-2,4-dione (e.g., thymine, uracil) ($C_6$).

The above alkyl, alkylidene, alkylidyne, heterocyclyl, and aryl groups, whether alone or part of another substituent, may themselves optionally be substituted with one or more groups selected from themselves and the additional substituents listed below.

Hydrogen: —H. Note that if the substituent at a particular position is hydrogen, it may be convenient to refer to the compound as being "unsubstituted" at that position.

Halo: —F, —Cl, —Br, and —I.

Hydroxy: —OH.

Ether: —OR, wherein R is an ether substituent, for example, a $C_{1-7}$alkyl group (also referred to as a $C_{1-7}$alkoxy group, discussed below), a $C_{3-20}$heterocyclyl group (also referred to as a $C_{3-20}$heterocyclyloxy group), or a $C_{1-20}$aryl group (also referred to as a $C_{5-20}$aryloxy group), preferably a $C_{1-7}$alkyl group.

$C_{1-7}$alkoxy: —OR, wherein R is a $C_{1-7}$alkyl group. Examples of $C_{1-7}$alkoxy groups include, but are not limited to, —OMe (methoxy), —OEt (ethoxy), —O(nPr) (n-propoxy), —O(iPr) (isopropoxy), —O(nBu) (n-butoxy), —O(sBu) (sec-butoxy), —O(iBu) (isobutoxy), and —O(tBu) (tert-butoxy).

Acetal: —CH(OR$^1$)(OR$^2$), wherein R$^1$ and R$^2$ are independently acetal substituents, for example, a $C_{1-7}$alkyl group, a $C_{3-20}$heterocyclyl group, or a $C_{5-20}$aryl group, preferably a $C_{1-7}$alkyl group, or, in the case of a "cyclic" acetal group, R$^1$ and R$^2$, taken together with the two oxygen atoms to which they are attached, and the carbon atoms to which they are attached, form a heterocyclic ring having from 4 to 8 ring atoms. Examples of acetal groups include, but are not limited to, —CH(OMe)$_2$, —CH(OEt)$_2$, and —CH(OMe)(OEt).

Hemiacetal: —CH(OH)(OR$^1$), wherein R$^1$ is a hemiacetal substituent, for example, a $C_{1-7}$alkyl group, a $C_{3-20}$heterocyclyl group, or a $C_{5-20}$aryl group, preferably a $C_{1-7}$alkyl group. Examples of hemiacetal groups include, but are not limited to, —CH(OH)(OMe) and —CH(OH)(OEt).

Ketal: —CR(OR$^1$)(OR$^2$), where R$^1$ and R$^2$ are as defined for acetals, and R is a ketal substituent other than hydrogen, for example, a C$_{1-7}$alkyl group, a C$_{3-20}$heterocyclyl group, or a C$_{5-20}$aryl group, preferably a C$_{1-7}$alkyl group. Examples ketal groups include, but are not limited to, —C(Me)(OMe)$_2$, —C(Me)(OEt)$_2$, —C(Me)(OMe)(OEt), —C(Et)(OMe)$_2$, —C(Et)(OEt)$_2$, and —C(Et)(OMe)(OEt).

Hemiketal: —CR(OH)(OR$^1$), where R$^1$ is as defined for hemiacetals, and R is a hemiketal substituent other than hydrogen, for example, a C$_{1-7}$alkyl group, a C$_{3-20}$heterocyclyl group, or a C$_{1-20}$aryl group, preferably a C$_{1-7}$alkyl group. Examples of hemiacetal groups include, but are not limited to, —C(Me)(OH)(OMe), —C(Et)(OH)(OMe), —C(Me)(OH)(OEt), and —C(Et)(OH)(OEt).

Oxo (keto, -one): =O.

Thione (thioketone): =S.

Imino (imine): =NR, wherein R is an imino substituent, for example, hydrogen, C$_{1-7}$alkyl group, a C$_{3-20}$heterocyclyl group, or a C$_{5-20}$aryl group, preferably hydrogen or a C$_{1-7}$alkyl group. Examples of ester groups include, but are not limited to, =NH, =NMe, =NEt, and =NPh.

Formyl (carbaldehyde, carboxaldehyde): —C(=O)H.

Acyl (keto): —C(=O)R, wherein R is an acyl substituent, for example, a C$_{1-7}$alkyl group (also referred to as C$_{1-7}$alkylacyl or C$_{1-7}$alkanoyl), a C$_{3-20}$heterocyclyl group (also referred to as C$_{3-20}$heterocyclylacyl), or a C$_{5-20}$aryl group (also referred to as C$_{5-20}$arylacyl), preferably a C$_{1-7}$alkyl group. Examples of acyl groups include, but are not limited to, —C(=O)CH$_3$ (acetyl), —C(=O)CH$_2$CH$_3$ (propionyl), —C(=O)C(CH$_3$)$_3$ (t-butyryl), and —C(=O)Ph (benzoyl, phenone).

Carboxy (carboxylic acid): —C(=O)OH.

Thiocarboxy (thiocarboxylic acid): C(=S)SH.

Thiolocarboxy (thiolocarboxylic acid): —C(=O)SH.

Thionocarboxy (thionocarboxylic acid): —C(=S)OH.

Imidic acid: —C(=NH)OH.

Hydroxamic acid: —C(=NOH)OH.

Ester (carboxylate, carboxylic acid ester, oxycarbonyl): —C(=O)OR, wherein R is an ester substituent, for example, a C$_{1-7}$alkyl group, a C$_{3-20}$heterocyclyl group, or a C$_{5-20}$aryl group, preferably a C$_{1-7}$alkyl group. Examples of ester groups include, but are not limited to, —C(=O)OCH$_3$, —C(=O)OCH$_2$CH$_3$, —C(=O)OC(CH$_3$)$_3$, and —C(=O)OPh.

Acyloxy (reverse ester): —OC(=O)R, wherein R is an acyloxy substituent, for example, a C$_{1-7}$alkyl group, a C$_{3-20}$heterocyclyl group, or a C$_{5-20}$aryl group, preferably a C$_{1-7}$alkyl group. Examples of acyloxy groups include, but are not limited to, —OC(=O)CH$_3$ (acetoxy), —OC(=O)CH$_2$CH$_3$, —OC(=O)C(CH$_3$)$_3$, —OC(=O)Ph, and —OC(=O)CH$_2$Ph.

Oxycarboyloxy: —OC(=O)OR, wherein R is an ester substituent, for example, a C$_{1-7}$alkyl group, a C$_{3-20}$heterocyclyl group, or a C$_{5-20}$aryl group, preferably a C$_{1-7}$alkyl group. Examples of ester groups include, but are not limited to, —OC(=O)OCH$_3$, —OC(=O)OCH$_2$CH$_3$, —OC(=O)OC(CH$_3$)$_3$, and —OC(=O)OPh.

Amido (carbamoyl, carbamyl, aminocarbonyl, carboxamide): —C(=O)NR$^1$R$^2$, wherein R$^1$ and R$^2$ are independently amino substituents, as defined for amino groups. Examples of amido groups include, but are not limited to, —C(=O)NH$_2$, —C(=O)NHCH$_3$, —C(=O)N(CH$_3$)$_2$, —C(=O)NHCH$_2$CH$_3$, and —C(=O)N(CH$_2$CH$_3$)$_2$, as well as amido groups in which R$^1$ and R$^2$, together with the nitrogen atom to which they are attached, form a heterocyclic structure as in, for example, piperidinocarbonyl, morpholinocarbonyl, thiomorpholinocarbonyl, and piperazinocarbonyl.

Acylamido (acylamino): —NR$^1$C(=O)R$^2$, wherein R$^1$ is an amide substituent, for example, hydrogen, a C$_{1-7}$alkyl group, a C$_{3-20}$heterocyclyl group, or a C$_{5-20}$aryl group, preferably hydrogen or a C$_{1-7}$alkyl group, and R$^2$ is an acyl substituent, for example, a C$_{1-7}$alkyl group, a C$_{3-20}$heterocyclyl group, or a C$_{5-20}$aryl group, preferably hydrogen or a C$_{1-7}$alkyl group. Examples of acylamide groups include, but are not limited to, —NHC(=O)CH$_3$, —NHC(=O)CH$_2$CH$_3$, and —NHC(=O)Ph. R$^1$ and R$^2$ may together form a cyclic structure, as in, for example, succinimidyl, maleimidyl, and phthalimidyl:

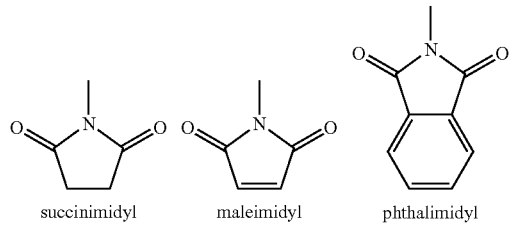

succinimidyl    maleimidyl    phthalimidyl

Thioamido (thiocarbamyl): —C(=S)NR$^1$R$^2$, wherein R$^1$ and R$^2$ are independently amino substituents, as defined for amino groups. Examples of amido groups include, but are not limited to, —C(=S)NH$_2$, —C(=S)NHCH$_3$, —C(=S)N(CH$_3$)$_2$, and —C(=S)NHCH$_2$CH$_3$.

Ureido: —N(R$^1$)CONR$^2$R$^3$ wherein R$^2$ and R$^3$ are independently amino substituents, as defined for amino groups, and R$^1$ is a ureido substituent, for example, hydrogen, a C$_{1-7}$alkyl group, a C$_{3-20}$heterocyclyl group, or a C$_{5-20}$aryl group, preferably hydrogen or a C$_{1-7}$alkyl group. Examples of ureido groups include, but are not limited to, —NHCONH$_2$, —NHCONHMe, —NHCONHEt, —NHCONMe$_2$, —NHCONEt$_2$, —NMeCONH$_2$, —NMeCONHMe, —NMeCONHEt, —NMeCONMe$_2$, and —NMeCONEt$_2$.

Guanidino: —NH—C(=NH)NH$_2$.

Tetrazolyl: a five membered aromatic ring having four nitrogen atoms and one carbon atom,

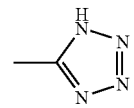

Amino: —NR$^1$R$^2$, wherein R$^1$ and R$^2$ are independently amino substituents, for example, hydrogen, a C$_{1-7}$alkyl group (also referred to as C$_{1-7}$alkylamino or di-C$_{1-7}$alkylamino), a C$_{3-20}$heterocyclyl group, or a C$_{5-20}$aryl group, preferably H or a C$_{1-7}$alkyl group, or, in the case of a "cyclic" amino group, R$^1$ and R$^2$, taken together with the nitrogen atom to which they are attached, form a heterocyclic ring having from 4 to 8 ring atoms. Amino groups may be primary (—NH$_2$), secondary (—NHR$^1$), or tertiary (—NHR$^1$R$^2$), and in cationic form, may be quaternary (—$^+$NR$^1$R$^2$R$^3$). Examples of amino groups include, but are not limited to, —NH$_2$, —NHCH$_3$, —NHC(CH$_3$)$_2$, —N(CH$_3$)$_2$, —N(CH$_2$CH$_3$)$_2$, and —NHPh. Examples of cyclic amino groups include, but are not limited to, aziridino, azetidino, pyrrolidino, piperidino, piperazino, morpholino, and thiomorpholino.

Amidine (amidino): —C(=NR)NR$_2$, wherein each R is an amidine substituent, for example, hydrogen, a C$_{1-7}$alkyl group, a C$_{3-20}$heterocyclyl group, or a C$_{5-20}$aryl group, preferably H or a C$_{1-7}$alkyl group. Examples of amidine groups include, but are not limited to, —C(=NH)NH$_2$, —C(=NH)NMe$_2$, and —C(=NMe)NMe$_2$.

Nitro: —NO$_2$.

Nitroso: —NO$_2$.

Azido: —N$_3$.

Cyano (nitrile, carbonitrile): —CN.

Isocyano: —NC.

Cyanato: —OCN.

Isocyanato: —NCO.

Thiocyano (thiocyanato): —SCN.

Isothiocyano (isothiocyanato): —NCS.

Sulfhydryl (thiol, mercapto): —SH.

Thioether (sulfide): —SR, wherein R is a thioether substituent for example, a C$_{1-7}$alkyl group (also referred to as a C$_{1-7}$alkylthio group), a C$_{3-20}$heterocyclyl group, or a C$_{1-20}$aryl group, preferably a C$_{1-7}$alkyl group. Examples of C$_{1-7}$alkylthio groups include, but are not limited to, —SCH$_3$ and —SCH$_2$CH$_3$.

Disulfide: —SS—R, wherein R is a disulfide substituent, for example, a C$_{1-7}$alkyl group, a C$_{3-20}$heterocyclyl group, or a C$_{5-20}$aryl group, preferably a C$_{1-7}$alkyl group (also referred to herein as C$_{1-7}$alkyl disulfide). Examples of C$_{1-7}$alkyl disulfide groups include, but are not limited to, —SSCH$_3$ and —SSCH$_2$CH$_3$.

Sulfonic acid (sulfo): —S(=O)$_2$OH, —SO$_3$H.

Sulfonate (sulfonic acid ester): —S(=O)$_2$OR, wherein R is a sulfonate substituent, for example, a C$_{1-7}$alkyl group, a C$_{3-20}$heterocyclyl group, or a C$_{5-20}$aryl group, preferably a C$_{1-7}$alkyl group. Examples of sulfonate groups include, but are not limited to, —S(=O)$_2$OCH$_3$ and —S((=O)$_2$OCH$_2$CH$_3$.

Sulfinic acid: —S(=O)OH, —SO$_2$H.

Sulfinate (sulfinic acid ester): —S(=O)OR; wherein R is a sulfinate substituent, for example, a C$_{1-7}$alkyl group, a C$_{3-20}$heterocyclyl group, or a C$_{5-20}$aryl group, preferably a C$_{1-7}$alkyl group. Examples of sulfinate groups include, but are not limited to, —S(=O)OCH$_3$ and —S(=O)OCH$_2$CH$_3$.

Sulfate: —OS(=O)$_2$OR; wherein R is a sulfate substituent, for example, a C$_{1-7}$alkyl group, a C$_{3-20}$heterocyclyl group, or a C$_{5-20}$aryl group, preferably a C$_{1-7}$alkyl group. Examples of sulfate groups include, but are not limited to, —OS(=O)$_2$OCH$_3$ and —SO(=O)$_2$OCH$_2$CH$_3$.

Sulfone (sulfonyl): —S(=O)$_2$R, wherein R is a sulfone substituent, for example, a C$_{1-7}$alkyl group, a C$_{3-20}$heterocyclyl group, or a C$_{5-20}$aryl group, preferably a C$_{1-7}$alkyl group, for example, a fluorinated or perfluorinated C$_{1-7}$alkyl group. Examples of sulfone groups include, but are not limited to, —S(=O)$_2$CH$_3$ (methanesulfonyl, mesyl), —S(=O)$_2$CF$_3$ (triflyl), —S(=O)$_2$CH$_2$CH$_3$ (esyl), —S(=O)$_2$C$_4$F$_9$ (nonaflyl), —S(=O)$_2$CH$_2$CF$_3$ (tresyl), —S(=O)$_2$Ph (phenylsulfonyl, besyl), 4-methylphenylsulfonyl (tosyl), 4-chlorophenylsulfonyl (closyl), 4-bromophenylsulfonyl (brosyl), 4-nitrophenyl (nosyl), 2-naphthalenesulfonate (napsyl), and 5-dimethylamino-naphthalen-1-ylsulfonate (dansyl).

Sulfine (sulfinyl, sulfoxide): —S(=O)R, wherein R is a sulfine substituent, for example, a C$_{1-7}$alkyl group, a C$_{3-20}$heterocyclyl group, or a C$_{5-20}$aryl group, preferably a C$_1$alkyl group. Examples of sulfine groups include, but are not limited to, —S(=O)CH$_3$ and —S(=O)CH$_2$CH$_3$.

Sulfonyloxy: —OS(=O)$_2$R, wherein R is a sulfonyloxy substituent, for example, a C$_{1-7}$alkyl group, a C$_{3-20}$heterocyclyl group, or a C$_{5-20}$aryl group, preferably a C$_{1-7}$alkyl group. Examples of sulfonyloxy groups include, but are not limited to, —OS(=O)$_2$CH$_3$ (mesylate) and —OS(=O)$_2$CH$_2$CH$_3$ (esylate).

Sulfinyloxy: —OS(=O)R, wherein R is a sulfinyloxy substituent, for example, a C$_{1-7}$alkyl group, a C$_{3-20}$heterocyclyl group, or a C$_{5-20}$aryl group, preferably a C$_{1-7}$alkyl group.

Examples of sulfinyloxy groups include, but are not limited to, —OS(=O)CH$_3$ and —OS(=O)CH$_2$CH$_3$.

Sulfamino: —NR$^1$S(=O)$_2$OH, wherein R$^1$ is an amino substituent, as defined for amino groups. Examples of sulfamino groups include, but are not limited to, —NHS(=O)$_2$OH and —N(CH$_3$)S(=O)$_2$OH.

Sulfonamino: —NR$^1$S(=O)$_2$R, wherein R$^1$ is an amino substituent, as defined for amino groups, and R is a sulfonamino substituent, for example, a C$_{1-7}$alkyl group, a C$_{3-20}$heterocyclyl group, or a C$_{5-20}$aryl group, preferably a C$_{1-7}$alkyl group. Examples of sulfonamino groups include, but are not limited to, —NHS(=O)$_2$CH$_3$ and —N(CH$_3$)S(=O)$_2$C$_6$H$_5$.

Sulfinamino: —NR$^1$S(=O)R, wherein R$^1$ is an amino substituent, as defined for amino groups, and R is a sulfinamino substituent, for example, a C$_{1-7}$alkyl group, a C$_{3-20}$heterocyclyl group, or a C$_{5-10}$aryl group, preferably a C$_{1-7}$alkyl group. Examples of sulfinamino groups include, but are not limited to, —NHS(=O)CH$_3$ and —N(CH$_3$)S(=O)C$_6$H$_5$.

Sulfamyl: —S(=O)NR$^1$R$^2$, wherein R$^1$ and R$^2$ are independently amino substituents, as defined for amino groups. Examples of sulfamyl groups include, but are not limited to, —S(=O)NH$_2$, —S(=O)NH(CH$_3$), —S(=O)N(CH$_3$)$_2$, —S(=O)NH(CH$_2$CH$_3$), —S(=O)N(CH$_2$CH$_3$)$_2$, and —S(=O)NHPh.

Sulfonamido: —S(=O)$_2$NR$^1$R$^2$, wherein R$^1$ and R$^2$ are independently amino substituents, as defined for amino groups. Examples of sulfonamido groups include, but are not limited to, —S(=O)$_2$NH$_2$, —S(=O)$_2$NH(CH$_3$), —S(=O)$_2$N(CH$_3$)$_2$, —S(=O)$_2$NH(CH$_2$CH$_3$), —S(=O)$_2$N(CH$_2$CH$_3$)$_2$, and —S(=O)$_2$NHPh.

Phosphino (phosphine): —PR$_2$, wherein R is a phosphino substituent, for example, —H, a C$_{1-7}$alkyl group, a C$_{3-20}$heterocyclyl group, or a C$_{5-20}$aryl group, preferably —H, a C$_{1-7}$alkyl group, or a C$_{5-20}$aryl group. Examples of phosphino groups include, but are not limited to, —PH$_2$, —P(CH$_3$)$_2$, —P(CH$_2$CH$_3$)$_2$, —P(t-Bu)$_2$, and —P(Ph)$_2$.

Phospho: —P(=O)$_2$.

Phosphinyl (phosphine oxide): —P(=O)R$_2$, wherein R is a phosphinyl substituent, for example, a C$_{1-7}$alkyl group, a C$_{3-20}$heterocyclyl group, or a C$_{5-20}$aryl group, preferably a C$_{1-7}$alkyl group or a C$_{5-20}$aryl group. Examples of phosphinyl groups include, but are not limited to, —P(=O)(CH$_3$)$_2$, —P(=O)(CH$_2$CH$_3$)$_2$, —P(=O)(t-Bu)$_2$, and —P(=O)(Ph)$_2$.

Phosphonic acid (phosphono): —P(=O)(OH)$_2$.

Phosphonate (phosphono ester): —P(=O)(OR)$_2$, where R is a phosphonate substituent, for example, —H, a C$_{1-7}$alkyl group, a C$_{3-20}$heterocyclyl group, or a C$_{5-20}$aryl group, preferably —H, a C$_{1-7}$alkyl group, or a C$_{5-20}$aryl group. Examples of phosphonate groups include, but are not limited to, —P(=O)(OCH$_3$)$_2$, —P(=O)(OCH$_2$CH$_3$)$_2$, —P(=O)(O-t-Bu)$_2$, and —P(=O)(OPh)$_2$.

Phosphoric acid (phosphonooxy): —OP(=O)(OH)$_2$.

Phosphate (phosphonooxy ester): —OP(=O)(OR)$_2$, where R is a phosphate substituent, for example, —H, a C$_{1-7}$alkyl group, a C$_{3-20}$heterocyclyl group, or a C$_{5-20}$aryl group, preferably —H, a C$_{1-7}$alkyl group, or a C$_{5-20}$aryl group. Examples of phosphate groups include, but are not limited to, —OP(=O)(OCH$_3$)$_2$, —OP(=O)(OCH$_2$CH$_3$)$_2$, —OP(=O)(O-t-Bu)$_2$, and —OP(=O)(OPh)$_2$.

Phosphorous acid: —OP(OH)$_2$.

Phosphite: —OP(OR)$_2$, where R is a phosphite substituent for example, —H, a C$_{1-7}$alkyl group, a C$_{3-20}$heterocyclyl group, or a C$_{5-20}$aryl group, preferably —H, a C$_{1-7}$alkyl group, or a C$_{5-20}$aryl group. Examples of phosphite groups include, but are not limited to, —OP(OCH$_3$)$_2$, —OP(OCH$_2$CH$_3$)$_2$, —OP(O-t-Bu)$_2$, and —OP(OPh)$_2$.

Phosphoramidite: —OP(OR$^1$)—NR$^2$$_2$, where R$^1$ and R$^2$ are phosphoramidite substituents, for example, —H, a (optionally substituted) C$_{1-7}$alkyl group, a C$_{5-20}$heterocyclyl group, or a C$_{5-20}$aryl group, preferably —H, a C$_{1-7}$alkyl group, or a C$_{5-20}$aryl group. Examples of phosphoramidite groups include, but are not limited to, —OP(OCH$_2$CH$_3$)—N(CH$_3$)$_2$, —OP(OCH$_2$CH$_3$)—N(i-Pr)$_2$, and —OP(OCH$_2$CH$_2$CN)—N(i-Pr)$_2$.

Phosphoramidate: —OP(=O)(OR$^1$)—NR$^2$$_2$, where R$^1$ and R$^2$ are phosphoramidate substituents, for example, —H, a (optionally substituted) C$_{1-7}$alkyl group, a C$_{3-20}$heterocyclyl group, or a C$_{5-20}$aryl group, preferably —H, a C$_{1-7}$alkyl group, or a C$_{5-20}$aryl group. Examples of phosphoramidate groups include, but are not limited to, —OP(=O)(OCH$_2$CH$_3$)—N(CH$_3$)$_2$, —OP(=O)(OCH$_2$CH$_3$)—N(i-Pr)$_2$, and —OP(=O)(OCH$_2$CH$_2$CN)—N(i-Pr)$_2$.

In many cases, substituents may themselves be substituted. For example, a C$_{1-7}$alkyl group may be substituted with, for example, hydroxy (also referred to as a C$_{1-7}$hydroxyalkyl group), C$_{1-7}$alkoxy (also referred to as a C$_{1-7}$alkoxyalkyl group), amino (also referred to as a C$_{1-7}$aminoalkyl group), halo (also referred to as a C$_{1-7}$haloalkyl group), carboxy (also referred to as a C$_{1-7}$carboxyalkyl group), and C$_{5-20}$aryl (also referred to as a C$_{5-20}$aryl-C$_{1-7}$alkyl group).

Similarly, a C$_{5-20}$aryl group may be substituted with, for example, hydroxy (also referred to as a C$_{5-20}$hydroxyaryl group), halo (also referred to as a C$_{5-20}$haloaryl group), amino (also referred to as a C$_{5-20}$-aminoaryl group, e.g., as in aniline), C$_{1-7}$alkyl (also referred to as a C$_{1-7}$alkyl-C$_{5-20}$aryl group, e.g., as in toluene), and C$_{1-7}$alkoxy (also referred to as a C$_{1-7}$alkoxy-C$_{5-20}$aryl group, e.g., as in anisole).

These and other specific examples of such substituted-substituents are described below.

C$_{1-7}$haloalkyl group: The term "C$_{1-7}$haloalkyl group," as used herein, pertains to a C$_{1-7}$alkyl group in which at least one hydrogen atom (e.g., 1, 2, 3) has been replaced with a halogen atom (e.g., F, Cl, Br, I). If more than one hydrogen atom has been replaced with a halogen atom, the halogen atoms may independently be the same or different. Every hydrogen atom may be replaced with a halogen atom, in which case the group may conveniently be referred to as a C$_{1-7}$ perhaloalkyl group." Examples of C$_{1-7}$haloalkyl groups include, but are not limited to, —CF$_3$, —CHF$_2$, —CH$_2$F, —CCl$_3$, —CBr$_3$, —CH$_2$CH$_2$F, —CH$_2$CHF$_2$, and —CH$_2$CF$_3$.

C$_{1-7}$haloalkoxy: —OR, wherein R is a C$_{1-7}$haloalkyl group. Examples of C$_{1-7}$haloalkoxy groups include, but are not limited to, —OCF$_3$, —OCHF$_2$, —OCH$_2$F, —OCCl$_3$, —OCBr$_3$, —OCH$_2$CH$_2$F, —OCH$_2$CHF$_2$, and —OCH$_2$CF$_3$.

C$_{1-7}$hydroxyalkyl: The term "C$_{1-7}$hydroxyalkyl group," as used herein, pertains to a C$_{1-7}$alkyl group in which at least one hydrogen atom has been replaced with a hydroxy group. Examples of C$_{1-7}$hydroxyalkyl groups include, but are not limited to, —CH$_2$OH, —CH$_2$CH$_2$OH, and —CH(OH)CH$_2$OH.

C$_{1-7}$carboxyalkyl: The term "C$_{1-7}$carboxyalkyl group," as used herein, pertains to a C$_{1-7}$alkyl group in which at least one hydrogen atom has been replaced with a carboxy group. Examples of C$_{1-7}$carboxyalkyl groups include, but are not limited to, —CH$_2$COOH and —CH$_2$CH$_2$COOH.

C$_{1-7}$aminoalkyl: The term "C$_{1-7}$aminoalkyl group," as used herein, pertains to a C$_{1-7}$alkyl group in which at least one hydrogen atom has been replaced with an amino group. Examples of C$_{1-7}$aminoalkyl groups include, but are not limited to, —CH$_2$NH$_2$, —CH$_2$CH$_2$NH$_2$, and —CH$_2$CH$_2$N(CH$_3$)$_2$.

C$_{1-7}$aminoalkylamino: The term "C$_{1-7}$aminoalkylamino," as used herein, pertains to an amino group, —NR$^1$R$^2$, in which one of the substituents, R$^1$ or R$^2$, is itself a C$_{1-7}$aminoalkyl group (—C$_{1-7}$alkyl-NR$^1$R$^2$). The C$_{1-7}$aminoalkylamino may be represented, for example, by the formula —NR$^1$—C$_{1-7}$alkyl-NR$^1$R$^2$. Examples of amino-C$_{1-7}$alkylamino groups include, but are not limited to, groups of the formula —NR$^1$(CH$_2$)$_n$NR$^1$R$^2$, where n is 1 to 6, for example, —NHCH$_2$NH$_2$, —NH(CH$_2$)$_2$NH$_2$, —NH(CH$_2$)$_3$NH$_2$, —NH(CH$_2$)$_4$NH$_2$, —NH(CH$_2$)$_5$NH$_2$, —NH(CH$_2$)$_6$NH$_2$, —NHCH$_2$NH(Me), —NH(CH$_2$)$_2$NH(Me), —NH(CH$_2$)$_3$NH(Me), —NH(CH$_2$)$_4$NH(Me), —NH(CH$_2$)$_5$NH(Me), —NH(CH$_2$)$_6$NH(Me), —NHCH$_2$NH(Et), —NH(CH$_2$)$_2$NH(Et), —NH(CH$_2$)$_3$NH(Et), —NH(CH$_2$)$_4$NH(Et), —NH(CH$_2$)$_5$NH(Et), and —NH(CH$_2$)$_6$NH(Et).

C$_{3-7}$cycloalkyl-C$_{1-7}$alkyl: The term "," as used herein, describes certain C$_{1-7}$alkyl groups which have been substituted with a C$_{3-7}$cycloalkyl group. Examples of such groups include, but are not limited to, cyclopropylmethyl, cyclobutylmethyl, cyclopentylmethyl, and cyclohexylmethyl.

C$_{3-7}$cycloalkenyl-C$_{1-7}$alkyl: The term "," as used herein, describes certain C$_{1-7}$alkyl groups which have been substituted with a C$_{3-7}$cycloalkenyl group. Examples of such groups include, but are not limited to, cyclopropenylmethyl and cyclohexenylmethyl.

C$_{1-7}$alkyl-C$_{5-20}$aryl: The term "C$_{1-7}$alkyl-C$_{5-20}$aryl," as used herein, describes certain C$_{5-20}$aryl groups which have been substituted with a C$_{1-7}$alkyl group. Examples of such groups include, but are not limited to, tolyl (as in toluene), xylyl (as in xylene), mesityl (as in mesitylene), styryl (as in styrene), and cumenyl (as in cumene).

C$_{1-7}$alkyl-C$_{5-20}$aryloxy: The term "C$_{1-7}$alkyl-C$_{5-20}$aryloxy," as used herein, describes certain C$_{5-20}$aryloxy groups which have been substituted with a C$_{1-7}$alkyl group. Examples of such groups include, but are not limited to, tolyloxy, xylyloxy, mesityloxy, and cumenyloxy.

C$_{5-20}$aryl-C$_{1-7}$alkyl: The term "C$_{5-20}$aryl-C$_{1-7}$alkyl," as used herein, describers certain C$_{1-7}$alkyl groups which have been substituted with a C$_{5-20}$aryl group. Examples of such groups include, but are not limited to, benzyl (phenylmethyl), tolylmethyl, phenylethyl, triphenylmethyl (trityl), and cinnamyl (3-phenyl-2-propenyl, C$_6$H$_5$—CH=CH—CH$_2$—).

C$_{5-20}$aryl-C$_{1-7}$alkoxy: The term "C$_{5-20}$aryl-C$_{1-7}$alkoxy," as used herein, describes certain C$_{1-7}$alkoxy groups which have been substituted with a C$_{5-20}$aryl group. Examples of such groups include, but are not limited to, benzyloxy, tolylmethoxy, and phenylethoxy.

C$_{5-20}$haloaryl: The term "C$_{5-20}$haloaryl," as used herein, describes certain C$_{5-20}$aryl groups which have been substituted with one or more halo groups. Examples of such groups include, but are not limited to, halophenyl (e.g., fluorophenyl, chlorophenyl, bromophenyl, or iodophenyl, whether ortho-, meta-, or para-substituted), dihalophenyl, trihalophenyl, tetrahalophenyl, and pentahalophenyl.

Includes Other Forms

Unless otherwise specified, included in the above are the well known ionic, salt, solvate, and protected forms of these substituents. For example, a reference to carboxylic acid (—COOH) also includes the anionic (carboxylate) form (—COO$^-$), a salt or solvate thereof, as well as conventional protected forms. Similarly, a reference to an amino group includes the protonated form (—N$^+$HR$^1$R$^2$), a salt or solvate of the amino group, for example, a hydrochloride salt, as well as conventional protected forms of an amino group. Similarly, a reference to a hydroxyl group also includes the anionic form (—O⁻), a salt or solvate thereof, as well as conventional protected forms of a hydroxyl group.

Isomers, Salts, Solvates, Protected Forms, and Prodrugs

Certain compounds may exist in one or more particular geometric, optical, enantiomeric, diasteriomeric, epimeric, stereoisomeric, tautomeric, conformational, or anomeric forms, including but not limited to, cis- and trans-forms; E- and Z-forms; c-, t-, and r-forms; endo- and exo-forms; R—, S—, and meso-forms; D- and L-forms; d- and 1-forms; (+) and (−) forms; keto-, enol-, and enolate-forms; syn- and anti-forms; synclinal- and anticlinal-forms; α- and β-forms; axial and equatorial forms; boat-, chair-, twist-, envelope-, and halfchair-forms; and combinations thereof, hereinafter collectively referred to as "isomers" (or "isomeric forms").

Note that, except as discussed below for tautomeric forms, specifically excluded from the term "isomers," as used herein, are structural (or constitutional) isomers (i.e., isomers which differ in the connections between atoms rather than merely by the position of atoms in space). For example, a reference to a methoxy group, —OCH₃, is not to be construed as a reference to its structural isomer, a hydroxymethyl group, —CH₂OH. Similarly, a reference to ortho-chlorophenyl is not to be construed as a reference to its structural isomer, meta-chlorophenyl. However, a reference to a class of structures may well include structurally isomeric forms falling within that class (e.g., $C_{1-7}$alkyl includes n-propyl and iso-propyl; butyl includes n-, iso-, sec-, and tert-butyl; methoxyphenyl includes ortho-, meta-, and para-methoxyphenyl).

The above exclusion does not pertain to tautomeric forms, for example, keto-, enol-, and enolate-forms, as in, for example, the following tautomeric pairs: keto/enol (illustrated below), imine/enamine, amide/imino alcohol, amidine/amidine, nitroso/oxime, thioketone/enethiol, N-nitroso/hyroxyazo, and nitro/aci-nitro.

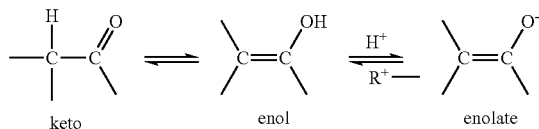

keto     enol     enolate

Note that specifically included in the term "isomer" are compounds with one or more isotopic substitutions. For example, H may be in any isotopic form, including ¹H, ²H (D), and ³H (T); C may be in any isotopic form, including ¹²C, ¹³C, and ¹⁴C; O may be in any isotopic form, including ¹⁶O and ¹⁸O; and the like.

Unless otherwise specified, a reference to a particular compound includes all such isomeric forms, including (wholly or partially) racemic and other mixtures thereof. Methods for the preparation (e.g., asymmetric synthesis) and separation (e.g., fractional crystallisation and chromatographic means) of such isomeric forms are either known in the art or are readily obtained by adapting the methods taught herein, or known methods, in a known manner.

Unless otherwise specified, a reference to a particular compound also includes ionic, salt, solvate, and protected forms of thereof, for example, as discussed below.

It may be convenient or desirable to prepare, purify, and/or handle a corresponding salt of the active compound, for example, a pharmaceutically-acceptable salt. Examples of pharmaceutically acceptable salts are discussed in Berge et al., 1977, "Pharmaceutically Acceptable Salts," *J. Pharm. Sci.*, Vol. 66, pp. 1-19.

For example, if the compound is anionic, or has a functional group which may be anionic (e.g., —COOH may be —COO⁻), then a salt may be formed with a suitable cation. Examples of suitable inorganic cations include, but are not limited to, alkali metal ions such as Na⁺ and K⁺, alkaline earth cations such as Ca²⁺ and Mg²⁺, and other cations such as Al⁺³. Examples of suitable organic cations include, but are not limited to, ammonium ion (i.e., NH₄⁺) and substituted ammonium ions (e.g., NH₃R⁺, NH₂R₂⁺, NHR₃⁺, NR₄⁺). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is N(CH₃)₄⁺.

If the compound is cationic, or has a functional group which may be cationic (e.g., —NH₂ may be —NH₃⁺), then a salt may be formed with a suitable anion. Examples of suitable inorganic anions include, but are not limited to, those derived from the following inorganic acids: hydrochloric, hydrobromic, hydroiodic, sulfuric, sulfurous, nitric, nitrous, phosphoric, and phosphorous.

Examples of suitable organic anions include, but are not limited to, those derived from the following organic acids: 2-acetyoxybenzoic, acetic, ascorbic, aspartic, benzoic, camphorsulfonic, cinnamic, citric, edetic, ethanedisulfonic, ethanesulfonic, fumaric, glucheptonic, gluconic, glutamic, glycolic, hydroxymaleic, hydroxynaphthalene carboxylic, isethionic, lactic, lactobionic, lauric, maleic, malic, methanesulfonic, mucic, oleic, oxalic, palmitic, pamoic, pantothenic, phenylacetic, phenylsulfonic, propionic, pyruvic, salicylic, stearic, succinic, sulfanilic, tartaric, toluenesulfonic, and valeric. Examples of suitable polymeric organic anions include, but are not limited to, those derived from the following polymeric acids: tannic acid, carboxymethyl cellulose.

It may be convenient or desirable to prepare, purify, and/or handle a corresponding solvate of the active compound. The term "solvate" is used herein in the conventional sense to refer to a complex of solute (e.g., active compound, salt of active compound) and solvent. If the solvent is water, the solvate may be conveniently referred to as a hydrate, for example, a mono-hydrate, a di-hydrate, a tri-hydrate, etc.

It may be convenient or desirable to prepare, purify, and/or handle the active compound in a chemically protected form. The term "chemically protected form" is used herein in the conventional chemical sense and pertains to a compound in which one or more reactive functional groups are protected from undesirable chemical reactions under specified conditions (e.g., pH, temperature, radiation, solvent, and the like). In practice, well known chemical methods are employed to reversibly render unreactive a functional group, which otherwise would be reactive, under specified conditions. In a chemically protected form, one or more reactive functional groups are in the form of a protected or protecting group (also known as a masked or masking group or a blocked or blocking group). By protecting a reactive functional group, reactions involving other unprotected reactive functional groups can be performed, without affecting the protected group; the protecting group may be removed, usually in a subsequent step, without substantially affecting the remainder of the molecule. See, for example, *Protective Groups in Organic Synthesis* (T. Green and P. Wuts; 3rd Edition; John Wiley and Sons, 1999).

A wide variety of such "protecting," "blocking," or "masking" methods are widely used and well known in organic synthesis. For example, a compound which has two non-equivalent reactive functional groups, both of which would be reactive under specified conditions, may be derivatized to render one of the functional groups "protected," and therefore unreactive, under the specified conditions; so protected, the compound may be used as a reactant which has effectively only one reactive functional group. After the desired reaction (involving the other functional group) is complete, the protected group may be "deprotected" to return it to its original functionality.

For example, a hydroxy group may be protected as an ether (—OR) or an ester (—OC(=O)R), for example, as: a t-butyl ether; a benzyl, benzhydryl (diphenylmethyl), or trityl (triphenylmethyl)ether; a trimethylsilyl or t-butyldimethylsilyl ether; or an acetyl ester (—OC(=O)CH$_3$, —OAc).

For example, an aldehyde or ketone group may be protected as an acetal (R—CH(OR)$_2$) or ketal (R$_2$C(OR)$_2$), respectively, in which the carbonyl group (>C=O) is converted to a diether (>C(OR)$_2$), by reaction with, for example, a primary alcohol. The aldehyde or ketone group is readily regenerated by hydrolysis using a large excess of water in the presence of acid.

For example, an amine group may be protected, for example, as an amide (—NRCO—R) or a urethane (—NRCO—OR), for example, as: a methyl amide (—NHCO—CH$_3$); a benzyloxy amide (—NHCO—OCH$_2$C$_6$H$_5$, —NH-Cbz); as a t-butoxy amide (—NHCO—OC(CH$_3$)$_3$, —NH-Bpoc); a 2-biphenyl-2-propoxy amide (—NHCO—OC(CH$_3$)$_2$C$_6$H$_4$C$_6$H$_5$, —NH-Bpoc), as a 9-fluorenylmethoxy amide (—NH-Fmoc), as a 6-nitroveratryloxy amide (—NH-Nvoc), as a 2-trimethylsilylethyloxy amide (—NH-Teoc), as a 2,2,2-trichloroethyloxy amide (—NH-Troc), as an allyloxy amide (—NH-Alloc), as a 2(-phenylsulphonyl)ethyloxy amide (—NH-Psec); or, in suitable cases (e.g., cyclic amines), as a nitroxide radical (>N—O.).

For example, a carboxylic acid group may be protected as an ester for example, as: an C$_{1-7}$alkyl ester (e.g., a methyl ester; a t-butyl ester); a C$_{1-7}$haloalkyl ester (e.g., a C$_{1-7}$trihaloalkyl ester); a triC$_{1-7}$alkylsilyl-C$_{1-7}$alkyl ester; or a C$_{5-20}$aryl-C$_{1-7}$alkyl ester (e.g., a benzyl ester; a nitrobenzyl ester); or as an amide, for example, as a methyl amide.

For example, a thiol group may be protected as a thioether (—SR), for example, as: a benzyl thioether; an acetamidomethyl ether (—S—CH$_2$NHC(=O)CH$_3$).

It may be convenient or desirable to prepare, purify, and/or handle the active compound in the form of a prodrug. The term "prodrug," as used herein, pertains to a compound which, when metabolised (e.g., in vivo), yields the desired active compound. Typically, the prodrug is inactive, or less active than the active compound, but may provide advantageous handling, administration, or metabolic properties.

For example, some prodrugs are esters of the active compound (e.g., a physiologically acceptable metabolically labile ester). During metabolism, the ester group (—C(=O)OR) is cleaved to yield the active drug. Such esters may be formed by esterification, for example, of any of the carboxylic acid groups (—C(=O)OH) in the parent compound, with, where appropriate, prior protection of any other reactive groups present in the parent compound, followed by deprotection if required.

Examples of such metabolically labile esters include those of the formula —C(=O)OR wherein R is:

C$_{1-7}$alkyl (e.g., -Me, -Et, -nPr, -iPr, -nBu, -sBu, -iBu, -tBu);

C$_{1-7}$-aminoalkyl (e.g., aminoethyl; 2-(N,N-diethylamino)ethyl; 2-(4-morpholino)ethyl); and acyloxy-C$_{1-7}$alkyl (e.g., acyloxymethyl;

acyloxyethyl;

pivaloyloxymethyl;

acetoxymethyl;

1-acetoxyethyl;

1-(1-methoxy-1-methyl)ethyl-carbonxyloxyethyl;

1-(benzoyloxy)ethyl; isopropoxy-carbonyloxymethyl;

1-isopropoxy-carbonyloxyethyl; cyclohexyl-carbonyloxymethyl;

1-cyclohexyl-carbonyloxyethyl;

cyclohexyloxy-carbonyloxymethyl;

1-cyclohexyloxy-carbonyloxyethyl;

(4-tetrahydropyranyloxy) carbonyloxymethyl;

1-(4-tetrahydropyranyloxy)carbonyloxyethyl;

(4-tetrahydropyranyl)carbonyloxymethyl; and 1-(4-tetrahydropyranyl)carbonyloxyethyl).

Also, some prodrugs are activated enzymatically to yield the active compound, or a compound which, upon further chemical reaction, yields the active compound (for example, as in ADEPT, GDEPT, LIDEPT, etc.). For example, the prodrug may be a sugar derivative or other glycoside conjugate, or may be an amino acid ester derivative.

Acronyms

For convenience, many chemical moieties are represented using well known abbreviations, including but not limited to, methyl (Me), ethyl (Et), n-propyl (nPr), iso-propyl (iPr), n-butyl (nBu), sec-butyl (sBu), iso-butyl (iBu), tert-butyl (tBu), n-hexyl (nHex), cyclohexyl (cHex), phenyl (Ph), biphenyl (biPh), benzyl (Bn), naphthyl (naph), methoxy (MeO), ethoxy (EtO), benzoyl (Bz), and acetyl (Ac).

For convenience, many chemical compounds are represented using well known abbreviations, including but not limited to, methanol (MeOH), ethanol (EtOH), iso-propanol (i-PrOH), methyl ethyl ketone (MEK), ether or diethyl ether (Et$_2$O), acetic acid (AcOH), dichloromethane (methylene chloride, DCM), acetonitrile (ACN), trifluoroacetic acid (TFA), dimethylformamide (DMF), tetrahydrofuran (THF), and dimethylsulfoxide (DMSO).

Chemical Synthesis

Compounds suitable for use in the present invention may be synthesised using known methods. Suitable reagents and intermediates are commercially available. Additionally, several methods for the chemical synthesis of suitable compounds for use in present invention are described herein. These methods may be modified and/or adapted in known ways in order to facilitate the synthesis of additional compounds suitable for use in the present invention.

Examples of some suitable methods for the synthesis of the compounds of the present invention are described below.

In one approach, an appropriate alkane diol is first mono-protected, for example, using tert-butyl-chloro-diphenylsilane, and then mono-activated, for example, with para-tosyl chloride. An example of such a method is shown in the following scheme.

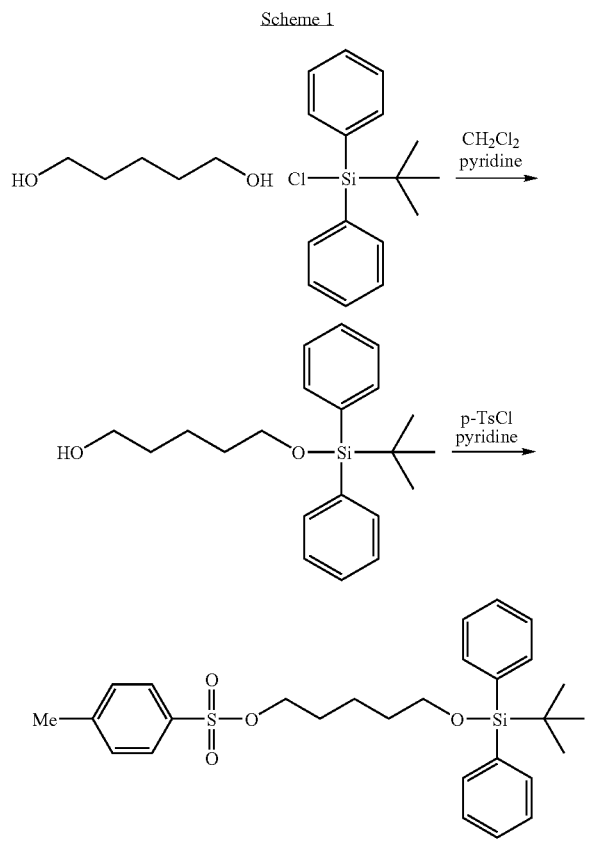

Separately, an appropriate aryl aldehyde is reacted with 1,3-dithioproprane to form the corresponding 1,3-dithiane derivative, which is then lithiated, for example, with butyl lithium. An example of such a method is shown in the following scheme.

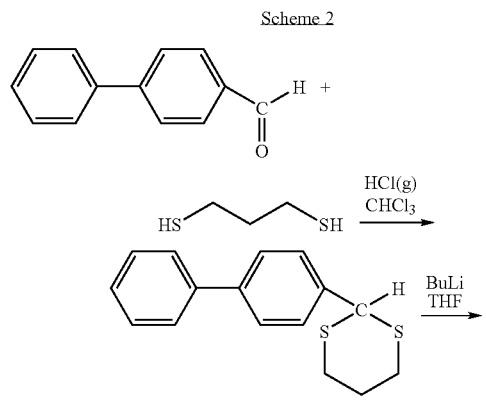

-continued

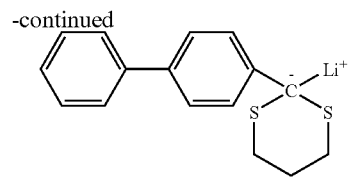

The lithiated 1,3-dithiane derivative is then reacted with the mono-protected, mono-activated alkane diol described above. The silyl protecting group is then removed, for example, using tetrabutyl ammonium fluoride. Finally, the 1,3-dithiane group is removed and converted back to a carbonyl group, for example, using copper chloride/copper oxide, to yield the target (aryl hydroxyalkyl ketone) compound. An example of such a method is shown in the following scheme.

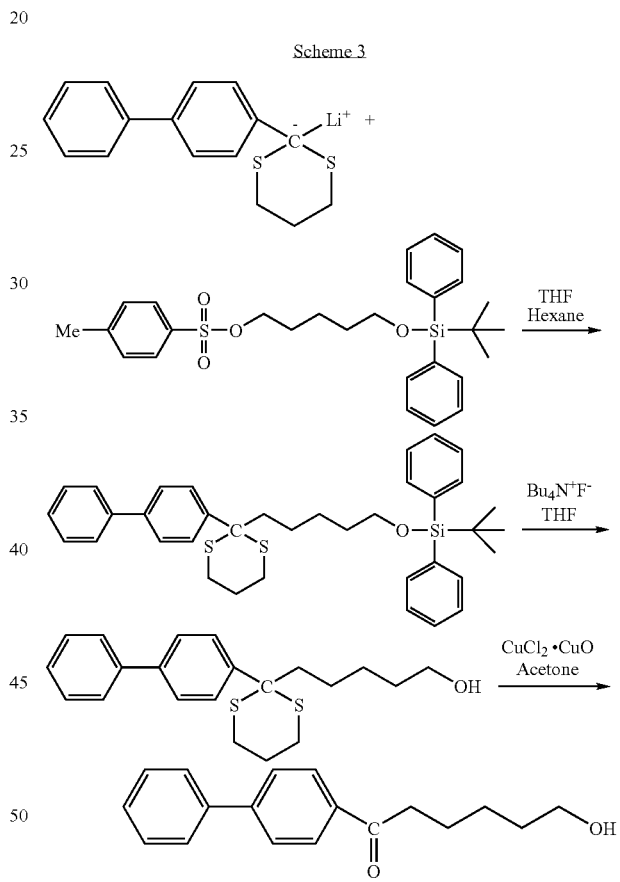

In another approach, a suitable aryl compound is first converted to an aryl methyl ketone, for example, in a Friedel-Crafts reaction, using, for example, acetyl chloride with aluminium chloride. An example of such a method is shown in the following scheme.

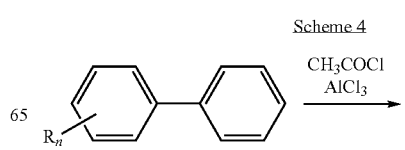

-continued

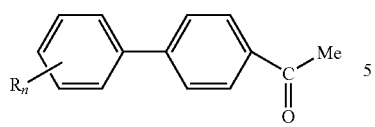

The aryl methyl ketone is then oxidized to form an aryl carboxylic acid, for example, using NaOBr. An example of such a method is shown in the following scheme.

Scheme 5

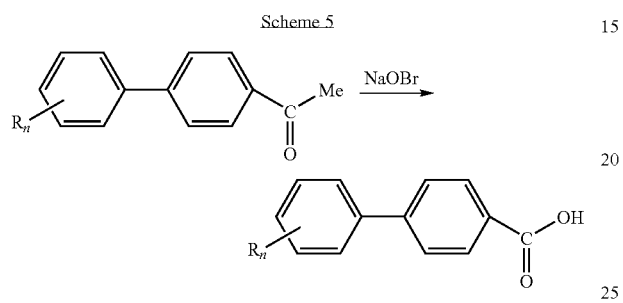

The aryl carboxylic acid is then converted to an aryl acyl halide, for example, using thionyl chloride. An example of such a method is shown in the following scheme.

Scheme 6

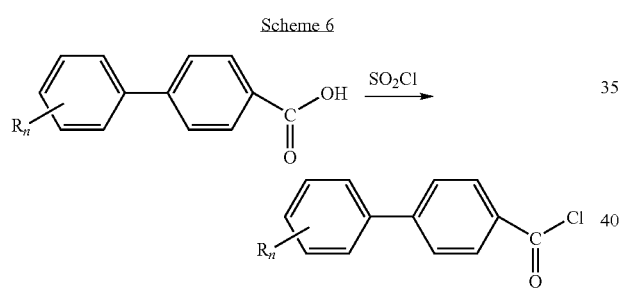

The aryl acyl halide is then converted to a reactive carbamate (e.g., a Weinreb amide), using, for example, N,O-dimethyl hydroxylamine hydrochloride. An example of such a method is shown in the following scheme.

Scheme 7

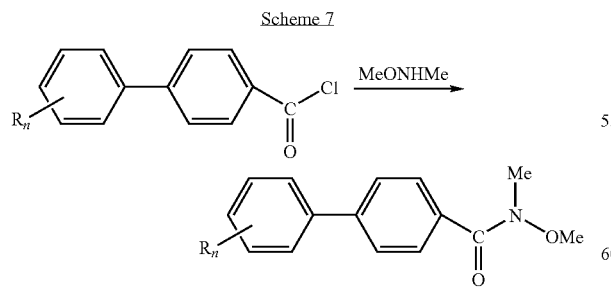

Separately, a suitable haloalkanol is prepared, for example, from a corresponding diol or cyclic ether (e.g., THF, THP), for example, using HBr. An example of such a method is shown in the following scheme.

Scheme 8

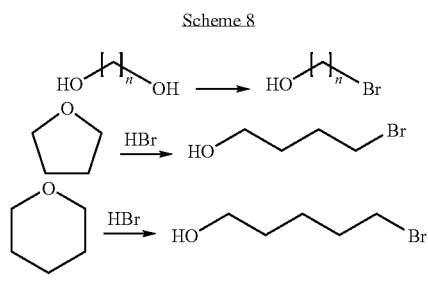

n = 1-10

The haloalkanol is then reacted with dihydropyran to form the corresponding tetrahydropyran ether, which is then reacted with magnesium to form the corresponding Grignard reagent. An example of such a method is shown in the following scheme.

Scheme 9

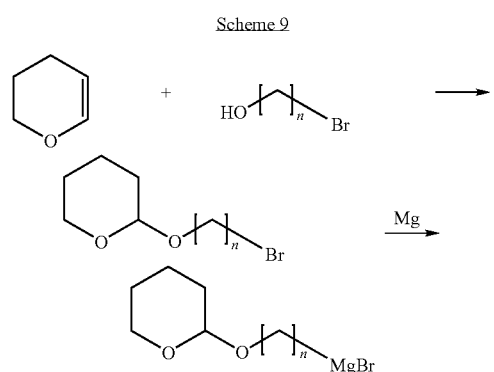

n = 1-10

The Grignard reagent is then reacted with an appropriate Weinreb amide, described above, to form the corresponding aryl tetrahydropyranoxyalkyl ketone. An example is shown in the following scheme.

Scheme 10

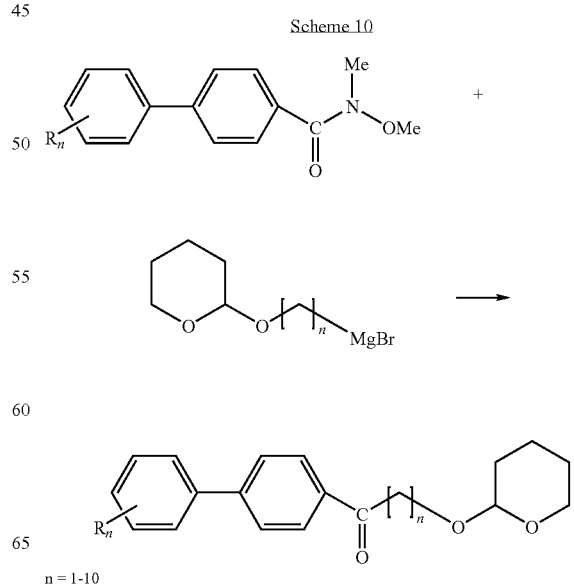

n = 1-10

The tetrahydropyran protecting group is then removed using, for example, one of a variety of known simple methods (as outlined, for example, Green and Wuts, *Protective Groups in Organic Synthesis*, 1999, J. Wiley, New York, pp. 49-54), to yield the target (aryl hydroxyalkyl ketone) compound. An example of such a method is shown in the following scheme.

Scheme 11

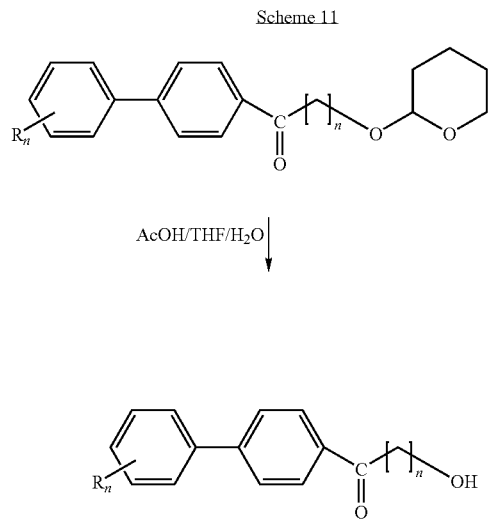

In another approach, a suitable bromoalkane is first converted to the corresponding Grignard reagent, and then reacted with a suitable Weinreb amide, described above, to form the target (e.g., aryl alkyl ketone) compound. An example of such a method is shown in the following scheme.

Scheme 13

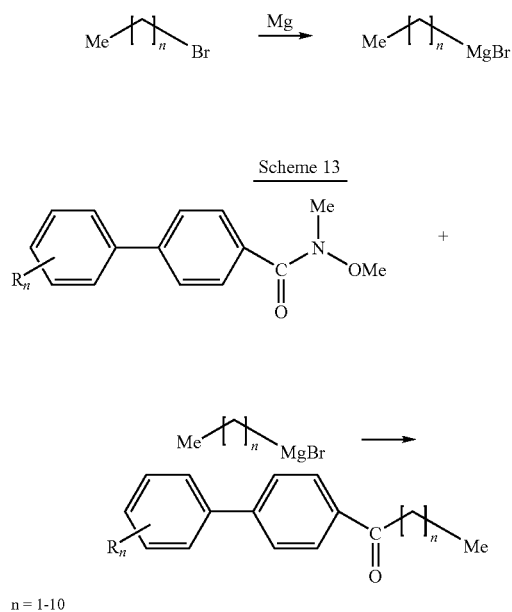

n = 1-10

In another approach, an appropriate dihaloalkane, e.g., a dibromoalkane, is converted to a corresponding di-Grignard reagent. An example of such a method is shown in the following scheme.

Scheme 14

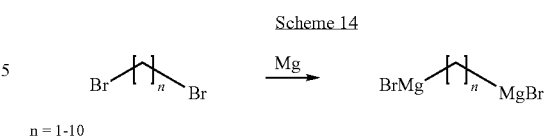

n = 1-10

Separately, a suitable Weinreb amide is prepared. An example of such a method is shown in the following scheme.

Scheme 15

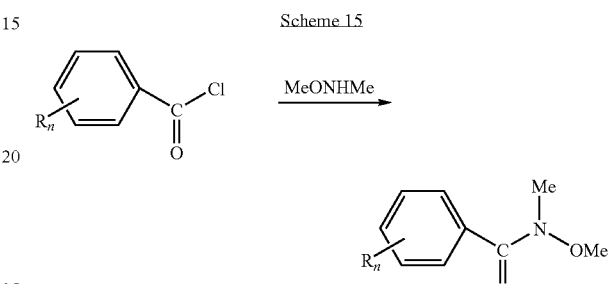

The di-Grignard reagent is then reacted with the Weinreb amide, to yield the target (di-ketone) compound.

Scheme 16

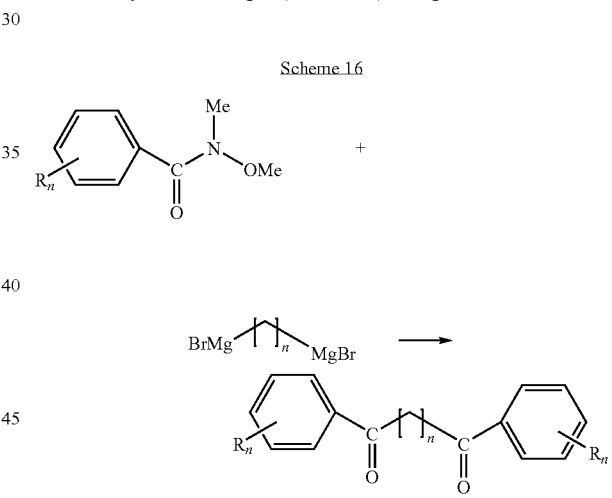

Methods for the preparation of compounds having a phosphonic acid group, include, for example, those described below.

In one method, ethenylidenebisphosphonate ($CH_2$=$C(P(=O)(OR)_2)_2$) is prepared from paraformaldehyde, diethylamine and a tetraalkyl methylene bisphosphonate ($H_2C(P(=O)(OR)_2)_2$), using, for example, the method described by Degenhardt and Burdsall, 1986. The ethenylidene-bisphosphonate is then reacted with a suitable aryl hydroxyalkyl ketone, in methylene chloride, in the presence of triethylamine, using, for example, the method described by Herczegh et al., 2002. The phosphate ester groups, e.g., ethyl groups, are removed e.g., with trimethylsilylbromide or left in place. An example of such a method is illustrated in the following scheme.

Scheme 17

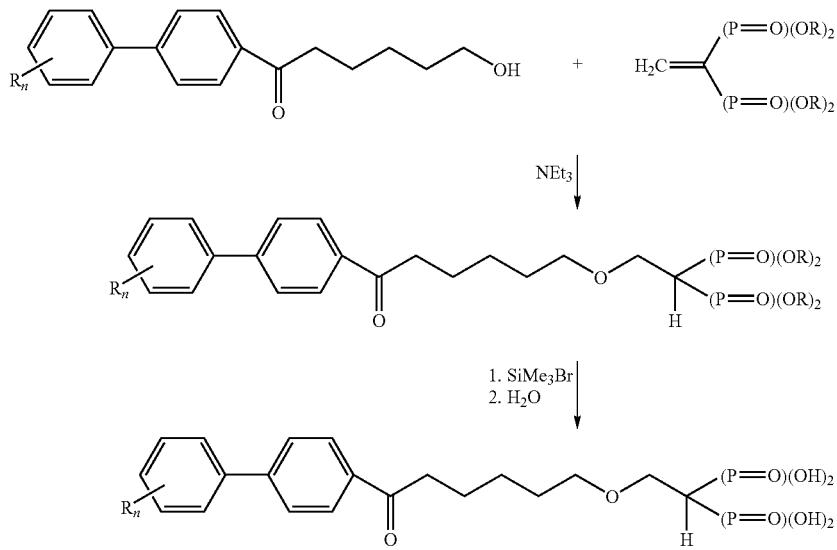

In another method, a suitable aryl hydroxalkyl ketone is heated with triethylorthoformate and diethyl phosphite (HP(=O)(OEt)$_2$) using, for example, the method described by Herczegh et al., 2002. Again, the phosphate ester groups, e.g., ethyl groups, are removed e.g., with trimethylsilylbromide or left in place. An example of such a method is illustrated in the following scheme.

Scheme 18

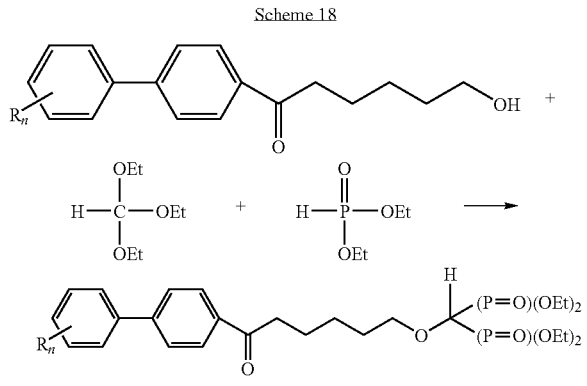

In another method, 1,5-dibromobutane is reacted with triethylphosphite to give diethyl-5-bromopentylphosphonate, for example by the method described by Eberhard and Westheimer, 1965. The resultant bromide is then reacted with magnesium in diethyl ether or tetrahydrofuran, to give the corresponding Grignard reagent. This can be coupled with a suitable Weinreb amide, described above. The phosphate ester groups can then be removed by reflux in concentrated HCl or with trimethylsilylbromide. An example of such a method is illustrated in the following schemes.

Scheme 19

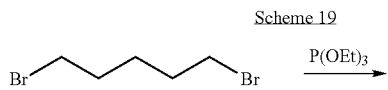

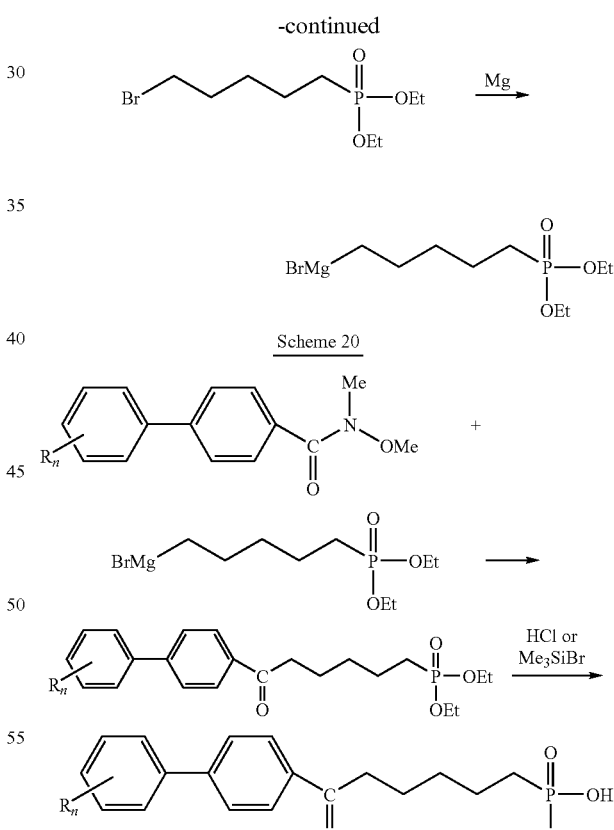

Reduced ketones (e.g., where the —C(=O)— group has been replaced by —CH(OH)—) can be prepared, for example, by reaction of the ketone with a reducing agent, for example, NaBH$_4$, typically before introduction of the terminal hydroxy group. An example of such a method is illustrated in the following scheme.

Scheme 22

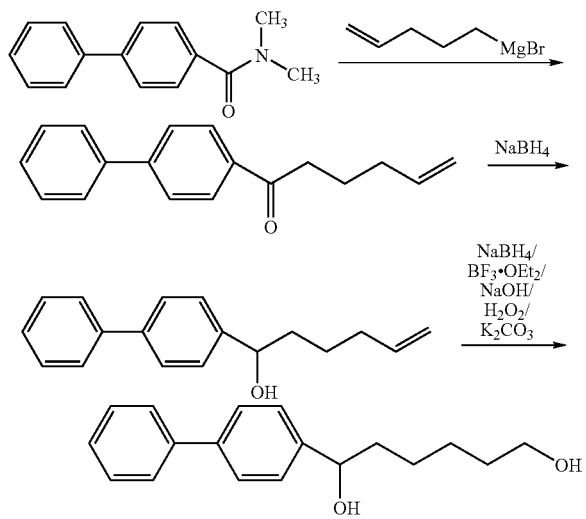

Corresponding derivatives of the hydroxy compound can be prepared, for example, before the introduction of the terminal hydroxy group. For example, the hydroxy group (—CH(OH)—) group may be converted to an ether (e.g., a $C_{1-7}$alkyl ether), for example, by reaction with haloalkane (e.g., bromoalkane) and base (e.g., $K_2CO_3$). An example of such a method is illustrated in the following scheme.

Scheme 22

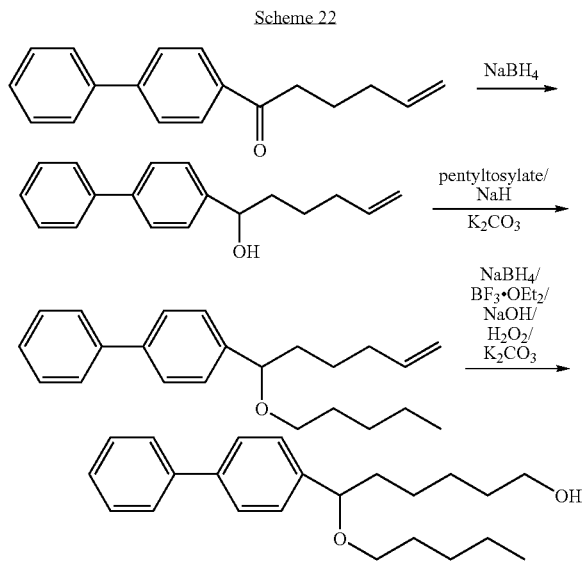

Other derivatives may be prepared, for example, by reaction of the hydroxy group (—CH(OH)—) group with methanesulfonyl chloride (to give a sulfonate); with acetyl chloride (to give an acetate); with iodomethane (e.g., to give a methyl ether); and with benzyl chloride (to give a benzyl ether).

The ketone may also be protected, for example, as a dithiane group, before a subsequent hydroboration step. Subsequent deprotection gives the desired ketone. An example of such a method is illustrated in the following scheme.

Scheme 23

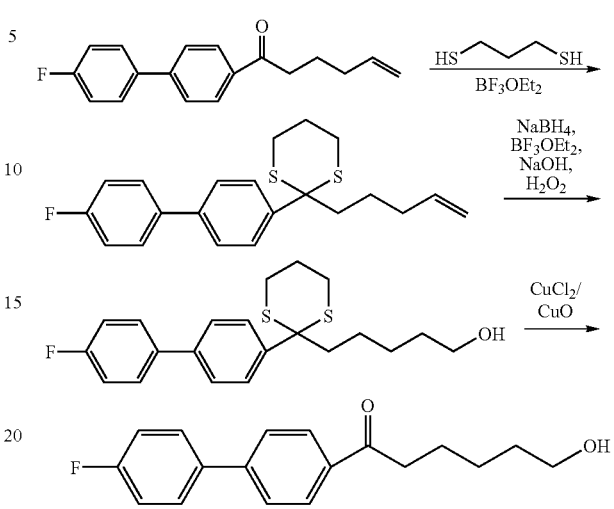

In another approach, the grignard reagent may be reacted directly with an aldehyde and then oxidised to give the dihydroxy derivative. An example of such a method is illustrated in the following scheme.

Scheme 24

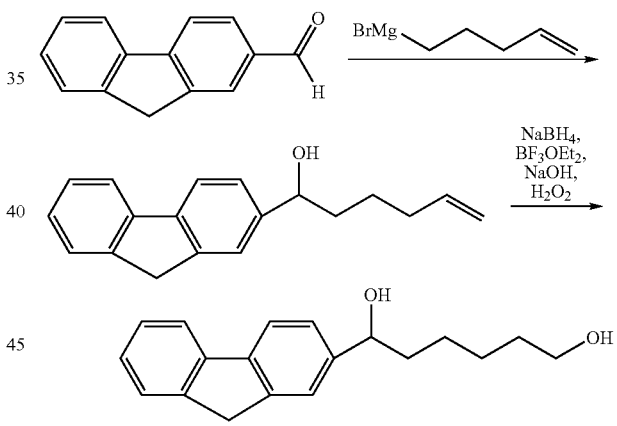

In another approach, a ketone may be reacted directly with an alkene grignard reagent to give the resultant alcohol. Hydroboration produces the di-alcohol. An example of such a method is illustrated in the following scheme.

Scheme 25

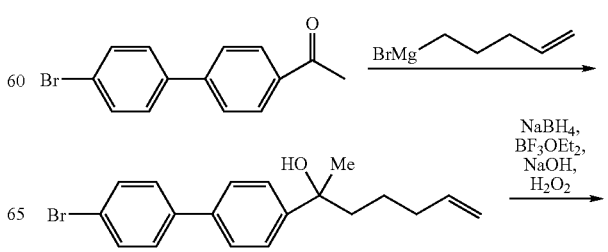

-continued

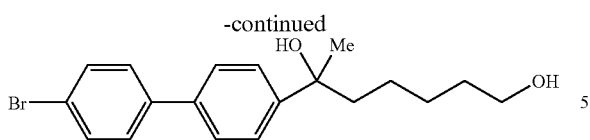

The products may be purified, for example, by column chromatography.

Uses

The present invention provides active compounds, specifically, active ketones and reduced ketones and derivatives thereof, as described herein, which, e.g., inhibit osteoclasts, for example, inhibit of the survival, formation, and/or activity of osteoclasts, and/or which inhibit bone resorption. The compounds may therefore be referred to as "osteoclast inhibitors" and/or "bone resorption inhibitors" and are useful in the treatment of bone conditions, bone disorders, conditions mediated by osteoclasts, conditions characterised by bone resorption, etc., as described herein.

The term "active," as used herein, pertains to compounds which are capable of inhibiting the survival, formation, and/or activity of osteoclasts, and/or inhibiting bone resorption, and specifically includes both compounds with intrinsic activity (drugs) as well as prodrugs of such compounds, which prodrugs may themselves exhibit little or no intrinsic activity.

One of ordinary skill in the art is readily able to determine whether or not a candidate compound inhibits the survival, formation, and/or activity of osteoclasts and/or inhibits bone resorption. For example, suitable methods which may conveniently be used in order to assess the inhibitory effects offered by a particular compound are described in the examples below.

Use in Methods of Inhibition

One aspect of the invention pertains to a method of inhibiting osteoclast survival, formation, and/or activity, in vitro or in vivo, comprising contacting an osteoclast with an effective amount of an active compound, as described herein.

Another aspect of the invention pertains to a method of inhibiting bone resorption, in vitro or in vivo, comprising contacting cells in the bone microenvironment with a therapeutically-effective amount of an active compound, as described herein.

The term "cells in the bone microenvironment," as used herein, pertains to cells such as osteoblasts, osteoclasts, osteocytes and bone marrow stromal cells, which are located in close proximity to bone (e.g., within one hundred micrometers of the bone surface).

Bone Disorders

The compounds of the present invention are also useful in the treatment of bone disorders, for example, conditions mediated by osteoclasts (as "osteoclast inhibitors"), and/or conditions characterised by bone resorption (as "bone resorption inhibitors").

Examples of such conditions include, but are not limited to, the following diseases of the skeleton, including but not limited to, pathologically low bone mineral density, such as:
osteoporosis (including, e.g., steroid induced osteoporosis);
osteopetrosis;
osteoarthritis;
ectopic bone formation;
Paget's disease of bone (osteitis deformans);
rheumatoid arthritis;
hypercalcaemia caused by conditions associated with increased bone resorption, including, but not limited to: vitamin D intoxication, primary or tertiary hyperparathyroidism, immobilisation, and sarcoidosis;
neoplasia of bones, both as a primary tumour and as metastases, including but not limited to, osteosarcoma and osteoma (Zheng et al., 1998, *J. Cell Biochem.*, Vol. 70, p. 121) and cancer associated bone disease (e.g., hypercalcaemia of malignancy, bone metastases, osteolytic bone metastases, multiple myeloma, breast carcinoma);
aseptic loosening of prosthetic implants (e.g., artificial joints, e.g., knees, hips, etc., can loosen due to osteoclast activity driven by local inflammation) (see, e.g., Childs, L. M., et al., 2001, *Journal of Bone and Mineral Research*, Vol. 16, No. 2, pp. 338-347).

In one embodiment, the bone disorder is osteoporosis, rheumatoid arthritis, cancer associated bone disease, Paget's disease, or aseptic loosening of prosthetic implants.

In one embodiment, the bone disorder is osteoporosis (e.g., osteoporosis not associated with inflammation; e.g., osteoporosis associated with a genetic predisposition, sex hormone deficiency, or ageing), cancer associated bone disease, Paget's disease of bone, or aseptic loosening of prosthetic implants.

In one embodiment, the bone disorder is osteoporosis (e.g., osteoporosis not associated with inflammation and/or osteoporosis associated with a genetic predisposition, sex hormone deficiency, or ageing).

Inflammation/Immune Disorders

The compounds of the present invention have also macrophage inhibitory effects, and so are useful in the treatment of conditions associated with inflammation or activation of the immune system.

Examples of such conditions include, but are not limited to, the following:

Diseases with an inflammatory or autoimmune component, including allergic diseases, such as atopy, allergic rhinitis, atopic dermatitis, anaphylaxis, allergic bronchopulmonary aspergillosis, and hypersensitivity pneumonitis (pigeon breeders disease, farmer's lung disease, humidifier lung disease, malt workers' lung disease); allergies, including flea allergy dermatitis in mammals such as domestic animals, e.g., dogs and cats, contact allergens including mosquito bites or other insect sting allergies, poison ivy, poison oak, poison sumac, or other skin allergens; autoimmune disorders, including, but not limited to, type I diabetes, Crohn's disease, multiple sclerosis, arthritis, rheumatoid arthritis (Ogata et at., 1997, *J. Pathol.*, Vol. 182, p. 106); Gong et al., 1997, *J. Exp. Med.*, Vol 186, p. 131), systemic lupus erythematosus, autoimmune (Hasimoto's) thyroiditis, autoimmune liver diseases such as hepatitis and primary biliary cirrhosis, hyperthyroidism (Graves' disease; thyrotoxicosis), insulin-resistant diabetes, autoimmune adrenal insufficiency (Addison's disease), autoimmune oophoritis, autoimmune orchitis, autoimmune hemolytic anemia, paroxysmal cold hemoglobinuria, Behcet's disease, autoimmune thrombocytopenia, autoimmune neutropenia, pernicious anemia, pure red cell anemia, autoimmune coagulopathies, myasthenia gravis, experimental allergic encephalomyelitis, autoimmune polyneuritis, pemphigus and other bullous diseases, rheumatic carditis, Goodpasture's syndrome, postcardiotomy syndrome, Sjogren's syndrome, polymyositis, dermatomyositis, and scleroderma; disease states resulting from inappropriate inflammation, either local or systemic, for example, irritable or inflammatory bowel syndrome (Mazzucchelli et al., 1996, *J. Pathol.*, Vol. 178, p. 201), skin diseases such as psoriasis and lichen planus, delayed type hypersensitivity, chronic pulmonary inflammation, e.g., pulmonary alveolitis and pulmonary granuloma, gingival inflammation or other periodontal disease, and osseous inflammation associated with lesions of endodontic origin (Volejnikova et al., 1997, *Am. J. Pathol.*, Vol. 150, p. 1711), hypersensitivity lung diseases such as hypersensitivity pneumonitis (Sugiyama et al., 1995, *Eur. Respir. J.*, Vol. 8, p. 1084), and inflammation related to histamine release from basophils (Dvorak et al., 1996, *J. Allergy Clin. Immunol.*, Vol. 98, p. 355), such as hay fever, histamine release from mast cells (Galli et al., 1989, *Ciba Foundation Symposium*, Vol. 147, p. 53), or mast cell tumors, types of type 1 hypersensitivity reactions (anaphylaxis, skin allergy, hives, allergic rhinitis, and allergic gastroenteritis); ulcerative colitis.

Use in Methods of Therapy

Another aspect of the present invention pertains to an active compound as described herein for use in a method of treatment of the human or animal body by therapy.

In one embodiment, the treatment is treatment of a bone disorder, for example, a condition mediated by osteoclasts and/or characterised by bone resorption, as described herein.

In one embodiment, the treatment is treatment of a condition mediated by osteoclasts, as described herein.

In one embodiment, the treatment is treatment of a condition characterised by bone resorption, as described herein.

In one embodiment, the treatment is treatment of osteoporosis, rheumatoid arthritis, cancer associated bone disease, Paget's disease, or aseptic loosening of prosthetic implants.

In one embodiment, the treatment is treatment of a condition associated with inflammation or activation of the immune system, as described herein.

Use in the Manufacture of Medicaments

Another aspect of the present invention pertains to use of an active compound, as described herein, in the manufacture of a medicament for use in treatment.

In one embodiment, the treatment is treatment of a bone disorder, for example, a condition mediated by osteoclasts and/or characterised by bone resorption, as described herein.

In one embodiment, the treatment is treatment of a condition mediated by osteoclasts, as described herein.

In one embodiment, the treatment is treatment of a condition characterised by bone resorption, as described herein.

In one embodiment, the treatment is treatment of osteoporosis, rheumatoid arthritis, cancer associated bone disease, Paget's disease, or aseptic loosening of prosthetic implants.

In one embodiment, the treatment is treatment of a condition associated with inflammation or activation of the immune system, as described herein.

Methods of Treatment

Another aspect of the present invention pertains to a method of treatment comprising administering to a patient in need of treatment a therapeutically effective amount of an active compound as described herein, preferably in the form of a pharmaceutical composition.

In one embodiment, the treatment is treatment of a bone disorder, for example, a condition mediated by osteoclasts and/or characterised by bone resorption, as described herein.

In one embodiment, the treatment is treatment of a condition mediated by osteoclasts, as described herein.

In one embodiment, the treatment is treatment of a condition characterised by bone resorption, as described herein.

In one embodiment, the treatment is treatment of osteoporosis, rheumatoid arthritis, cancer associated bone disease, Paget's disease, or aseptic loosening of prosthetic implants.

In one embodiment, the treatment is treatment of a condition associated with inflammation or activation of the immune system, as described herein.

Treatment

The term "treatment," as used herein in the context of treating a condition, pertains generally to treatment and therapy, whether of a human or an animal (e.g., in veterinary applications), in which some desired therapeutic effect is achieved, for example, the inhibition of the progress of the condition, and includes a reduction in the rate of progress, a halt in the rate of progress, amelioration of the condition, and cure of the condition. Treatment as a prophylactic measure (i.e., prophylaxis) is also included. For example, use with perimenopausal women who may not yet have osteoporosis, but who are at risk of osteoporosis, is encompassed by the term "treatment."

The term "therapeutically-effective amount," as used herein, pertains to that amount of an active compound, or a material, composition or dosage from comprising an active compound, which is effective for producing some desired therapeutic effect, commensurate with a reasonable benefit/risk ratio, when administered in accordance with a desired treatment regimen.

The term "treatment" includes combination treatments and therapies, in which two or more treatments or therapies are combined, for example, sequentially or simultaneously. Examples of treatments and therapies include, but are not limited to, chemotherapy (the administration of active agents, including, e.g., drugs, antibodies (e.g., as in immunotherapy), prodrugs (e.g., as in photodynamic therapy, GDEPT, ADEPT, etc.); surgery; radiation therapy; and gene therapy.

Other Uses

Active compounds may also be used as cell culture additives to inhibit osteoclasts, for example, to inhibit the survival, formation, and/or activity of osteoclasts.

Active compounds may also be used as part of an in vitro assay, for example, in order to determine whether a candidate host is likely to benefit from treatment with the compound in question.

Active compounds may also be used as a standard, for example, in an assay, in order to identify other active compounds, other osteoclast inhibitors, etc.

Kits

One aspect of the invention pertains to a kit comprising (a) an active compound as described herein, or a composition comprising an active compound as described herein, e.g., preferably provided in a suitable container and/or with suitable packaging; and (b) instructions for use, e.g., written instructions on how to administer the active compound or composition.

The written instructions may also include a list of indications for which the active ingredient is a suitable treatment.

Routes of Administration

The active compound or pharmaceutical composition comprising the active compound may be administered to a subject by any convenient route of administration, whether systemically/peripherally or topically (i.e., at the site of desired action).

Routes of administration include, but are not limited to, oral (e.g., by ingestion); buccal; sublingual; transdermal (including, e.g., by a patch, plaster, etc.); transmucosal (including, e.g., by a patch, plaster, etc.); intranasal (e.g., by nasal spray); ocular (e.g., by eyedrops); pulmonary (e.g., by inhalation or insufflation therapy using, e.g., via an aerosol, e.g., through the mouth or nose); rectal (e.g., by suppository or enema); vaginal (e.g., by pessary); parenteral, for example, by injection, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, and intrasternal; by implant of a depot or reservoir, for example, subcutaneously or intramuscularly.

The Subject/Patient

The subject/patient may be a chordate, a vertebrate, a mammal, a bird, a reptile (e.g., snakes, lizards, crocodiles), an amphibian (e.g., frogs, toads), a bony fish (e.g., salmon, plaice, eel, lungfish), a cartilaginous fish (e.g., sharks, rays), or a jawless fish (e.g., lampreys, hagfish).

The subject/patient may be a mammal, a placental mammal, a marsupial (e.g., kangaroo, wombat), a monotreme (e.g., duckbilled platypus), a rodent (e.g., a guinea pig, a hamster, a rat, a mouse), murine (e.g., a mouse), a lagomorph (e.g., a rabbit), avian (e.g., a bird), canine (e.g., a dog), feline (e.g., a cat), equine (e.g., a horse), porcine (e.g., a pig), ovine (e.g., a sheep), bovine (e.g., a cow), a primate, simian (e.g., a monkey or ape), a monkey (e.g., marmoset, baboon), an ape (e.g., gorilla, chimpanzee, orangutang, gibbon), or a human.

Furthermore, the subject/patient may be any of its forms of development, for example, a foetus.

In one preferred embodiment, the subject/patient is a human.

Formulations

While it is possible for the active compound to be administered alone, it is preferable to present it as a pharmaceutical formulation (e.g., composition, preparation, medicament) comprising at least one active compound, as defined above, together with one or more other pharmaceutically acceptable ingredients well known to those skilled in the art, including, but not limited to, pharmaceutically acceptable carriers, diluents, excipients, adjuvants, fillers, buffers, preservatives, antioxidants, lubricants, stabilisers, solubilisers, surfactants (e.g., wetting agents), masking agents, colouring agents, flavouring agents, and sweetening agents. The formulation may further comprise other active agents, for example, other therapeutic or prophylactic agents.

Thus, the present invention further provides pharmaceutical compositions, as defined above, and methods of making a pharmaceutical composition comprising admixing at least one active compound, as defined above, together with one or more other pharmaceutically acceptable ingredients well known to those skilled in the art, e.g., carriers, diluents, excipients, etc. If formulated as discrete units (e.g., tablets, etc.), each unit contains a predetermined amount (dosage) of the active compound.

The term "pharmaceutically acceptable" as used herein pertains to compounds, ingredients, materials, compositions, dosage forms, etc., which are, within the scope of sound medical judgment, suitable for use in contact with the tissues of the subject in question (e.g., human) without excessive toxicity, irritation, allergic response, or other problem or complication, commensurate with a reasonable benefit/risk ratio. Each carrier, diluent, excipient, etc. must also be "acceptable" in the sense of being compatible with the other ingredients of the formulation.

Suitable carriers, diluents, excipients, etc. can be found in standard pharmaceutical texts, for example, *Remington's Pharmaceutical Sciences,* 18th edition, Mack Publishing Company, Easton, Pa., 1990; and *Handbook of Pharmaceutical Excipients,* 2nd edition, 1994.

The formulations may be prepared by any methods well known in the art of pharmacy. Such methods include the step of bringing into association the active compound with a carrier which constitutes one or more accessory ingredients. In general, the formulations are prepared by uniformly and intimately bringing into association the active compound with carriers (e.g., liquid carriers, finely divided solid carrier, etc.), and then shaping the product, if necessary.

The formulation may be prepared to provide for rapid or slow release; immediate, delayed, timed, or sustained release; or a combination thereof.

Formulations may suitably be in the form of liquids, solutions (e.g., aqueous, non-aqueous), suspensions (e.g., aqueous, non-aqueous), emulsions (e.g., oil-in-water, water-in-oil), elixirs, syrups, electuaries, mouthwashes, drops, tablets (including, e.g., coated tablets), granules, powders, lozenges, pastilles, capsules (including, e.g., hard and soft gelatin capsules), cachets, pills, ampoules, boluses, suppositories, pessaries, tinctures, gels, pastes, ointments, creams, lotions, oils, foams, sprays, mists, or aerosols.

Formulations may suitably be provided as a patch, adhesive plaster, bandage, dressing, or the like which is impregnated with one or more active compounds and optionally one or more other pharmaceutically acceptable ingredients, including, for example, penetration, permeation, and absorption enhancers. Formulations may also suitably be provided in the form of a depot or reservoir.

The active compound may be dissolved in, suspended in, or admixed with one or more other pharmaceutically acceptable ingredients. The active compound may be presented in a liposome or other microparticulate which is designed to target the active compound, for example, to blood components or one or more organs.

Formulations suitable for oral administration (e.g., by ingestion) include liquids, solutions (e.g., aqueous, non-aqueous), suspensions (e.g., aqueous, non-aqueous), emulsions (e.g., oil-in-water, water-in-oil), elixirs, syrups, electuaries, tablets, granules, powders, capsules, cachets, pills, ampoules, boluses.

Formulations suitable for buccal administration include mouthwashes, lozenges, pastilles, as well as patches, adhesive plasters, depots, and reservoirs. Losenges typically comprise the active compound in a flavored basis, usually sucrose and acacia or tragacanth. Pastilles typically comprise the active compound in an inert matrix, such as gelatin and glycerin, or sucrose and acacia. Mouthwashes typically comprise the active compound in a suitable liquid carrier.

Formulations suitable for sublingual administration include tablets, lozenges, pastilles, capsules, and pills.

Formulations suitable for oral transmucosal administration include liquids, solutions (e.g., aqueous, non-aqueous), suspensions (e.g., aqueous, non-aqueous), emulsions (e.g., oil-in-water, water-in-oil), mouthwashes, lozenges, pastilles, as well as patches, adhesive plasters, depots, and reservoirs.

Formulations suitable for non-oral transmucosal administration include liquids, solutions (e.g., aqueous, non-aqueous), suspensions (e.g., aqueous, non-aqueous), emulsions (e.g., oil-in-water, water-in-oil), suppositories, pessaries, gels, pastes, ointments, creams, lotions, oils, as well as patches, adhesive plasters, depots, and reservoirs.

Formulations suitable for transdermal administration include gels, pastes, ointments, creams, lotions, and oils, as well as patches, adhesive plasters, bandages, dressings, depots, and reservoirs.

Tablets may be made by conventional means, e.g., compression or moulding, optionally with one or more accessory ingredients. Compressed tablets may be prepared by compressing in a suitable machine the active compound in a free-flowing form such as a powder or granules, optionally mixed with one or more binders (e.g., povidone, gelatin, acacia, sorbitol, tragacanth, hydroxypropylmethyl cellulose); fillers or diluents (e.g., lactose, microcrystalline cellulose, calcium hydrogen phosphate); lubricants (e.g., magnesium stearate, talc, silica); disintegrants (e.g., sodium starch glycolate, cross-linked povidone, cross-linked sodium carboxymethyl cellulose); surface-active or dispersing or wetting agents (e.g., sodium lauryl sulfate); preservatives (e.g., methyl p-hydroxybenzoate, propyl p-hydroxybenzoate, sorbic acid); flavours, flavour enhancing agents, and sweeteners. Moulded tablets may be made by moulding in a suitable machine a mixture of the powdered compound moistened with an inert liquid diluent. The tablets may optionally be coated or scored and may be formulated so as to provide slow or controlled release of the active compound therein using, for example, hydroxypropylmethyl cellulose in varying proportions to provide the desired release profile. Tablets may optionally be provided with a coating, for example, to affect release, for example an enteric coating, to provide release in parts of the gut other than the stomach.

Ointments are typically prepared from the active compound and a paraffinic or a water-miscible ointment base.

Creams are typically prepared from the active compound and an oil-in-water cream base. If desired, the aqueous phase of the cream base may include, for example, at least about 30% w/w of a polyhydric alcohol, i.e., an alcohol having two or more hydroxyl groups such as propylene glycol, butane-1, 3-diol, mannitol, sorbitol, glycerol and polyethylene glycol and mixtures thereof. The topical formulations may desirably include a compound which enhances absorption or penetration of the active compound through the skin or other affected areas. Examples of such dermal penetration enhancers include dimethylsulfoxide and related analogues.

Emulsions are typically prepared from the active compound and an oily phase, which may optionally comprise merely an emulsifier (otherwise known as an emulgent), or it may comprises a mixture of at least one emulsifier with a fat or an oil or with both a fat and an oil. Preferably, a hydrophilic emulsifier is included together with a lipophilic emulsifier which acts as a stabiliser. It is also preferred to include both an oil and a fat. Together, the emulsifier(s) with or without stabiliser(s) make up the so-called emulsifying wax, and the wax together with the oil and/or fat make up the so-called emulsifying ointment base which forms the oily dispersed phase of the cream formulations.

Suitable emulgents and emulsion stabilisers include Tween 60, Span 80, cetostearyl alcohol, myristyl alcohol, glyceryl monostearate and sodium lauryl sulphate. The choice of suitable oils or fats for the formulation is based on achieving the desired cosmetic properties, since the solubility of the active compound in most oils likely to be used in pharmaceutical emulsion formulations may be very low. Thus the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

Formulations suitable for intranasal administration, where the carrier is a liquid, include, for example, nasal spray, nasal drops, or by aerosol administration by nebuliser, include aqueous or oily solutions of the active compound.

Formulations suitable for intranasal administration, where the carrier is a solid, include, for example, those presented as a coarse powder having a particle size, for example, in the range of about 20 to about 500 microns which is administered in the manner in which snuff is taken, i.e., by rapid inhalation through the nasal passage from a container of the powder held close up to the nose.

Formulations suitable for pulmonary administration (e.g., by inhalation or insufflation therapy) include those presented as an aerosol spray from a pressurised pack, with the use of a suitable propellant, such as dichlorodifluoromethane, trichlorofluoromethane, dichoro-tetrafluoroethane, carbon dioxide, or other suitable gases.

Formulations suitable for ocular administration include eye drops wherein the active compound is dissolved or suspended in a suitable carrier, especially an aqueous solvent for the active compound.

Formulations suitable for rectal administration may be presented as a suppository with a suitable base comprising, for example, natural or hardened oils, waxes, fats, semi-liquid or liquid polyols, for example, cocoa butter or a salicylate; or as a solution or suspension for treatment by enema.

Formulations suitable for vaginal administration may be presented as pessaries, tampons, creams, gels, pastes, foams or spray formulations containing in addition to the active compound, such carriers as are known in the art to be appropriate.

Formulations suitable for parenteral administration (e.g., by injection), include aqueous or non-aqueous, isotonic, pyrogen-free, sterile liquids (e.g., solutions, suspensions), in which the active compound is dissolved, suspended, or otherwise provided (e.g., in a liposome or other microparticulate). Such liquids may additional contain other pharmaceutically acceptable ingredients, such as anti-oxidants, buffers, preservatives, stabilisers, bacteriostats, suspending agents, thickening agents, and solutes which render the formulation isotonic with the blood (or other relevant bodily fluid) of the intended recipient. Examples of excipients include, for example, water, alcohols, polyols, glycerol, vegetable oils, and the like. Examples of suitable isotonic carriers for use in such formulations include Sodium Chloride Injection, Ringer's Solution, or Lactated Ringer's Injection. Typically, the concentration of the active compound in the liquid is from about 1 ng/ml to about 10 μg/ml, for example from about 10 ng/ml to about 1 μg/ml. The formulations may be presented in unit-dose or multi-dose sealed containers, for example, ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules, and tablets.

Dosage

It will be appreciated by one of skill in the art that appropriate dosages of the active compounds, and compositions comprising the active compounds, can vary from patient to patient. Determining the optimal dosage will generally involve the balancing of the level of therapeutic benefit against any risk or deleterious side effects. The selected dosage level will depend on a variety of factors including, but not limited to, the activity of the particular compound, the route of administration, the time of administration, the rate of excretion of the compound, the duration of the treatment, other drugs, compounds, and/or materials used in combination, the severity of the condition, and the species, sex, age, weight, condition, general health, and prior medical history of the patient. The amount of compound and route of administration will ultimately be at the discretion of the physician, veterinarian, or clinician, although generally the dosage will be selected to achieve local concentrations at the site of action which achieve the desired effect without causing substantial harmful or deleterious side-effects.

Administration can be effected in one dose, continuously or intermittently (e.g., in divided doses at appropriate intervals) throughout the course of treatment. Methods of determining the most effective means and dosage of administration are well known to those of skill in the art and will vary with the formulation used for therapy, the purpose of the therapy, the target cell(s) being treated, and the subject being treated. Single or multiple administrations can be carried out with the dose level and pattern being selected by the treating physician, veterinarian, or clinician.

In general, a suitable dose of the active compound is in the range of about 100 μg to about 250 mg (more typically about 100 μg to about 25 mg) per kilogram body weight of the subject per day. Where the active compound is a salt, an ester, an amide, a prodrug, or the like, the amount administered is calculated on the basis of the parent compound and so the actual weight to be used is increased proportionately.

EXAMPLES

The following are examples are provided solely to illustrate the present invention and are not intended to limit the scope of the invention, as described herein.

Example 1

4-(t-Butyldiphenylsiloxy)-pentanol (ABD-64)

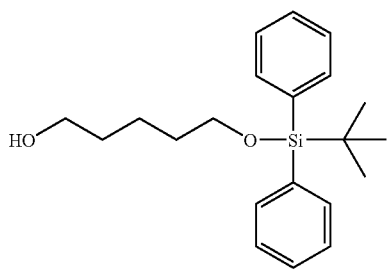

Pentanediol (20 g, 0.2 mol) was dissolved in pyridine (50 mL) and tertiary-butylchlorodiphenylsilane (14 g, 0.05 mol) was added dropwise. A catalytic quantity (0.1 g) of dimethylaminopyridine (DMAP) was added and the mixture stirred at room temperature for 3 days. The mixture was dissolved in methylene chloride and washed with water (100 mL), 2 M HCl (3×100 mL), and water. The organic phase was dried over $Na_2SO_4$, evaporated to a pale oil and purified by column chromatography (light petroleum:ethyl acetate, 2:1) to give the title compound as a clear oil (yield 90%). $\delta_C$ (CDCl$_3$, 62.9 MHz): 19.2, 22.0, 26.9, 32.3, 32.5, 62.9, 63.8, 127.6, 129.6, 134.1 and 135.6

Example 2

4-(t-Butyldiphenylsiloxy)pentyl-p-toluene sulfonate (ABD-65)

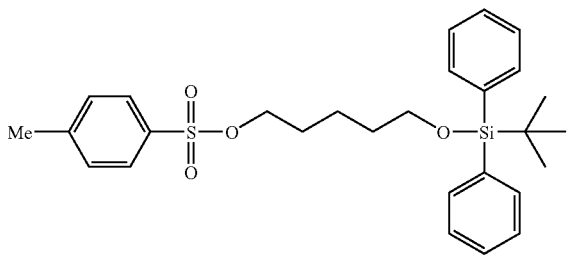

4-(t-Butyldiphenylsiloxy)-pentanol (15 g, 0.04 mol) was dissolved in methylene chloride (100 mL) containing pyridine (7 g). Tosyl chloride (15.3 g, 0.08 mol) was added slowly and the mixture stirred overnight. The mixture was washed with saturated $NaHCO_3$ (2×100 mL) and the aqueous then backwashed with methylene chloride (100 mL). The organic phases were combined and washed with 2M HCl (100 mL) and water. The solution was dried over $Na_2SO_4$, evaporated and purified by column chromatography (light petroleum: ethyl acetate, 3:1) to give the title compound as a thick oil (yield 85%). $\delta_C$ (CDCl$_3$, 62.9 MHz): 19.2, 21.7, 21.8, 26.9, 28.6, 31.8, 63.5, 70.6, 127.7, 127.9, 129.6, 129.9, 133.2, 133.9, 135.6 and 144.7

Example 3

2,2-[4-Biphenyl-5-(t-butyldiphenylsiloxy)pentyl)]-1,3-propanedithiane (ABD-66)

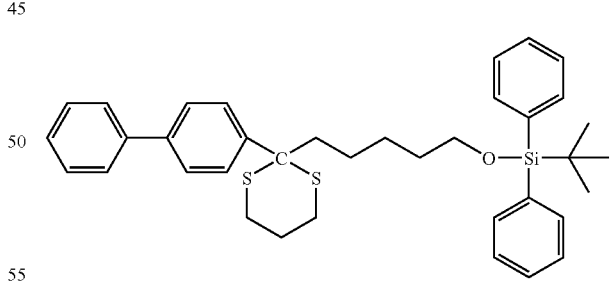

Dry hydrogen chloride was bubbled through a solution of 1,3 propanedithiol (10 ml, 0.1 mol) and biphenylcarboxaldehyde (18 g, 0.1 mol) in chloroform (70 mL) until the mixture was saturated (5 minutes). The mixture was left to stand for 30 minutes and then washed with $H_2O$, 10% KOH and $H_2O$. The organic phase was filtered through $Na_2SO_4$ and evaporated. Crystallisation from methanol gave biphenyl-2-(1,3 dithiane). The biphenyl dithiane (2.72 g, 0.01 mol) was suspended in anhydrous tetrahydrafuran (20 mL) and cooled to below −50° C. in dry ice/acetone. The reaction flask was fitted with a septum and flushed with nitrogen. Butyl lithium (6.25 ml, 1.6 M solution in hexane) was added slowly under $N_2$ to the vigorously stirred mixture. 4-(t-Butyldiphenylsiloxy)pentyl-p-toluene sulfonate (4.92 g, 0.01 mol) was dissolved in tetrahydrafuran (8 mL) and the solution added to the reaction vessel using a syringe. The reaction was allowed to warm to room temperature and stirring continued for 24 hour. The mixture was poured into water (100 ml) and extracted with pentane (3×70 mL) to give a yellow solution. The aqueous was extracted again with methylene chloride (100 mL), the organic extracts combined, washed with saturated $NaHCO_3$ solution and dried over $Na_2SO_4$. The solvents were evaporated and the product purified by column chromatography (slow elution with hexane) to give the title compound as a yellow solid (yield 55%). $\delta_C$ (CDCl$_3$, 62.9 MHz): 19.2, 23.7, 25.4, 26.9, 27.7, 32.3, 45.3, 59.0, 63.8, 127.1, 127.2, 127.4, 127.6, 128.8, 129.4, 129.5, 134.1, 135.6, 139.5, 140.6 and 141.1.

Example 4

2,2-[4-Biphenyl-(5-hydroxypentyl)]-1,3-propanedithiane (ABD-67)

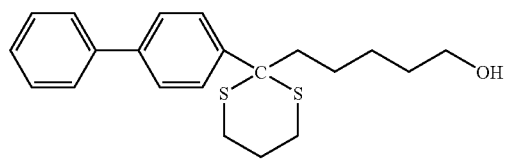

The silyl group of 2,2-[4-biphenyl-5-(t-butyldiphenylsiloxy)pentyl]-1,3-propanedithiane was removed by dissolving the yellow solid (2 g) in tertiarybutylammonium fluoride (15 mL of 1 M in tetrahydrafuran) and stirring for 30 minutes. The solvent was evaporated and the residue dissolved in methylene chloride, washed with water and dried over $Na_2SO_4$. The product was purified by column chromatography (ethyl acetate: light petroleum, 2:1 followed by repetition using 1:1) to give the title compound as a thick oil (yield 85%). $\delta_C$ (CDCl$_3$, 62.9 MHz): 23.7, 25.3, 25.7, 27.7, 32.4, 45.2, 58.9, 62.7, 127.0, 127.1, 127.4, 128.8, 129.3, 139.6, 140.5 and 141.0.

Example 5

6-Hydroxy-1-(4-biphenyl)hexan-1-one (ABD-68)

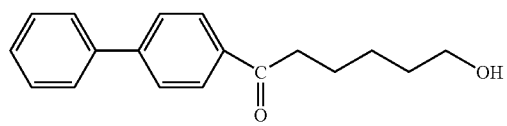

2,2-[4-Biphenyl-(5-hydroxypentyl)]-1,3-propanedithiane (1.5 g) was dissolved in 1% aqueous acetone (30 mL). Anhydrous $CuCl_2$ (1.35 g, 10 mmol) and CuO (1.6 g, 20 mmol) were added and the mixture refluxed for 1 hour. The residue was filtered and washed with acetone. Evaporation of the filtrates gave a brown solid. This was extracted with diethyl ether followed by methylene chloride. The organic phases were combined, evaporated and purified by column chromatography (ethyl acetate: light petroleum 1:1) to give the title compound as a white solid (yield 45%). $\delta_C$ (CDCl$_3$, 62.9 MHz): 24.0, 25.5, 32.5, 38.5, 62.7, 127.3, 128.3, 128.7, 129.0, 135.7, 139.9, 145.7 and 200.1.

Example 6

1-(4'-Fluoro-biphenyl-4-yl)-ethanone

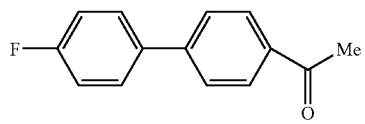

4'-Fluoro-biphenyl (0.03 mol) was added to 1 M $AlCl_3$ in nitrobenzene (40 mL, 0.04 mol) with chilling in an ice bath. Acetyl chloride (0.06 mol) was added dropwise and the mixture stirred overnight at room temperature. The dark solution was poured into a mixture of crushed ice (150 mL), water (25 mL) and HCl (50 mL). The aqueous phase was separated and the nitrobenzene removed by steam distillation to give a dark low melting solid. The solid was recrystallised from aqueous methanol to give the title compound. $\delta_C$ (CDCl$_3$, 62.9 MHz): 26.7, 115.9 (d, J 21.5), 127.1, 129.0 (d, J=7.8), 135.8, 136.0 (d, J 2.9), 144.7, 163.0 (d, J 248.0) and 197.8.

Example 7

1-(4'-Methoxy-biphenyl-4-yl)-ethanone

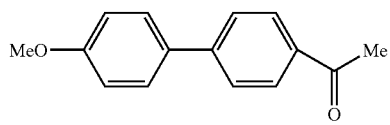

The 4'-methoxybiphenyl (0.05 mol) and $AlCl_3$ (0.06 mol) were dissolved in boiling $CS_2$ (60 mL) with stirring. Acetyl chloride (0.1 mol) was added dropwise and reflux continued for 1 hour. The mixture was poured onto crushed ice (150 mL) containing water (50 mL) and HCl (50 mL). The organic phase was separated and the $CS_2$ removed by distillation. The residue was recrystallised from aqueous isopropanol to give the title compound. $\delta_C$ (CDCl$_3$, 62.9 MHz): 26.6, 55.4, 114.4, 126.6, 128.4, 129.0, 132.2, 135.3, 145.4, 159.9 and 198.0

Example 8

4'-Fluoro-biphenyl-4-carboxylic acid

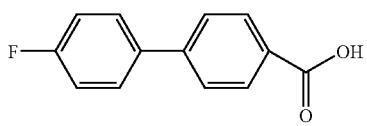

NaOH (7 g) was dissolved in water (25 mL) and cooled in an ice bath. Bromine (7.8 g) was added dropwise to give a solution of NaOBr. 1-(4'-Fluoro-biphenyl-4-yl)-ethanone (0.01 mol) was dissolved in dioxane (35 mL) and warmed to 50° C. in a water bath. The NaOBr solution was added slowly to the stirred solution of the biphenyl acetate and stirring continued at 50° C. for a further 20 minutes. The solution was allowed to cool and a solution of sodium metabisulphite (8 g in 40 mL water) was added followed by water (170 mL). 50 mL of the liquid was evaporated under reduced pressure with heating. The remainder was acidified with HCl (5 mL) and a white precipitate formed upon cooling. The precipitate was filtered and recrystallised from acetic acid to give the title compound. $\delta_C$ (CDCl$_3$, 62.9 MHz): 115.9, 126.8, 129.2, 129.6, 129.8 (d, J 2.9), 135.5 (d, J 2.9), 143.2, 162.4 (d, J 245.1) and 167.2.

Example 9

4'-Fluorobiphenyl-4-carbonyl chloride

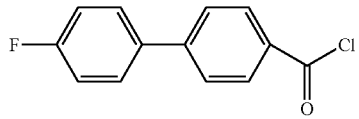

4'-Fluorobiphenyl carboxylate (10 mmol) was dissolved in thionyl chloride (30 mL) and refluxed for 3 hours. The mixture was poured into acetic acid (100 mL) and left to stand until bubbling ceased. Volatile components were removed under vacuum and the mixture left to crystallise overnight. The title compound was collected by filtration.

Example 10

Biphenyl-4-carboxylic acid methoxy-methyl amide (ABD-132)

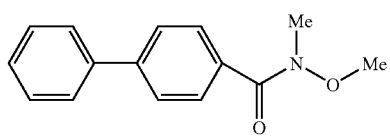

4-Biphenylcarbonyl chloride (8 g) was suspended in chloroform (30 mL). This was added dropwise to a stirred solution of N,O-dimethyl hydroxylamine hydrochloride (5.2 g) and triethylamine (13.5 mL) in chloroform (80 mL) at 0° C. After addition was complete, the mixture was allowed to warm to room temperature and was stirred for a further 30 minutes. The organic phase was separated, washed with water and dried over MgSO$_4$. Evaporation gave an oil, purified by flash column chromatography (ethyl acetate: light petroleum, 1:1) to give the title compound as a white solid. $\delta_C$ (CDCl$_3$, 62.9 MHz): 33.8, 61.1, 126.7, 127.2, 127.9, 128.9, 132.8, 140.2, 143.4 and 169.7. $\delta_H$ (CDCl$_3$, 250 MHz): 3.38 (3H, s), 3.59 (3H, s), 7.37-7.48 (3H, m), 7.61 (4H, m) and 7.77 (2H, d, J 8.5).

Example 11

Pentylmagnesium Bromide

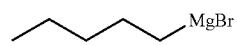

Bromopentane (2.5 g) was dissolved in tetrahydrofuran (20 mL). Magnesium (0.5 g) was added and the mixture gently heated until an exothermic reaction commenced. The mixture was allowed to boil until reaction finished, to give the title compound.

Example 12

1-Biphenyl-4-yl-hexan-1-one (ABD-133)

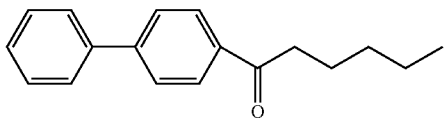

The Weinreb amide (biphenyl-4-carboxylic acid methoxymethyl amide) (1.5 g) was dissolved in tetrahydrofuran (20 mL) and cooled to 0° C. The Grignard reagent was added dropwise with stirring. The mixture was allowed to warm to room temperature and stirred for 1.5 hours. The solvent was evaporated and the residue purified by column chromatography (light petroleum:ethyl acetate, 5:1) to give the title compound as a white solid. $\delta_C$ (CDCl$_3$, 62.9 MHz): 14.0, 22.6, 24.2, 31.6, 38.7, 127.2, 127.3, 128.2, 128.7, 129.0, 135.8, 140.0, 145.6 and 200.2. $\delta_H$ (CDCl$_3$, 250 MHz): 0.92 (3H, t, J 7.3), 1.38 (4H, m), 1.77 (2H, m), 2.98 (2H, t, J 7.3), 7.39-7.47 (3H, m), 7.62 (2H, d, J 7.0), 7.67 (2H, d, J 8.5) and 8.03 (2H, d, J 8.2).

Example 13

4-Bromobutanol

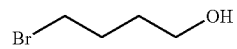

48% Hydrobromic acid (60 mL) was added to refluxing tetrahydrafuran (135 mL) over a period of 30 minutes. Reflux was continued for a further 4 hours. The solution was allowed to cool and excess HBr neutralized with Na$_2$CO$_3$. The organic phase was separated, washed with brine and dried over MgSO$_4$. Evaporation of the solvent gave the title compound as a clear oil (Yield 25 g).

Example 14

5-Bromopentanol

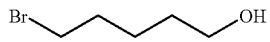

The title compound was obtained using the method of the previous example, using tetrahydropyran to give a brown oil (yield 8.5 g).

Example 15

2-(5-Bromo-pentyloxy)-tetrahydro-pyran

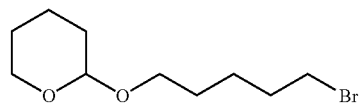

5-bromopentanol (8 g) was dissolved in dichloromethane (100 mL) and was chilled in an ice bath. Dihydropyran (9 g) was added dropwise followed by p-Toluene sulfonic acid monohydrate (1 g). The mixture was allowed to slowly warm to room temperature and stirred for 18 hours. The mixture was diluted with 200 mL ether, washed with 10% NaOH (100 mL) and dried over $MgSO_4$ to give the title compound. $\delta_C$ ($CDCl_3$, 62.9 MHz): 19.7, 25.0, 25.5, 28.9, 30.7, 32.6, 33.7, 62.4, 67.2 and 89.9.

Example 16

2-(5-Bromo-butyloxy)-tetrahydro-pyran

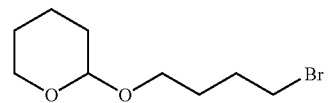

The title compound was obtained using the method of the previous example, using 4-bromobutanol.

Example 17

2-(5-Bromo-pentyloxy)-tetrahydro-pyran magnesium

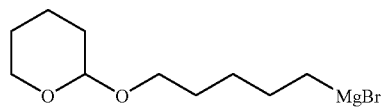

The title compound, a grignard reagent, was prepared from 2-(5-Bromo-pentyloxy)-tetrahydro-pyran by reaction with magnesium.

Example 18

2-(5-Bromo-butyloxy)-tetrahydro-pyran magnesium

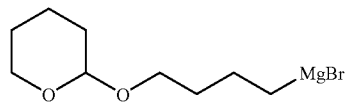

The title compound, a grignard reagent, was prepared from 2-(5-Bromo-butyloxy)-tetrahydro-pyran by reaction with magnesium.

Example 19

1-Biphenyl-4-yl-6-(tetrahydro-pyran-2-yloxy)-pentan-1-one

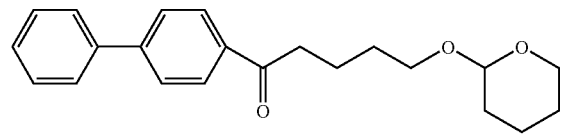

The title compound was prepared by reaction of the Grignard reagent 2-(5-bromo-butyloxy)-tetrahydro-pyran magnesium with the Weinreb amide biphenyl carboxylic acid methoxy-methyl amide.

Example 20

1-Biphenyl-4-yl-6-(tetrahydro-pyran-2-yloxy)-hexan-1-one

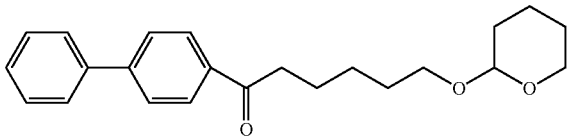

The title compound was prepared by reaction of the Grignard reagent 2-(5-bromo-pentyloxy)-tetrahydro-pyran magnesium with the Weinreb amide biphenyl-4-carboxylic acid methoxy-methyl amide.

Example 21

1-Biphenyl-4-yl-5-hydroxy-pentan-1-one (ABD-241)

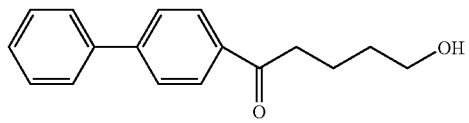

The tetrahydropyran group was removed from 1-biphenyl-4-yl-6-(tetrahydro-pyran-2-yloxy)-pentan-1-one to give the title compound, for example, using AcOH/THF/$H_2O$ (4:2:1) at 45° C. for 3.5 hours. Evaporation with xylene gives the desired free alcohol.

Example 22

1-Biphenyl-4-yl-6-hydroxy-hexan-1-one (ABD-68)

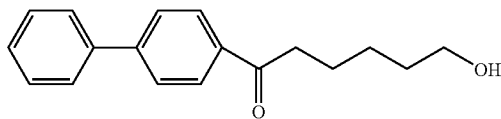

The tetrahydropyran group was removed from 1-biphenyl-4-yl-6-(tetrahydro-pyran-2-yloxy)-hexan-1-one to give the title compound, for example, using AcOH/THF/$H_2O$ (4:2:1) at 45° C. for 3.5 hours. Evaporation with xylene gives the desired free alcohol.

Example 23

1-Biphenyl-4-yl-hex-5-en-1-one (ABD-149)

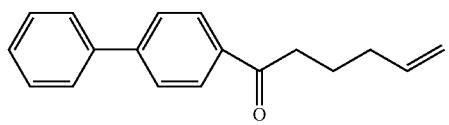

5-Bromo-1-pentene (1.5 g) was gently heated with magnesium turnings (1 g) in anhydrous tetrahydrofuran (15 ml) until reaction started. The mixture was left to reflux without further heating to give the Grignard reagent, then allowed to cool to room temperature. Biphenyl-4-carboxylic acid methoxy-methyl amide (4 g) was dissolved in anhydrous tetrahydrofuran (20 ml) and chilled in an ice bath. The Grignard reagent was added dropwise with vigorous stirring. Following addition, the mixture was allowed to warm to room temperature and stirring continued for 2 hours. Saturated $NH_4Cl$ solution (50 ml) was added and the mixture extracted with petrol. Drying with $Na_2SO_4$ followed by evaporation gave an oil. Column chromatography (petrol:ethyl acetate 5:1) gave the title compound as a white solid (70%). $\delta_C$ (CDCl$_3$, 62.9 MHz): 23.4, 33.3, 37.8, 115.4, 127.3, 127.3, 128.2, 128.7, 129.0, 135.8, 138.1, 139.9, 145.6 and 199.9. $\delta_H$ (CDCl$_3$, 250 MHz): 1.88 (2H, quintet, J 7.32), 2.17 (2H, quintet, J 7.32), 3.00 (2H, t, J 7.32), 5.03 (2H, m), 5.84 (1H, m), 7.62 (2H, d, J 7.9), 7.47 (3H, m), 7.67 (2H, d, J 7.9) and 8.03 (2H, d, J 7.9).

Example 24

1-Biphenyl-4-yl-hexan-1,6-diol (ABD-150)

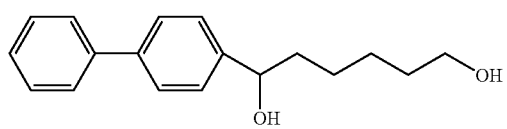

1-Biphenyl-4-yl-hex-5-en-1-one (1 g) was dissolved in 0.5 M $NaBH_4$ in diglyme (9 ml) and chilled in an ice bath. $BF_3.OEt_2$ (1 ml) in diglyme (4 ml) was added with vigorous stirring. Stirring was continued for 1 hour and water (1 ml) was added. 3M NaOH (2 ml) was added followed by 30% $H_2O_2$ (3 ml). Anhydrous $K_2CO_3$ (5 g) was added and the solvent decanted. The $K_2CO_3$ was washed with ethyl acetate and the combined organics dried ($Na_2SO_4$) and evaporated. Distillation under vacuum (oil bath temperature 175° C.) removed most of the remaining diglyme. The residue was purified by column chromatography (light petroleum:diethyl ether 2:1) to give a clear oil which solidified to give the title compound as a white powder (65%). $\delta_C$ (CDCl$_3$, 62.9 MHz): 25.6, 25.7, 32.6, 39.0, 62.8, 74.2, 126.4, 127.1, 127.2, 127.3, 128.8, 140.4, 140.8 and 143.9. $\delta_H$ (CDCl$_3$, 250 MHz): 1.39 (4H, m), 1.54 (2H, m), 1.81 (2H, m), 2.11 (1 or 2H, s), 3.37 (0 or 1H, s), 3.60 (2H, m), 4.69 (1H, t, J 6.4), 7.40 (5H, m) and 7.56 (4H, m). GCMS (EI$^+$) (Found M, 270. $C_{18}H_2O_2$ requires 270).

Example 25

1-Biphenyl-4-yl-hex-5-en-1-ol (ABD-162)

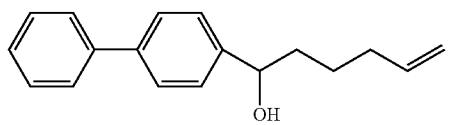

1-Biphenyl-4-yl-hex-5-en-1-one (1 g) was dissolved in diethyl ether (25 ml) $NaBH_4$ (2.5 g) was added and the mixture stirred for 30 minutes. Water (50 ml) was added and most of the solvent evaporated under vacuo. The residue was poured into water and the product extracted with ethyl acetate. The orgahic layer was dried ($Na_2SO_4$) and the ethyl acetate evaporated under vacuum to give a white solid. $\delta_C$ (CDCl$_3$, 62.9 MHz): 25.2, 33.6, 38.5, 74.3, 114.8, 126.4, 127.1, 127.2, 128.8, 138.6, 140.5, 140.9 and 143.9.

Example 26

4-(1-pentyloxyhex-5-enyl)-biphenyl (ABD-170)

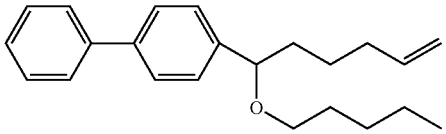

1-Biphenyl-4-yl-hex-5-en-1-ol (0.5 g) was dissolved in 30 ml tetrahydrofuran. NaH (0.2 g) was added and stirred for 15 min. Toluene-4-sulfonic acid pentyl ester (0.5 g) (prepared from tosyl chloride and pentanol in pyridine) was added and the mixture refluxed for 2 h then stirred overnight. The mixture was poured into water and extracted with DCM. The organic was dried (Na$_2$SO$_4$), and evaporated. The pure product was isolated as an oil by column chromatography (ethyl acetate/petrol). δ$_C$ (CDCl$_3$, 62.9 MHz): 14.1, 22.6, 25.3, 28.4, 29.7, 33.7, 38.0, 69.0, 81.9, 114.6, 127.1, 127.2, 128.8, 138.8, 140.2, 141.0 and 142.4. δ$_H$ (CDCl$_3$, 250 MHz): 0.89 (3H, m), 1.26 (6H, m), 1.57 (4H, m), 2.09 (2H, m), 3.30 (2H, m), 4.22 (1H, t), 4.96 (2H, m, alkenyl), 5.78 (1H, m, alkenyl), 7.35 (2H, d, J 8.24), 7.35 (1H, m), 7.43 (2H, t, J 7.93) and 7.57 (4H, d, J 8.24).

Example 27

6-Biphenyl-4-yl-6-pentyloxy-hexan-1-ol (ABD-177)

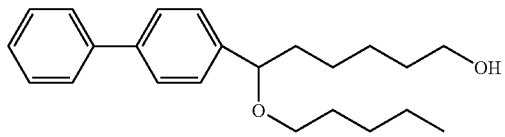

4-(1-pentyloxyhex-5-enyl)-biphenyl (1 g) was dissolved in 0.5 M NaBH$_4$ in diglyme (8 ml) and chilled in an ice bath. BF$_3$.OEt$_2$ (1 ml) in diglyme (4 ml) was added with vigorous stirring. Stirring was continued for 1 hour and water (1 ml) was added. 3M NaOH (2 ml) was added followed by 30% H$_2$O$_2$ (3 ml). Anhydrous K$_2$CO$_3$ (5 g) was added and the solvent decanted. The K$_2$CO$_3$ was washed with ethyl acetate and the combined organics dried (Na$_2$SO$_4$) and evaporated. Distillation under vacuum removes most of the remaining diglyme. The residue was purified by column chromatography (ethyl acetate/petrol) to give an oil. δ$_C$ (CDCl$_3$, 62.9 MHz): 14.1, 22.6, 25.7, 25.8, 28.4, 29.7, 32.7, 34.4, 63.0, 69.0, 82.0, 126.9, 127.1, 127.2, 128.8, 140.2, 141.0 and 142.4. δ$_H$ (CDCl$_3$, 250 MHz): 0.88 (3H, m), 1.16-1.55 (14H, m), 3.30 (2H, m), 3.62 (2H, t, J 6.1), 4.21 (1H, t, J 6.1), 7.34 (3H, d, J 7.6), 7.43 (2H, t, J 7.3) and 7.58 (4H, t, J 7.3).

Example 28

2'F-Biphenyl-4-carboxylic acid methoxy-methyl amide (ABD-153)

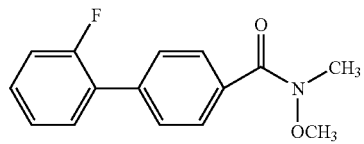

2'F-biphenyl-4-carbonyl chloride was prepared by the methods described in examples 6 to 9. This was reacted with N,O-dimethyl hydroxylamine hydrochloride using the procedure outlined in example 10 to give the title compound. δ$_C$ (CDCl$_3$, 62.9 MHz): 33.8, 61.2, 116.2 (d, J 22.5), 124.5 (d, J 2.9), 128.2 (d, J 13.7), 128.4, 128.7 (d, J 2.0), 129.6 (d, J 7.8), 130.7 (d, J 2.9), 133.2, 138.1, 159.7 (d, J 248.5) and 169.6.

Example 29

1-(2'-Fluoro-biphenyl-4-yl)-hex-5-en-1-one (ABD-173)

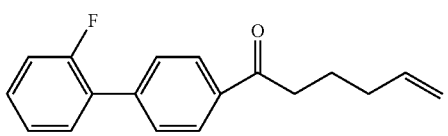

2'F-Biphenyl-4-carboxylic acid methoxy-methyl amide and the grignard reagent prepared from 5-bromopentene, were reacted as described in example 23 to give the title compound as a white solid. δ$_C$ (CDCl$_3$, 62.9 MHz): 23.4, 33.2, 37.8, 115.4, 116.3 (d, J 22.5), 124.6 (d, J 2.5), 128.1, 128.2, 129.2, 129.9 (d, J 8.8), 130.6 (d, J 2.9), 136.0, 138.1, 140.4, 159.8 (d, J 249.0) and 199.9.

Example 30

1-(2'-Fluoro-biphenyl-4-yl)-hexane-1,6-diol (ABD-182)

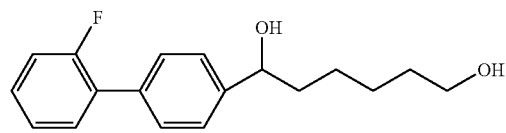

1-(2'-Fluoro-biphenyl-4-yl)-hex-5-en-1-one was converted into an alcohol using the method described in example 24 to give the title compound as white solid. δ$_C$ (DMSO, 62.9 MHz): 25.3, 25.5, 32.6, 60.7, 72.0, 116.1 (d, J 22.5), 124.6 (d, J 2.5), 126.1, 128.1 (d, J 13.7), 128.4, 129.3 (d, J 8.8), 130.7 (d, J 2.9), 133.3, 146.2 and 159.1 (d, J 246)

Example 31

4'-Br-Biphenyl-4-carboxylic acid methoxy-methyl amide (ABD-171)

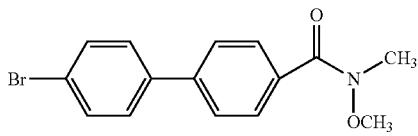

4'Br-biphenyl-4-carbonyl chloride was prepared as described above for 4'F-biphenyl-4-carbonyl chloride. This was reacted with N,O-dimethyl hydroxylamine hydrochloride using the procedure outlined in example 10 to give the title compound. $\delta_C$ (CDCl$_3$, 62.9 MHz): 33.9, 61.2, 122.2, 126.5, 128.8, 129.0, 132.0, 133.2, 139.2, 142.1 and 169.5.

Example 32

1-(4'-Bromo-biphenyl-4-yl)-hex-5-en-1-one (ABD-193)

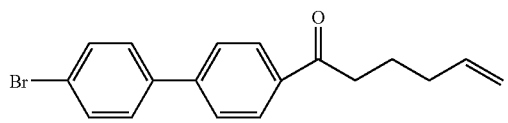

4'-Br-Biphenyl-4-carboxylic acid methoxy-methyl amide was reacted with a grignard prepared from 5-bromopentene and magnesium, as described for example 23, to give the title compound as a white solid. $\delta_C$ (CDCl$_3$, 62.9 MHz): 23.3, 33.2, 37.8, 115.4, 122.6, 127.1, 128.8, 128.8, 132.1, 136.0, 138.1, 138.8, 144.3 and 199.8.

Example 33

1-(4'-Bromobiphenyl)-4-yl-hexan-1,6-diol (ABD-195)

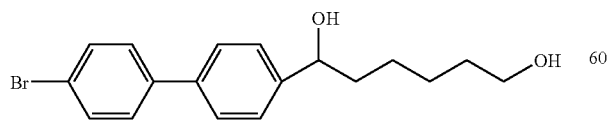

1-(4'-Bromo-biphenyl-4-yl)-hex-5-en-1-one was converted into an alcohol using the method described in example 24 to give the title compound as white solid. $\delta_C$ (CDCl$_3$, 62.9 MHz): 25.6, 25.7, 32.6, 39.1, 62.8, 74.2, 121.6, 126.5, 127.0, 128.7, 131.9, 139.2, 139.7 and 144.4.

Example 34

Acetic acid 6-acetoxy-6-biphenyl-4-yl-hexyl ester (ABD-191)

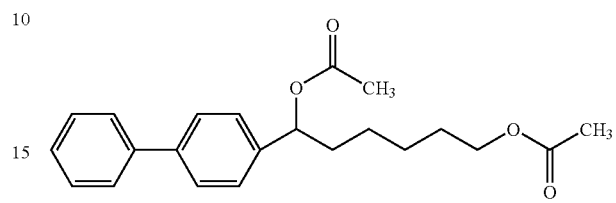

1-Biphenyl-4-yl-hexan-1,6-diol (1 g) was dissolved in acetic anhydride (25 ml). Pyridine (5 ml) was added and the mixture stirred for 3 hrs at 50° C. The mixture was poured into water (200 ml), extracted with dichloromethane (100 ml), dried (Na$_2$SO$_4$) and evaporated to give the title compound as a thick oil. $\delta_C$ (CDCl$_3$, 62.9 MHz): 21.0, 21.4, 25.2, 25.7, 28.5, 36.2, 64.4, 75.8, 127.0, 127.2, 127.3, 127.5, 128.8, 139.7, 140.8, 140.9 and 170.5.

Example 35

2-Biphenyl-4-yl-2-pent-4-enyl-[1,3]dithiane (ABD-151)

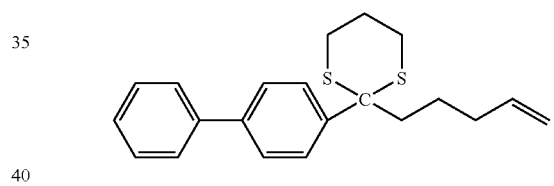

1-Biphenylyl-hex-5-en-1-one (1.5 g) was dissolved in DCM (30 ml). Propanedithiol (1.5 g) and boron trifluoride dietherate (1 ml) were added and the mixture stirred for 24 h. 5% NaOH (50 ml) was added and the mixture separated. The organic phase was washed with water, dried and evaporated to give an oil. Column chromatography (petrol/ethyl acetate) gave the title compound as a thick oil. $\delta_C$ (CDCl$_3$, 62.9 MHz): 23.2, 25.3, 27.7, 33.6, 44.6, 58.9, 115.0, 127.1, 127.1, 127.4, 128.8, 129.4, 138.1, 139.6, 140.5 and 141.0. $\delta_H$ (CDCl$_3$, 250 MHz): 1.40 (2H, m), 2.00 (6H, m), 2.70 (4H, m), 4.92 (2H, m), 5.68 (1H, m), 7.34 (1H, m), 7.44 (2H, m), 7.62 (4H, m) and 7.96 (2H, d, J 8.2).

Example 36

2-(4'-Bromobiphenyl-4-yl)-2-pent-4-enyl-[1,3]dithiane (ABD-214)

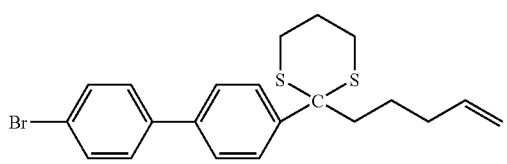

1-(4'-Bromo-biphenyl-4-yl)-hex-5-en-1-one (1.5 g) was dissolved in DCM (30 ml). Propanedithiol (1.5 g) and boron trifluoride dietherate (1 ml) were added and the mixture stirred for 24 h. 5% NaOH (50 ml) was added and the mixture separated. The organic phase was washed with water, dried and evaporated to give an oil. Column chromatography (petrol/ethyl acetate) gave the title compound as a thick oil. $\delta_C$ (CDCl$_3$, 62.9 MHz): 23.1, 25.3, 27.7, 33.6, 44.6, 58.8, 115.0, 121.7, 126.9, 128.6, 129.5, 131.9, 138.1, 138.3, 139.4 and 141.5.

Example 37

5-[2-(4'-Bromo-biphenyl-4-yl)-[1,3]dithian-2-yl]-pentan-1-ol (ABD-224)

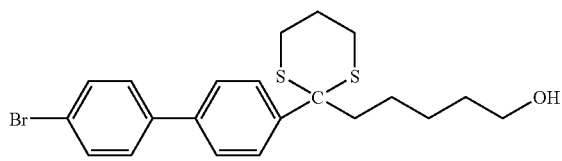

2-(4'-Bromobiphenyl-4-yl)-2-pent-4-enyl-[1,3]dithiane was converted into the title compound by the method described in Example 24. $\delta_C$ (CDCl$_3$, 62.9 MHz): 23.7, 25.3, 25.7, 27.7, 32.4, 45.2, 58.9, 62.8, 121.7, 126.9, 128.6, 129.5, 131.9, 138.3, 139.4 and 141.6

Example 38

1-(4'-Bromo-biphenyl-4-yl)-6-hydroxy-hexan-1-one (ABD-226)

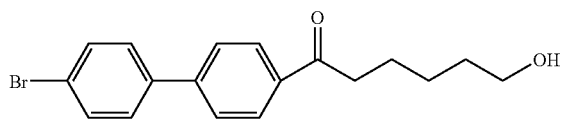

5-[2-(4'-Bromo-biphenyl-4-yl)-[1,3]dithian-2-yl]-pentan-1-ol was converted into the title compound by the method described in Example 5.

Example 39

2-Carboxyfluorene (ABD-197)

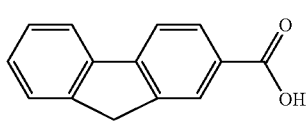

2-Acetylfluorene was oxidised as described in example 8 to give the title compound as a yellow solid.

Example 40

9H-Fluorene-2-carboxylic acid methoxy-methyl-amide (ABD-211)

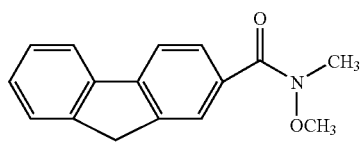

2-Carboxyfluorene (3 g) was refluxed in thionyl chloride (30 ml) for 4 h. Toluene was added and the solvent removed under reduced pressure to give the acid chloride as an amorphous solid. The title compound was prepared from the acid chloride using the method described in Example 10. $\delta_C$ (CDCl$_3$, 62.9 MHz): 33.6, 33.8, 61.2, 120.1, 120.9, 124.3, 124.6, 129.8, 133.7, 134.8, 134.9, 135.3, 143.6, 146.3 and 168.6.

Example 41

1-(9H-Fluoren-2-yl)-hex-5-en-1-ol (ABD-213)

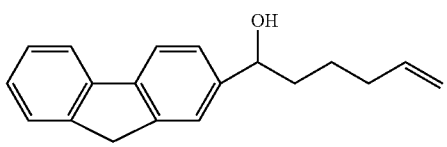

2-Fluorenecarboxaldehyde (3 g) was dissolved in a mixture of anhydrous diethyl ether (30 ml) and anhydrous diglyme (5 ml) and was reacted with a grignard prepared from 5-bromopentene and magnesium, as described for example 23. The mixture was stirred for 30 min and a precipitate filtered off and washed with diethyl ether to give a white powder. The powder was dissolved in DCM and washed with saturated NH$_4$Cl and water. Evaporation gave an oil which rapidly solidified. Column chromatography gave the title compound as a white solid. $\delta_C$ (CDCl$_3$, 62.9 MHz): 25.2, 33.7, 36.9, 38.7, 74.8, 114.8, 119.8, 119.9, 122.6, 124.7, 125.1, 126.7, 126.8, 138.7, 141.2, 141.5, 143.4, 143.6 and 143.6.

Example 42

1-(9H-Fluoren-2-yl)-hexane-1,6-diol (ABD-220)

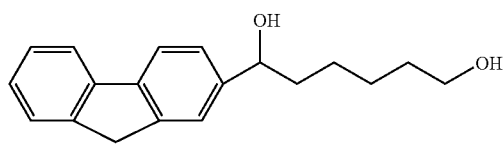

1-(9H-Fluoren-2-yl)-hex-5-en-1-ol was converted into the title compound by the method described in Example 24.

Evaporation of the solvent gave an off-white solid. Repeated trituration and precipitation with DCM gave the title compound as a white powder. $\delta_C$ (CDCl$_3$, 62.9 MHz): 25.7, 32.6, 36.9, 39.2, 62.8, 74.8, 119.8, 119.9, 122.6, 124.7, 125.1, 126.7, 126.8, 141.2, 141.5, 143.4 and 143.6.

Example 43

2-Carboxyphenanthrene (ABD-196)

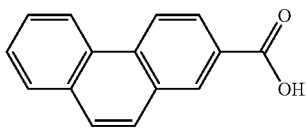

2-Acetylphenanthrene was oxidised as described in example 8 to give the title compound as a pale yellow solid.

Example 44

Phenanthrene-2-carboxylic acid methoxy-methyl-amide (ABD-210)

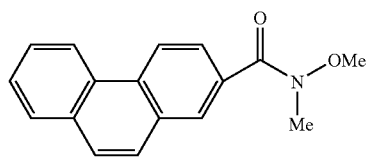

2-Carboxyphenanthrene (3 g) was refluxed in thionyl chloride (30 ml) for 4 h. Toluene was added and the solvent removed under reduced pressure to give the acid chloride as an amorphous solid. The title compound was then prepared from the acid chloride using the method described in Example 10.

Example 45

1-Phenanthren-2-yl-hex-5-en-1-one (ABD-212)

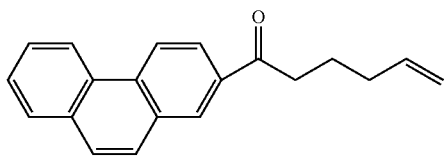

Phenanthrene-2-carboxylic acid methoxy-methyl-amide (1 g) was dissolved in anhydrous THF (30 ml). A grignard prepared from 5-bromopentene (3 g) and magnesium in anhydrous THF (15 ml), as described in example 23, was added and the mixture stirred for 2 h. Saturated NH$_4$Cl was added and the mixture extracted with petrol. The organic phase was dried and evaporated and purified by column chromatography (petrol/ethyl acetate) to give the title compound as a white powder. $\delta_C$ (CDCl$_3$, 62.9 MHz): 23.4, 33.3, 37.9, 115.4, 123.2, 123.3, 125.1, 127.0, 127.4, 127.8, 127.9, 128.8, 129.4, 129.7, 131.5, 133.0, 133.3, 134.8, 138.2 and 200.1

Example 46

1-Phenanthren-2-yl-hexane-1,6-diol (ABD-217)

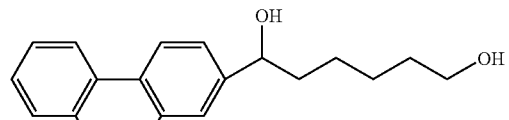

1-Phenanthren-2-yl-hex-5-en-1-one was converted into the title compound using the method described in Example 24.

Example 47

2-Biphenyl-4-yl-hept-6-en-2-ol (ABD-233)

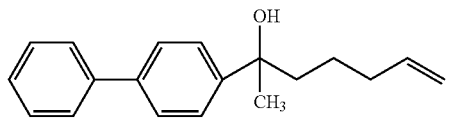

4-Acetylbiphenyl (2 g) was dissolved in anhydrous THF (30 ml) and reacted with a grignard prepared from 5-bromopentene and magnesium in THF (15 ml) as described in example 23 to give the title compound as a yellow powder.

Example 48

6-Biphenyl-4-yl-heptane-1,6-diol (ABD-237)

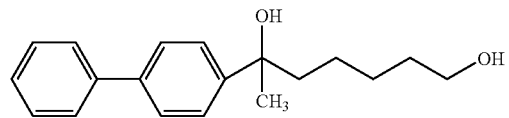

2-Biphenyl-4-yl-hept-6-en-2-ol was converted into the title compound using the method described in Example 24.

Example 49

2-(4'-Bromobiphenyl-4-yl)-hept-6-en-2-ol (ABD-238)

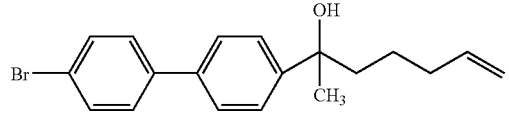

4-(4-Bromophenyl)-acetophenone (2 g) was dissolved in anhydrous THF (30 ml) and reacted with a grignard prepared from 5-bromopentene and magnesium in THF (15 ml) as described in example 23 to give the title compound as a yellow powder.

Example 50

6-(4'-Bromo-biphenyl-4-yl-heptane-1,6-diol (ABD-239)

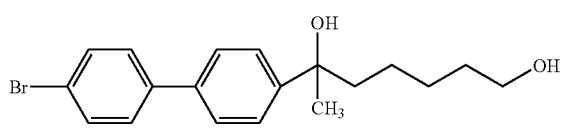

2-Biphenyl-4-yl-hept-4-en-2-ol was converted into the title compound using the method described in Example 24.

Example 51

1-Biphenyl-4-yl-6-hydroxy-hexan-1-one-O-methyl-oxime (ABD-151)

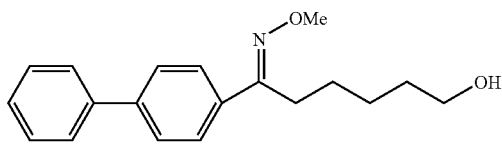

6-Hydroxy-1-(4-biphenyl) hexan-1-one (120 mg) and O-Methyl hydroxylamine hydrochloride (200 mg, 25% solution in water) were dissolved in methanol (10 ml) containing pyridine (100 mg). The mixture was stirred at room temperature for 30 min, poured into dichloromethane and washed with water. Evaporation and column chromatography (ethyl acetate/light petroleum) gave the desired product as an amorphous solid (85%). $\delta_C$ (CDCl$_3$, 62.9 MHz): 25.9, 26.4, 26.5, 32.5, 62.0, 126.7, 127.1, 127.2, 127.6, 128.9, 134.6, 140.5, 141.8 and 158.3. $\delta_H$ (CDCl$_3$, 250 MHz): 1.45-1.65 (7H, m), 2.78 (2H, t, J 7.0), 3.63 (2H, t, J 6.4), 4.0 (3H, s), 7.36 (1H, d, J 7.0), 7.45 (2H, t, J 7.0), 7.60 (4H, m) and 7.71 (2H, d, J 8.2). GCMS (EI$^+$) (Found M, 297. C$_{19}$H$_{23}$NO$_2$ requires 297).

Biological Studies

Initial screening of candidate compounds was performed using viability assays, on cultures of the macrophage cell line J774, which have been used before as a model system for osteoclast survival (see, e.g., Luckman et al., 1998). The assay is based on the survival of the J774 macrophage cell line; macrophages are closely related to osteoclasts, and contain similar high levels of esterase activity.

MTT Macrophage J774 Viability Assay

J774 cells were plated at $10^4$ cells per well in 150 μL αMEM (alpha Modified Eagle Medium) in 96-well plates and grown overnight. The next day, compounds were added to the cultures, and culture was continued for another 72 hours. At the end of the culture period cell survival was determined using the tetrazolium dye-based MTT assay as previously described (see, e.g., MacPherson et al., 1999).

MTT (3-(4,5-dimethylthiazol-2-yl)-2,5-diphenyl tetrazolium bromide) has an orange colour and is soluble in the medium used for cell culture. The mitochondrial enzyme succinate dehydrogenase acts upon MTT in living cells to produce the insoluble purple coloured formazan. The amount of formazan produced, as measured by UV/visible spectroscopy, is proportional to the number of viable cells.

Briefly, MTT (5 mg/ml MTT in αMEM) was added to each well (1:10 v/v, 15 μL) and the cells incubated for 4 hours. The medium was carefully removed using a needle without dislodging the crystal layer. 100 μL acidified isopropanol (4 M HCl 1:100 v/v in isopropanol) was added to each well and the purple crystals allowed to dissolve. The absorbance was measured in a plate reader at 540 nm, with 690 nm as reference. The controls were a deep purple colour, indicating a high number of live cells. The results for each test compound were expressed as a percent (%) of the average control value.

Addition of Compounds. All of the compounds studied were made up as 100 mM solutions in DMSO. These stock solutions were then diluted 100× in culture medium. From these 1 mM solutions, convenient quantities (3-15 μL) were added directly to the wells so as to give the desired final compound concentration.

Alamar Blue Macrophage J774 Viability Assay

J774 cells were plated at $10^4$ cells per well in 150 μL αMEM (α Modified Eagle Medium) in 96-well plates and grown overnight. The next day, compounds were added to the cultures, and culture was continued for another 72 hours. At the end of the culture period cell survival was determined using an Alamar Blue assay as previously described (see, e.g., Nociari et al., 1998).

Alamar Blue is an oxidation-reduction sensitive indicator. The dye itself is in the oxidised state, which is blue and non-fluorescent. The dye can accept electrons from reducing species, such as NADPH and FADH, to form a reduced dye species, which is red and fluorescent. Thus the transformation from oxidised form to reduced form can be measured by fluorimetric or colourimetric means. For fluorescence measurements, 530-560 nm excitation and 590 nm emission wavelengths are typically used. For colourimetric measurements, absorbance is measured at 570 nm (reduced form) and 600 nm (oxidised form) and a simple calculation performed to determine the relative quantities of the two species.

A high ratio of the reducing species, NADPH and FADH, to the corresponding oxidised species, NADP and FAD, is an indicator that cells are proliferating and viable. A low ratio indicates cells that are quiescent or non-viable.

Briefly, Alamar Blue (Biosource International) was added undiluted to the each well (1:10 v/v, 15 μL). The plate was incubated at 37° C. for 34 hours and the fluorescence was measured at 570 nm, with a 25 nm bandwidth. A high reading indicated cells with normal viability, and a low reading indicates cells that have been damaged and are no longer proliferating normally. The controls gave a high fluorescence reading, indicating a high number of live, healthy cells. A potent test compound gave a low fluorescence reading. The average results for each test compound (n=5) were expressed as a percent (%) of the average control value.

Addition of Compounds. All of the compounds studied were made up as 100 mM solutions in DMSO. These stock solutions were then diluted 100 or 1000× in culture medium (αMEM). From these 1 mM or 100 μM solutions, convenient quantities (3-15 μL) were added directly to the wells so as to give the desired final compound concentration.

This assay offers numerous advantages over other assays, including MTT assays: it permits a higher throughput; it is more sensitive; it is non-damaging to the cells; it is faster; it generally gives an identical result to MTT assay.

Alamar Blue Mouse Osteoblast Assay

Osteoblasts were isolated as described above and plated at $10^4$ cells/well in 96-well plates in 100 μL of αMEM supplemented with 10% FCS and antibiotics. Test compounds were added after 24 hours and left for 72 hours. Cell viability was assessed using the Alamar Blue assay as described for J774 macrophages. Alamar Blue (Biosource International) was added undiluted to each well (1:10 v/v, 10 μL). The plate was incubated at 37° C. for 3 to 4 hours and the fluorescence was measured at 570 nm, with a 25 nm bandwidth.

Additional Studies

Some compounds were further evaluated in two model systems of true osteoclasts: (a) the murine co-culture system, and (b) the rabbit osteoclast culture system.

Murine Co-Culture System

The first model system, the murine co-culture system, studies the formation of osteoclasts from precursors present in the bone marrow. The number of osteoclasts and the amount of dentine resorption was measured.

Osteoclast formation and activity was studied using an adaptation (see, e.g., van't H of & Ralston, 1997) of the osteoblast-bone marrow co-culture assay originally described by Takahashi et al., 1988.

Co-Culture Methods. Co-culture (see, e.g., Van't H of et al., 1997) is a method to study the formation of osteoclasts from their precursors. In this assay, osteoblasts were obtained from the calvaria of 2-3 day old neonatal mice. These were plated on dentine, stimulated with 1,25-dihydroxy vitamin $D_3$ to stimulate RANKL and M-CSF expression. Early osteoclast precursors were present in the bone marrow of adult mice. The bone marrow suspension was purified to remove the red blood cells and the remainder cultured on top of the osteoblast layer. The stimulatory factors then allowed the osteoclast precursors to differentiate into mature osteoclasts. At the end of the culture osteoclasts were identified by TRAcP staining and the resorption activity was measured in the same manner as for rabbit osteoclasts.

Although it is possible to generate osteoclasts from bone marrow cells alone by treating the cultures with RANKL and M-CSF, the co-culture system is still regarded as one of the most reliable and reproducible available. It is useful for studying the effects of drugs on both osteoclast progenitors and mature osteoclasts.

Preparation of Dentine. the Dentine was Elephant Ivory, Preferred to Bone Because of its uniform surface, which facilitates easy visualisation of resorption pits. It was cut into slices of approximately 200 μm thickness using a Buehler Isomet low speed saw with a diamond wafering blade (series 15 HC). These slices were polished by hand, to a high degree, until one side was shiny. Out of these slices, discs were punched that fit the wells of a 96 well plate, using a paper puncher. Excess residues from the polish were removed by sonication. The discs were then stored in 70% ethanol until required. These discs were then dried and placed shiny side up in the wells of a 96 well plate. Cells were seeded onto the dentine. Following completion of the culture, these dentine slices were carefully removed from the plate and studied under the microscope.

Osteoblast Isolation. Briefly, osteoblasts were isolated from the calvarial bones of 2-day-old mice by sequential collagenase digestion (type I collagenase, Sigma) and cultured in αMEM supplemented with 10% FCS (foetal calf serum) and penicillin and streptomycin at 37° C. in 5% $CO_2$.

More specifically, osteoblasts were obtained from a collagenase digestion of the calvaria (skull bones) of 2-3 day old neo-natal MF1 mice. At this stage in their development these are soft and easily removed. The calvaria from 5-6 mice were carefully dissected and washed in HBSS (Hank's balanced saline solution). The calvaria were placed in a 15 mL tube and shaken at 37° C. in 4 mL collagenase (10 mg/ml) for 10 minutes. This removes the excess unwanted tissue. The liquid was disposed of and a further 4 mL collagenase (10 mg/ml) added to the tube. The calvaria were then digested for a further 30 minutes. After this the supernatant (F1) was removed and retained. The calvaria were washed with a 2×4 mL PBS and this was added to F1. 4 mL EDTA (ethylene diamine tetraacetic acid) (4 mM in PBS) was then added to complex the calcium and allow further extraction of osteoblasts. This was shaken for 10 minutes at 37° C. The supernatant was removed and retained (F2). The calvaria were again washed with 2×4 mL HBSS and this was added to F2. The final 4 mL of collagenase (10 mg/ml) was added to the tube and this was again shaken at 37° C. for 30 minutes. Whilst this was being done, F1 and F2 were spun down at 300 g for 3 minutes, brake 3. The pellets were re-suspended in 1 mL medium (αMEM supplemented with 10% FCS (foetal calf serum) and penicillin and streptomycin), combined and added to 10 mL medium in two 75 $cm^2$ flasks. The liquid from the final collagenase digestion was collected (F3), the calvaria washed and the combined liquid extracts spun down in the centrifuge. The pellet was re-suspended in 1 mL medium and added in equal proportions to the flasks containing F1 and F2. The flasks were left for 4-6 hours at 37° C. and then the medium was changed to remove any non-adherent cells. These flasks may be left for up to 4 days at 37° C., 5% $CO_2$.

Osteoblast Plating. The medium was removed from the flasks and the cells washed with PBS. 2 mL Trypsin was added to the cells and these were incubated at 37° C. for 2 minutes. The flasks usually required gentle agitation to fully loosen the cells. 4 mL medium supplemented with 10% FCS was added to stop the enzymatic action. The cells were removed and the flask washed out with medium. The cell suspension was spun down at 300 g for 3 minutes, the medium removed and the pellet re-suspended in 1 mL medium. The cells were counted and then seeded in a 96 well plated containing dentine slices, at $8 \times 10^3$ cells per well in 100 μl medium containing 1000× dilution of stock 1,25-dihydroxyvitamin $D_3$ (final conc. 10 nM/well) to stimulate the expression of RANKL and cultured overnight.

Isolation of Bone Marrow Cells. Briefly, bone marrow cell populations containing osteoclast precursors were isolated from the long bones of 3-5 month old mice and erythrocytes were removed by Ficoll Hypaque density gradient centrifugation. The resulting bone marrow cells were washed with PBS (phosphate buffered saline) and re-suspended in culture medium.

More specifically, the femurs and tibia were dissected from 2-3 adult MF1 mice (3-6 months old) and the surrounding tissue was removed. The bones were trimmed to allow access to the bone marrow. The marrow was flushed out using a 25 G needle and HBSS+10% FCS. A single cell suspension is obtained by repeatedly squeezing the cell suspension through needles of decreasing size (start with 19 G, end with 25 G). 5 mL Ficoll was added to a 15 mL tube and the cell suspension carefully placed on top of this with the minimum amount of mixing between the layers. The density centrifugation was performed at 600 g, 25 minutes, brake off. This was sufficient to allow the red blood cells to congregate at the bottom of the tube, fats to remain at the top of the liquid and the desired bone marrow cells to collect at the interface. The cloudy layer from the interface was collected with a pipette, placed in a fresh 15 mL tube and made up to 12 mL with HBSS. The cell suspension was spun down at 300 g for 3 minutes. The pellet was collected and re-suspended in 1 mL medium. The bone marrow cells were counted and then added to the 96 well plate containing the osteoblasts at $2 \times 10^5$ cells/well in 50 μL medium.

Osteoclast Precursor Studies. To investigate the effects of a drug on osteoclast precursors the timetable was as follows:

Day 0—Plate osteoblasts.

Day 1—Plate bone marrow cells

Day 2—Add test compound.

Day 4—100% medium refresh+1,25-dihydroxyvitamin $D_3$ (final conc. 10 nm/well)

Day 6—Add IL1 (10 u/ml) and 1,25-dihydroxyvitamin $D_3$ (final conc. 10 nm/well)

Day 10—Fix cells.

Mature Osteoclast Studies. To investigate the effects of a drug on mature osteoclasts the timetable was as follows:

Day 0—Plate osteoblasts.

Day 1—Plate bone marrow cells.

Day 6—50% medium refresh+10 nM IL1 and 1,25-dihydroxyvitamin $D_3$.

Day 7—Add drugs and remove and fix day 7 control slices.

Day 10—Fix cells.

At the conclusion of a study, the cells were fixed in 4% formaldehyde for 10 minutes and washed in PBS. Fixed cells were either stained and kept in 70% ethanol or refrigerated in water or PBS. The 50% medium refresh involved the addition of 150 μL fresh medium containing a 500× dilution of 1,25-dihydroxyvitamin $D_3$ and a 250× dilution of IL1 (interleukin 1). This was left for 15 minutes and then 150 μL medium carefully removed. The medium refresh must be done very carefully, because the confluent layer of osteoblasts can be quite easily disturbed, and detached. This would result in a total absence of osteoclasts. Usually the first osteoclasts and resorption pits appeared on day 6. Reasonable numbers of osteoclasts were present between day 7-10.

At the end of the culture, the osteoclasts were identified by staining for tartrate-resistant acid phosphatase (TRAcP) staining and resorption pit area was quantified by reflected light microscopy as described previously (see, e.g., van't H of & Ralston, 1997).

TRAcP Staining. Osteoclasts express very high levels of the enzyme tartrate resistant acid phosphatase (TRAcP) and can therefore be easily visualised by staining for this enzyme, for example, by the following method. Two staining solutions, (1) and (2), were made up freshly as follows:

Solution 1. 300 μL Naphthol-AS-BI-phosphate stock.

1.5 mL Veronal buffer.

1.8 mL Acetate buffer.

1.8 mL Acetate buffer with 100 mM tartrate.

Solution 2. 240 μL Pararosaniline.

240 μL $NaNO_2$ (4% stock solution).

Naphthol-AS-BI-phosphate stock: 10 mg/ml Naphthol-AS-BI-phosphate in dimethylformamide.

Veronal buffer 1.17 g anhydrous Sodium Acetate; 2.94 g Veronal (sodium barbiturate); dissolved in 100 mL distilled water.

Acetate buffer 0.1 M, pH 5.2: solution (a): 0.82 g Sodium Acetate anhydrous dissolved in 100 mL distilled water; solution (b): 0.6 mL Acetic acid glacial made up to 100 mL with distilled water; pH of solution (a) adjusted to pH 5.2 with solution (b).

Pararosaniline: 1 g Pararosaniline in 20 mL distilled water. 5 mL concentrated hydrochloric acid was added, the solution was heated carefully in a water bath while stirring. The solution was allowed to cool and then filtered.

Solutions (1) and (2) were mixed and filtered to give the staining solution. The PBS from the wells was removed and at least 50 μL of staining solution added. The cells were incubated at 37° C. for about 45 minutes, or until the dentine slices appeared sufficiently red. To determine what passes as sufficient it was necessary to remove the dentine slice and check under a light microscope that the osteoclasts were suitably stained. The staining solution was then removed and replaced with 70% ethanol. The dentine slices were stored in a refrigerator.

Osteoclast Counting. This was done using a light-microscope to determine the number of TRAcP positive multinucleated cells on each dentine slice. The slices were carefully removed from the 96-well plate, avoiding disturbance of the cell layer, and placed on a glass slide. A few drops of 70% ethanol were put on each slice followed by a glass coverslip. Working across the dentine the number of multinucleated, red-stained cells were counted. There were usually a large number of small red mononucleated cells. These were osteoclast precursors and these were not counted. The numbers of osteoclasts on the control slices can range from 300 up to 1000. For each compound or concentration studied, the average of the values for the 5 slices was taken and expressed as a percent (%) of the average value for the controls. Any obvious outlying values were ignored. The most common reason for this was when there were no cells of any kind, usually indicating that the osteoblast layer has detached during handling.

Quantification of Resorption Area. After the osteoclasts were stained and counted it was necessary for the dentine slice to be thoroughly cleaned. The slices were rubbed on a suitable surface, a piece of blue roll proved ideal for this purpose. In order to clean the slices properly it may be necessary to wash them in dilute HClO for a few seconds to loosen the cell debris. The resorption pits can be visualised either by staining with dyes such as Toluidine blue or Coomassie blue, by scanning electron microscopy or by reflected light microscopy. Here, reflected light microscopy was used, because it is easy to perform, the slices needed only thorough cleaning and no staining, and the image obtained could be fairly easily quantified using image analysis. Because the slices need to be completely flat for the reflected light microscopy, they were glued glass slides under pressure of a 0.5 kg metal weight. These may then be easily stored. A Zeiss reflected light microscope was used, fitted with a 2.5× lens, wide field c-mount adapter, and Diagnostics Instruments Insight B/W large chip digital camera. This set-up allowed the capture of an entire bone slice in one image at sufficient resolution to identify and measure the resorption pits. The image analysis software package was developed using the Aphelion ActiveX image analysis toolkit from ADCIS (ADCIS SA, Hérouville-Saint-Clair, France). The dentine slices appeared as a bright shiny surface littered with dark resorption pits. The software calculated the resorption areas for each slice. When determining the effects of the compounds in co-cultures, it was necessary to use both the values obtained for slices removed at the time when the drugs were added (e.g., Day 7), as well as the controls from the end of the study (e.g., Day 10).

Rabbit Osteoclast Culture System

The second model system was the rabbit osteoclast system, where mature, functional osteoclasts were isolated from the long bones of rabbits and cultured on dentine slices.

Osteoclast Isolation. Osteoclasts were isolated from the long bones of 2-10 day-old rabbits, as described previously (see, e.g., reference Coxon et al., 2000). All 4 limbs were removed from the rabbits and placed in ice-cold PBS. Soft tissue and cartilage were removed and the bones transferred into fresh PBS. The bones were minced in αMEM (without FCS), using a scalpel. All the medium and fragments were transferred to a 50 mL tube, vortexed for 3×10 seconds and left to stand for 1 minute. The supernatant was removed and made up to 50 mL/rabbit with medium and FCS so as to give a final concentration of 10% FCS.

Osteoclast Plating. The cells were plated onto dentine slices in a 96 well plate, at 100 μL/well (medium: αMEM supplemented with 10% FCS and penicillin and streptomycin) and left for 4 hours to allow adherence to the dentine. After this period the medium was removed, and with it the non-adherent cells. Fresh medium was then added. The remaining population was highly enriched in osteoclasts.

Culturing. At this point, test compounds to be studied were added and the cells cultured at 37° C. in 5% $CO_2$ for 48 hours. At the end of the culture, the osteoclasts were identified by staining for tartrate-resistant acid phosphatase (TRAcP) staining. A good number of osteoclasts in the controls was 100-200. The results were expressed as a percent (%) of the average number of osteoclasts seen in the controls. The resorption pit area was quantified by reflected light microscopy as described previously (see, e.g., van't H of & Ralston, 1997) and again the results expressed as a percent (%) of the control values.

In Vivo Studies

Animals. Female 9 week-old C57/BL6 mice. Animals were housed in a designated animal facility and routinely maintained on a 12 h:12 h light:dark cycle and given ad libitum access to food and water.

Ovariectomy induced bone loss. Bilateral ovariectomy (Ovx) was performed under general anaesthesia. Sham ovariectomy (Sham) was similarly performed but with externalisation and replacement of the ovaries. Animals were given a gavage of (a) candidate compound (e.g., 20 mg/kg) in vehicle (olive oil), or (b) vehicle (olive oil). After 21 days, the animals were killed, and the tibial bones were dissected and used for bone mineral density measurements.

Bone Mineral Measurements. Measurements of bone mineral density (BMD) at the left proximal tibial metaphysis were determined by peripheral quantitative computed tomography (pQCT) using an XCT Research M bone densitometer with a voxel size of 70 μm and analysis software version 5.1.4. (Stratec Medizintechnik, Pforzheim, Germany). Daily quality assurance measurements were performed using a plexi-coated PVC-fluorinated hydrocarbon phantom according to the manufacturer's instructions.

Biological Data

Examples of the claimed compounds were synthesized and tested for their biological activity using methods as described above.

BRIEF DESCRIPTION OF THE DRAWINGS

FIG. 1 is a graph of macrophage viability, as measured by the MTT (■) and Alamar Blue (Δ) macrophage J774 viability assays, expressed as percent (%) of control, after 72 hours exposure to 6-hydroxy-1-(4-biphenyl) hexan-1-one (ABD-68) as a function of compound concentration.

Figure 2:
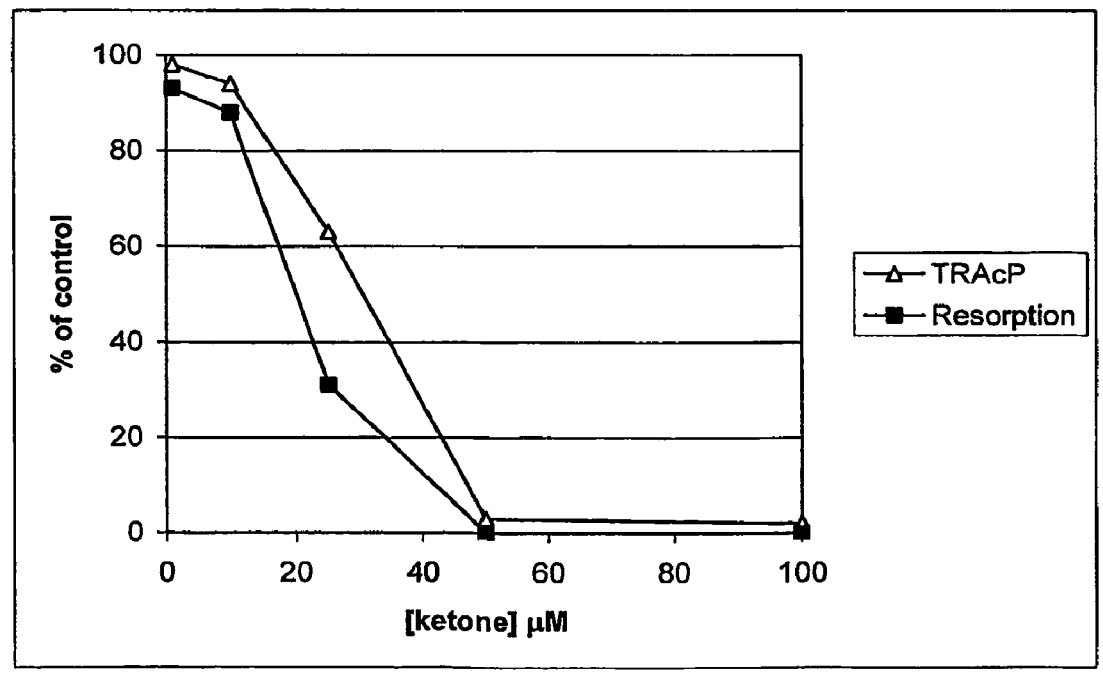
FIG. 2 is a graph showing the effects in the murine co-culture system, and is a plot of (a) the number of murine osteoclasts measured by TRAcP (Δ) and (b) resorption pit area (■), as a function of compound concentration, both expressed as a percent (%) of control value, after 72 hours exposure to of 6-hydroxy-1-(4-biphenyl)hexan-1-one (ABD-68).

FIG. 2 is a graph showing the effects in the murine co-culture system, and is a plot of (a) the number of murine osteoclasts measured by TRAcP (Δ) and (b) resorption pit area (■), as a function of compound concentration, both expressed as a percent (%) of control value, after 72 hours exposure to of 6-hydroxy-1-(4-biphenyl) hexan-1-one (ABD-68).

Figure 3:
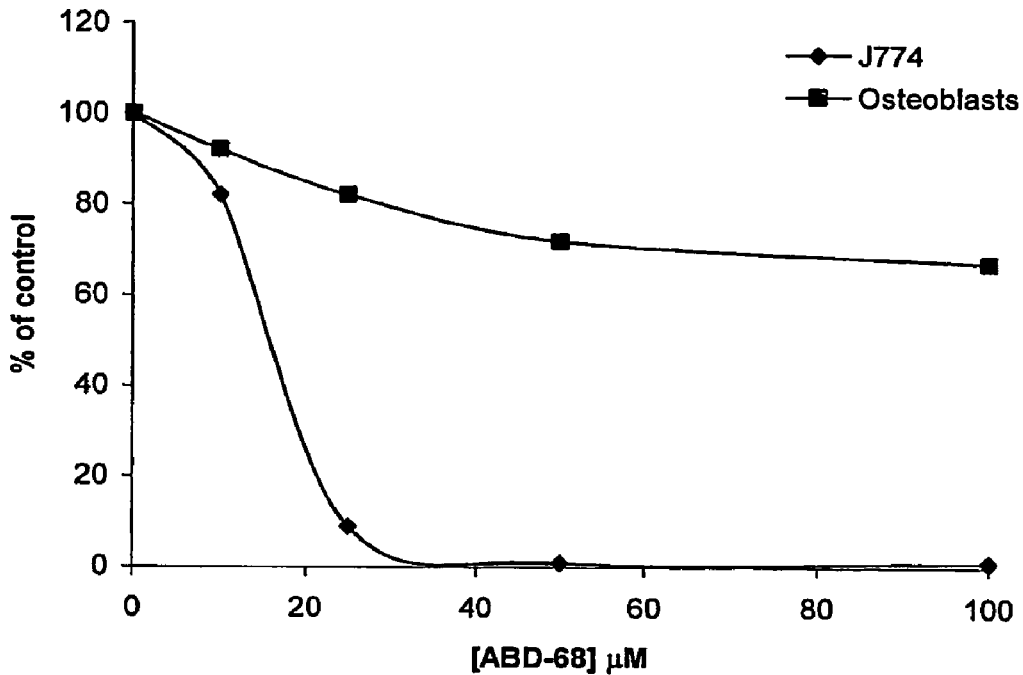
FIG. 3 is a graph of J774 macrophage viability (♦) as measured by the Alamar Blue macrophage J774 viability assay; and osteoblast survival (■) as measured by the Alamar Blue mouse osteoblast assay; expressed as percent (%) of control, after 72 hours exposure to 6-hydroxy-1-(4-biphenyl) hexan-1-one (ABD-68) as a function of compound concentration.

FIG. 3 is a graph of J774 macrophage viability (♦) as measured by the Alamar Blue macrophage J774 viability assay; and osteoblast survival (■) as measured by the Alamar Blue mouse osteoblast assay; expressed as percent (%) of control, after 72 hours exposure to 6-hydroxy-1-(4-biphenyl) hexan-1-one (ABD-68) as a function of compound concentration.

FIG. 3 shows that ABD-68 is highly potent against J774 macrophages ($IC_{60}$<20 μM) but shows little activity against osteoblasts ($IC_{50}$>100 μM). This demonstrates the ABD-68 has the potential to be an effective drug for the treatment diseases involving excess bone loss, such as osteoporosis.

Figure 4:
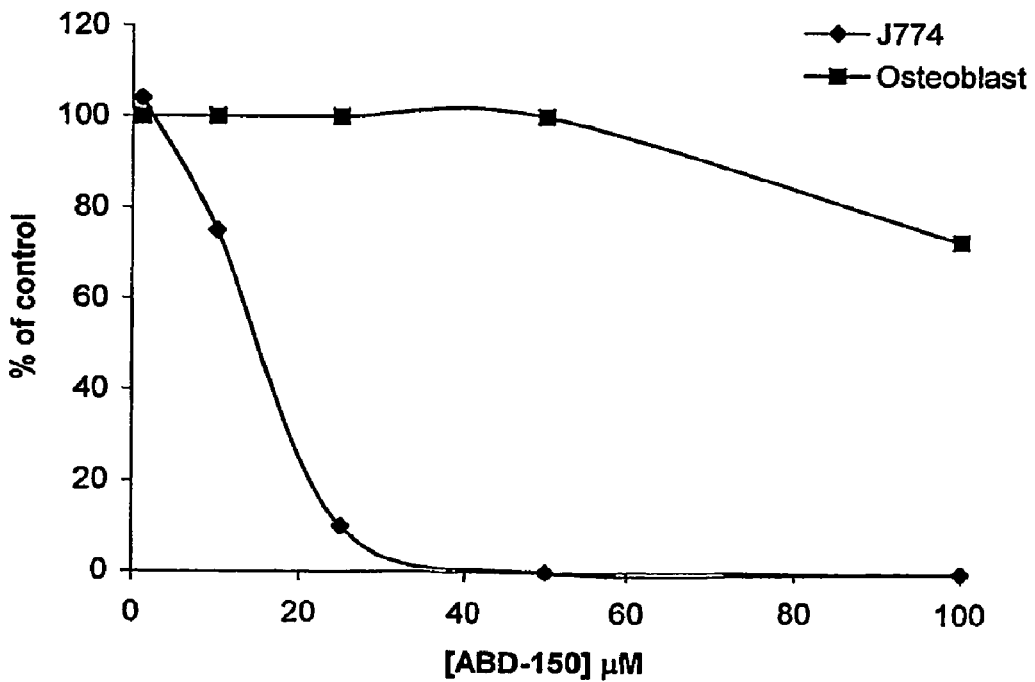
FIG. 4 is a graph of J774 macrophage viability (♦) as measured by the Alamar Blue macrophage J774 viability assay; and osteoblast survival (■) as measured by the Alamar Blue mouse osteoblast assay; expressed as percent (%) of control, after 72 hours exposure to 1-biphenylyl-hexan-1,6-diol (ABD-150) as a function of compound concentration.

FIG. 4 is a graph of J774 macrophage viability (♦) as measured by the Alamar Blue macrophage J774 viability assay; and osteoblast survival (■) as measured by the Alamar Blue mouse osteoblast assay; expressed as percent (%) of control, after 72 hours exposure to 1-biphenyl-4-yl-hexan-1, 6-diol (ABD-150) as a function of compound concentration.

FIG. 4 shows that the reduced form (ABD-150) of the ketone was found to be at least as active as the parent ketone (ABD-68) against J774 macrophages ($IC_{50}$<20 μM) and to have a similar lack of activity against osteoblasts ($IC_{50}$>100 μM).

Figure 5:
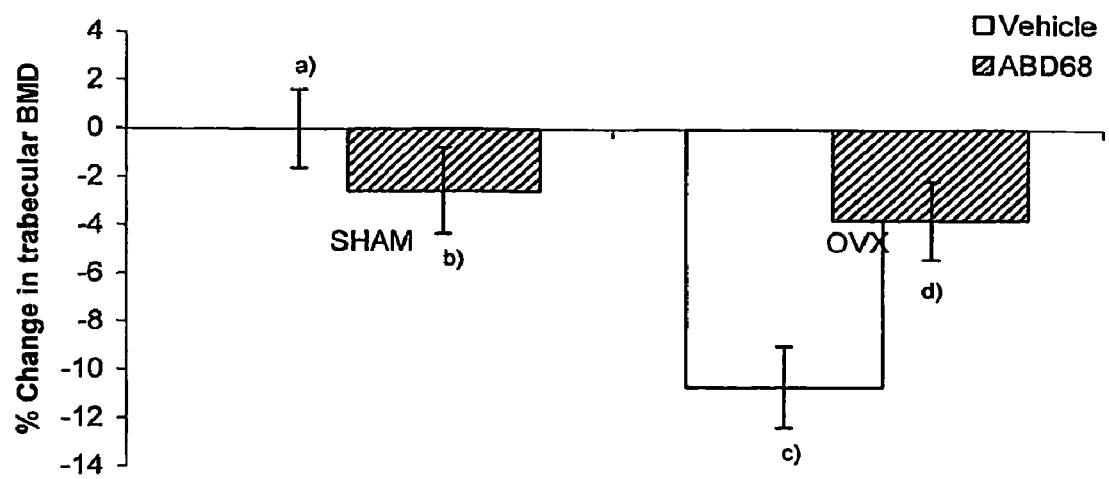
FIG. 5 is a bar graph showing percent changes in trabecular bone mineral density (BMD), for: (a) Sham operation, no drug; (b) Sham operation, 6-hydroxy-1-(4-biphenyl) hexan- 1-one (ABD-68) (20 mg/kg); (c) OVX operation, no drug; and (d) OVX operation, 6-hydroxy-1-(4-biphenyl)hexan-1-one (ABD-68) (20 mg/kg).

FIG. 5 is a bar graph showing percent changes in trabecular bone mineral density (BMD), for: (a) Sham operation, no drug; (b) Sham operation, 6-hydroxy-1-(4-biphenyl) hexan-1-one (ABD-68) (20 mg/kg); (c) OVX operation, no drug; and (d) OVX operation, 6-hydroxy-1-(4-biphenyl) hexan-1-one (ABD-68) (20 mg/kg).

FIG. 5 demonstrates the ability of ABD-68 to reverse the effects of ovariectomy-induced bone loss, and shows that ABD-68 is very effective at reversing the bone loss seen in this model for post-menopausal osteoporosis.

The foregoing has described the principles, preferred embodiments, and modes of operation of the present invention. However, the invention should not be construed as limited to the particular embodiments discussed. Instead, the above-described embodiments should be regarded as illustrative rather than restrictive, and it should be appreciated that variations may be made in those embodiments by workers skilled in the art without departing from the scope of the present invention.

REFERENCES

A number of patents and publications are cited above in order to more fully describe and disclose the invention and the state of the art to which the invention pertains. Full citations for these references are provided below. Each of these references is incorporated herein by reference in its entirety into the present disclosure, to the same extent as if each individual reference was specifically and individually indicated to be incorporated by reference.

Armour, K. J., et al., 2001, "Inhibition of bone resorption in vitro and prevention of ovariectomy-induced bone loss in vivo by flurbiprofen nitroxybutylester (HCT1026)," *Arthritis Rheum.*, Vol. 44, No. 9, pp. 2185-2192.

Barta, T. E., et al., 2002, "Aromatic Sulfone Hydroxamates and Their Use as Protease Inhibitors," published international (PCT) patent application publication no. WO 02/092588, (PCT/US02/15257) published 21 Nov. 2002.

Boots, M. R., et al., 1973, "Hypocholesterolemic Agents II: Inhibition of β-Hydroxy-β-Methylglutaryl Coenzyme A Reductase by Arylalkyl Hydrogen Succinates and Glutarates," *J. Pharm. Sci.*, Vol. 62, No. 6, pp. 952-957.

Boots, M. R., et al., 1976, "Hypocholesterolemic Agents IV: Inhibition of β-Hydroxy-β-Methylglutaryl Coenzyme A Reductase by Arylalkenyl and Arylepoxy Hydrogen Succinates and Glutarates," *J. Pharm. Sci.*, Vol. 65, No. 5, pp. 724-727.

Coxon, F. P., Helfrich, M. H., Van't H of, R., Sebti, S., Ralston, S. H., Hamilton, A., and Rogers, M. J., 2000, "Protein geranylgeranylation is required for osteoclast formation, function, and survival: inhibition by bisphosphonates and GGTI-298," *J. Bone Miner. Res.*, Vol. 15, pp. 1467-1476.

Degenhardt and Burdsall, 1986, "Synthesis of Ethenylidenebis(phosphonic acid) and its Tetraalkyl Esters," *J. Org. Chem.*, Vol. 51, pp. 3488-3490.

Eberhard and Westheimer, 1965, "Hydrolysis of Phostonates," *J. Amer. Chem. Soc.*, Vol. 87, pp. 252-260.

Herczegh et al, 2002, "Osteoadsorptive Bisphosphonate Derivatives of Fluoroquinolone Antibacterials," *J. Med. Chem.*, Vol. 45, pp. 2338-2341.

Hickey et al., 1997, "Azetidinone Derivatives for the Treatment of Atherosclerosis," published international (PCT) patent application publication number WO 97/41099, published 6 Nov. 1997.

Hughes, D. E., Boyce, B. F., 1997, "Apoptosis in bone physiology and disease," *Molecular Pathology*, Vol. 50, pp. 132-137.

Inukai et al., 1977, "p-Cyanophenyl 4-alkyl-4'-biphenylcarboxylate, method for preparing same and liquid crystal compositions using same," U.S. Pat. No. 4,017,416 granted 12 Apr. 1977.

Kong, Y. Y., Yoshida, H., Sarosi, I., Tan, H. L., Timms, E., Capparelli, C., et al, 1999, "OPGL is a key regulator of osteoclastogenesis, lymphocyte development and lymph-node organogenesis," *Nature*, Vol. 397, pp. 315-323.

Konno, M. M., et al., 2002, (ONO Pharmaceutical Co. Ltd.), "Hydroxamic Acid Derivatives, Process for the Production Thereof, and Drugs Containing the Same as the Active Ingredient," published European patent application number EP 1215203, published 19 Jun. 2002.

Luckman, S. P., Coxon, F. P., Ebetino, F. H., Russell, R. G., and Rogers, M. J., 1998, "Heterocycle-containing bisphosphonates cause apoptosis and inhibit bone resorption by preventing protein prenylation: evidence from structure-activity relationships in J774 macrophages," *J. Bone Miner. Res.*, Vol. 13, pp. 1668-1678.

MacPherson, H; Noble, B. S.; Ralston, S. H., 1999, "Expression and functional role of nitric oxide synthase isoforms in human osteoblast-like cells," *Bone* Vol. 24, pp. 179-185.

Mai, A., et al., 1997, "Arylketotetramethylene Analogues of Disoxaril with Anti-Human Rhinovirus 14 Activity," *Antiviral Chemistry & Chemotherapy*, Vol. 8, No. 3, pp. 235-242.

Mundy, G. R., 1996, *Bone Remodelling and its disorders* (2nd edition), London: Martin Dunitz.

Naka et al., 2002, (ONO Pharmaceuticals Co. Ltd.), "IL-6 Production Inhibitors," published international (PCT) patent application publication no. WO 02/074298, published 26 Sep. 2002.

Nociari, M. N., et al., 1998, "A Novel one-step, highly sensitive fluorimetric assay to evaluate cell-mediated cytotoxicity," *Journal of Immunological Methods*, Vol. 213, pp. 157-167.

Raisz, L. G., 1988, "Local and systemic factors in the pathogenesis of osteoporosis," *N. Engl. J. Med.*, Vol. 318, pp. 818-828.

Ralston, S. H., 1997, "Science, Medicine and the Future: Osteoporosis," *Br. Med. J.*, Vol. 315, pp. 469-472.

Ralston, S. H., et al., 2003, "Alkane Diol Derivatives as Therapeutic Agents for the Treatment of Bone Conditions," published international (PCT) patent application publication no. WO 03/037321, (PCT/GB02/04933) published 8 May 2003.

Rodan, G. A., Harada, S., 1997, "The missing bone," *Cell*, Vol. 89, pp. 677-680.

Shibata et al., 1999, (Japan Tobacco Inc), "Amides, Bone Formation Promoters Containing Them, and Their Use as Antiosteoporotic Agents," Japanese patent publication number 11-80107 published 26 Mar. 1999.

Takahashi, N.; Akatsu, T.; Udagawa, N.; Sasaki, T.; Yamaguchi, A.; Moseley, J. M.; Martin, T. J.; Suda, T., 1988, "Osteoblastic cells are involved in osteoclast formation," *Endocrinology*, Vol. 123, pp. 2600-2602, 1988.

Tew et al., 1997, "Clavulanic Acid Derivatives for Treating Atherosclerosis," published international (PCT) patent application publication number WO 97/10247, published 20 Mar. 1997.

van't H of, R. J., and Ralston, S. H., 1997, "Cytokine-induced nitric oxide inhibits bone resorption by inducing apoptosis of osteoclast progenitors and suppressing osteoclast activity," *J. Bone Miner. Res.*, Vol. 12, pp. 1797-804.

Yasuda, H., Shima, N., Nakagawa, N., Mochizuki, S. I., Yano, K., Fujise, N., et al, 1998, "Identity of osteoclastogenesis inhibitory factor (OCIF) and osteoprotegerin (OPG): a mechanism by which OPG/OCIF inhibits osteoclastogenesis in vitro," *Endocrinology*, Vol. 139, pp. 1329-1337.

Yuan, Y, F., et al., 2000, "Studies on Volatile Oil in Ligusticum Chuanxiong by Supercritical Fluid Extraction," *Zhongguo Yaoxue Zazhi (Beijing)* (Clin. Pharm. J. (Beijing)), Vol. 35, No. 2, pp. 84-87.

We claim:

1. A compound selected from compounds of the following formulae and pharmaceutically acceptable salts, amides, esters, and ethers thereof:

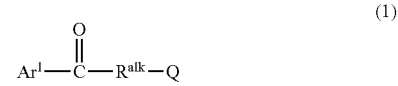

(1)

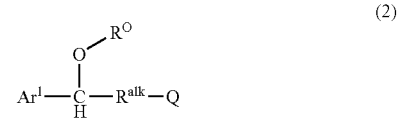

(2)

wherein:

Ar$^1$ is independently a group of the following formula:

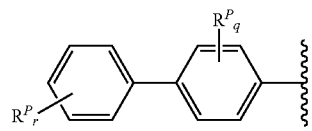

wherein:

q is independently an integer from 0 to 4;

r is independently an integer from 0 to 5; and each R$^P$ is independently selected from: (1) carboxylic acid; (2) ester; (3) amido; (4) acyl; (5) halo; (6) cyano; (7) nitro; (8) hydroxy; (9) ether; (10) thiol; (11) thioether; (12) acyloxy; (13) amino; (14) acylamino; (15)

aminoacylamino; (16) sulfonamino; (17) sulfonyl; (18) sulfonate; (19) sulfonamido; (20) $C_{5-20}$aryl-$C_{1-7}$alkyl; (21) $C_{5-20}$aryl; (22) $C_{3-20}$heterocyclyl; (23) $C_{1-7}$alkyl; (24) oxo; (25) imino; (26) hydroxyimino; and (27) phosphate;

$R^{alk}$ is independently a $C_{4-8}$alkylene group, and is unsubstituted, or substituted with one or more substituents selected from: halogen, hydroxy, $C_{1-7}$alkoxy, amino, and amido;

—$OR^O$, if present, is independently —OH or —$OR^K$;

—$OR^K$, if present, is independently selected from:
 —O—$R^{K1}$;
 —O—C(=O)$R^{K2}$;
 —O—C(=O)O$R^{K3}$;
 —O—S(=O)$_2$O$R^{K4}$;

wherein:
each of $R^{K1}$, $R^{K2}$, $R^{K3}$, and $R^{K4}$ is independently $C_{5-20}$aryl-$C_{1-7}$alkyl, $C_{5-20}$aryl, $C_{3-20}$heterocyclyl, or $C_{1-7}$alkyl, and is optionally substituted; and
each of $R^{K3}$ and $R^{K4}$ may additionally be —H;
Q is independently —OH or —$OR^{OT}$;
wherein:
—$OR^{OT}$, if present, is independently: —O—$R^{E1}$;
wherein:
$R^{E1}$ is independently: $C_{5-20}$aryl-$C_{1-7}$alkyl, unsubstituted or substituted with one or more groups selected from (1) carboxylic acid; (2) ester; (3) amido; (4) acyl; (5) halo; (6) cyano; (7) nitro; (8) hydroxy; (9) ether; (10) thiol; (11) thioether; (12) acyloxy; (13) amino; (14) acylamino; (15) aminoacylamino; (16) sulfonamino; (17) sulfonyl; (18) sulfonate; (19) sulfonamido; (20) $C_{5-20}$aryl-$C_{1-7}$alkyl; (21) $C_{5-20}$aryl; (22) $C_{3-20}$heterocyclyl; (23) $C_{1-7}$alkyl; (24) oxo; (25) imino; (26) hydroxyimino; and (27) phosphate;

$C_{5-20}$aryl, unsubstituted or substituted with one or more groups selected from (1) carboxylic acid; (2) ester; (3) amido; (4) acyl; (5) halo; (6) cyano; (7) nitro; (8) hydroxy; (9) ether; (10) thiol; (11) thioether; (12) acyloxy; (13) amino; (14) acylamino; (15) aminoacylamino; (16) sulfonamino; (17) sulfonyl; (18) sulfonate; (19) sulfonamido; (20) $C_{5-20}$aryl-$C_{1-7}$alkyl; (21) $C_{5-20}$aryl; (22) $C_{3-20}$heterocyclyl; (23) $C_{1-7}$alkyl; (24) oxo; (25) imino; (26) hydroxyimino; and (27) phosphate;

$C_{3-20}$heterocyclyl, unsubstituted or substituted with one or more groups selected from (1) carboxylic acid; (2) ester; (3) amido; (4) acyl; (5) halo; (6) cyano; (7) nitro; (8) hydroxy; (9) ether; (10) thiol; (11) thioether; (12) acyloxy; (13) amino; (14) acylamino; (15) aminoacylamino; (16) sulfonamino; (17) sulfonyl; (18) sulfonate; (19) sulfonamido; (20) $C_{5-20}$aryl-$C_{1-7}$alkyl; (21) $C_{5-20}$aryl; (22) $C_{3-20}$heterocyclyl; (23) $C_{1-7}$alkyl; (24) oxo; (25) imino; (26) hydroxyimino; and (27) phosphate; or $C_{1-7}$alkyl, unsubstituted or substituted with one or more groups selected from (1) carboxylic acid; (2) ester; (3) amido; (4) acyl; (5) halo; (6) cyano; (7) nitro; (8) hydroxy; (9) ether; (10) thiol; (11) thioether; (12) acyloxy; (13) amino; (14) acylamino; (15) aminoacylamino; (16) sulfonamino; (17) sulfonyl; (18) sulfonate; (19) sulfonamido; (20) $C_{5-20}$aryl-$C_{1-7}$alkyl; (21) $C_{5-20}$aryl; (22) $C_{3-20}$heterocyclyl; (24) oxo; (25) imino; (26) hydroxyimino; and (27) phosphate;

wherein the group —C(=O)— in formula (1) is optionally replaced with a group selected from the following groups, wherein each R is independently $C_{5-20}$aryl-$C_{1-7}$alkyl, $C_{5-20}$aryl, $C_{3-20}$heterocyclyl, or $C_{1-7}$alkyl, and is optionally substituted:

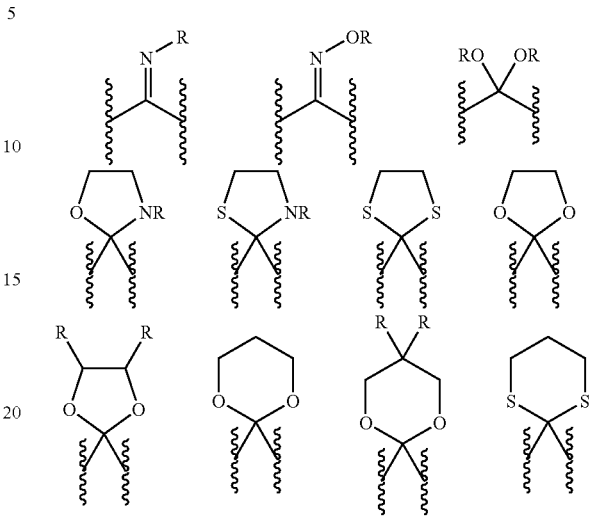

with the proviso that if —$OR^{OT}$ is —O—$R^{E1}$, then $R^{E1}$ is not a phenyl group substituted with a sulfonyl group; and
with the proviso that —$OR^O$, if present, is other than siloxy.

2. A compound according to claim 1, wherein the group —C(=O)— in formula (1) is not replaced as described in claim 1.

3. A compound according to claim 2, wherein the compound is selected from compounds of formula (1) and pharmaceutically acceptable salts, amides, esters, and ethers thereof.

4. A compound according to claim 2, wherein the compound is selected from compounds of formula (2) and pharmaceutically acceptable salts, amides, esters, and ethers thereof.

5. A compound according to claim 4, wherein:
each of $R^{K1}$, $R^{K2}$, $R^{K3}$, and $R^{K4}$, if present, is independently $C_{1-7}$alkyl, and is optionally substituted; and
each of $R^{K3}$ and $R^{K4}$, if present, may additionally be —H.

6. A compound according to claim 4, wherein —$OR^O$, if present, is independently —OH.

7. A compound according to claim 3, wherein $R^{alk}$ is a fully saturated $C_{4-8}$alkylene group and is unsubstituted.

8. A compound according to claim 4, wherein $R^{alk}$ is a fully saturated $C_{4-8}$alkylene group and is unsubstituted.

9. A compound according to claim 6, wherein $R^{alk}$ is a fully saturated $C_{4-8}$alkylene group and is unsubstituted.

10. A compound according to claim 3, wherein $R^{alk}$ is —(CH$_2$)$_n$— where n is an integer from 4 to 8.

11. A compound according to claim 4, wherein $R^{alk}$ is —(CH$_2$)$_n$— where n is an integer from 4 to 8.

12. A compound according to claim 6, wherein $R^{alk}$ is —(CH$_2$)$_n$— where n is an integer from 4 to 8.

13. A compound according to claim 3, wherein $R^{alk}$ is —(CH$_2$)$_5$— or —(CH$_2$)$_6$—.

14. A compound according to claim 4, wherein $R^{alk}$ is —(CH$_2$)$_5$— or —(CH$_2$)$_6$—.

15. A compound according to claim 6, wherein $R^{alk}$ is —(CH$_2$)$_5$— or —(CH$_2$)$_6$—.

16. A compound according to claim 3, wherein Q is independently —OH.

17. A compound according to claim 4, wherein Q is independently —OH.

18. A compound according to claim 6, wherein Q is independently —OH.

19. A compound according to claim 7, wherein Q is independently —OH.

20. A compound according to claim 8, wherein Q is independently —OH.

21. A compound according to claim 9, wherein Q is independently —OH.

22. A compound according to claim 10, wherein Q is independently —OH.

23. A compound according to claim 11, wherein Q is independently —OH.

24. A compound according to claim 12, wherein Q is independently —OH.

25. A compound according to claim 13, wherein Q is independently —OH.

26. A compound according to claim 14, wherein Q is independently —OH.

27. A compound according to claim 15, wherein Q is independently —OH.

28. A compound according to claim 25, wherein $Ar^1$ is independently a group of the following formula:

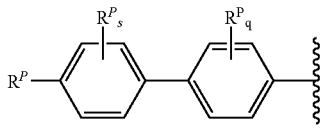

wherein:
q is an integer from 0 to 2; and
s is an integer from 0 to 2.

29. A compound according to claim 27, wherein $Ar^1$ is independently a group of the following formula:

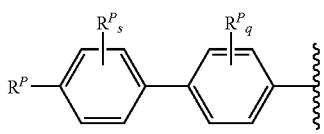

wherein:
q is an integer from 0 to 2; and
s is an integer from 0 to 2.

30. A compound according to claim 25, wherein $Ar^1$ is independently a group of the following formula:

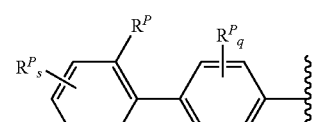

wherein:
q is an integer from 0 to 2; and
s is an integer from 0 to 2.

31. A compound according to claim 27, wherein $Ar^1$ is independently a group of the following formula:

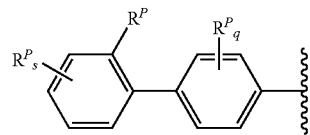

wherein:
q is an integer from 0 to 2; and
s is an integer from 0 to 2.

32. A compound according to claim 25, wherein $Ar^1$ is independently a group of the following formula:

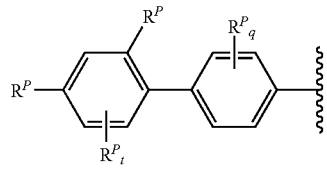

wherein:
q is an integer from 0 to 2; and
t is an integer from 0 to 1.

33. A compound according to claim 27, wherein $Ar^1$ is independently a group of the following formula:

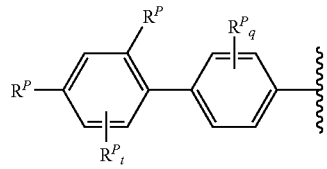

wherein:
q is an integer from 0 to 2; and
t is an integer from 0 to 1.

34. A compound according to claim 25, wherein $Ar^1$ is independently a group of the following formula:

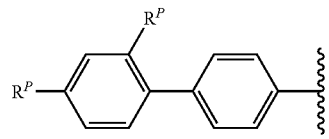

35. A compound according to claim 27, wherein $Ar^1$ is independently a group of the following formula:

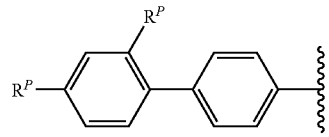

36. A compound according to claim 1, wherein each $R^P$ is independently selected from:

(1) —C(=O)OH;

(2) —C(=O)OMe, —C(=O)OEt, —C(=O)O(iPr), —C(=O)O(tBu); —C(=O)O(cPr); —C(=O)OCH$_2$CH$_2$OH, —C(=O)OCH$_2$CH$_2$OMe, —C(=O)OCH$_2$CH$_2$OEt; —C(=O)OPh, —C(=O)OCH$_2$Ph;

(3) —(C=O)NH$_2$, —(C=O)NMe$_2$, —(C=O)NEt$_2$, —(C=O)N(iPr)$_2$, —(C=O)N(CH$_2$CH$_2$OH)$_2$; —(C=O)-morpholino, —(C=O)NHPh, —(C=O)NHCH$_2$Ph;

(4) —(C=O)Me, —(C=O)Et, —(C=O)(tBu), —(C=O)-cHex, —(C=O)Ph; —(C=O)CH$_2$Ph;

(5) —F, —Cl, —Br, —I;

(6) —CN;

(7) —NO$_2$;

(8) —OH;

(9) —OMe, —OEt, —O(iPr), —O(tBu), —OPh, —OCH$_2$Ph; —OCF$_3$, —OCH$_2$CF$_3$; —OCH$_2$CH$_2$OH, —OCH$_2$CH$_2$OMe, —OCH$_2$CH$_2$OEt; —OCH$_2$CH$_2$NH$_2$, —OCH$_2$CH$_2$NMe$_2$, —OCH$_2$CH$_2$N(iPr)$_2$; —OPh-Me, —OPh-OH, —OPh-OMe, —OPh-F, —OPh-Cl, —OPh-Br, —OPh-I;

(10) —SH;

(11) —SMe, —SEt, —SPh, —SCH$_2$Ph;

(12) —OC(=O)Me, —OC(=O)Et, —OC(=O)(iPr), —OC(=O)(tBu); —OC(=O)(cPr); —OC(=O)CH$_2$CH$_2$OH, —OC(=O)CH$_2$CH$_2$OMe, —OC(=O)CH$_2$CH$_2$OEt; —OC(=O)Ph, —OC(=O)CH$_2$Ph;

(13) —NH$_2$, —NHMe, —NHEt, —NH(iPr), —NMe$_2$, —NEt$_2$, —N(iPr)$_2$, —N(CH$_2$CH$_2$OH)$_2$; —NHPh, —NHCH$_2$Ph; piperidino, piperazino, morpholino;

(14) —NH(C=O)Me, —NH(C=O)Et, —NH(C=O)Ph, —NHC(=O)CH$_2$Ph; —NMe(C=O)Me, —NMe(C=O)Et, —NMe(C=O)Ph, —NMeC(=O)CH$_2$Ph;

(15) —NH(C=O)NH$_2$, —NH(C=O)NHMe, —NH(C=O)NHEt, —NH(C=O)NPh, —NH(C=O)NHCH$_2$Ph; —NH(C=S)NH$_2$, —NH(C=S)NHMe, —NH(C=S)NHEt, —NH(C=S)NPh, —NH(C=S)NHCH$_2$Ph;

(16) —NHSO$_2$Me, —NHSO$_2$Et, —NHSO$_2$Ph, —NHSO$_2$PhMe, —NHSO$_2$CH$_2$Ph; —NMeSO$_2$Me, —NMeSO$_2$Et, —NMeSO$_2$Ph, —NMeSO$_2$PhMe, —NMeSO$_2$CH$_2$Ph;

(17) —SO$_2$Me, —SO$_2$CF$_3$, —SO$_2$Et, —SO$_2$Ph, —SO$_2$PhMe, —SO$_2$CH$_2$Ph;

(18) —OSO$_2$Me, —OSO$_2$CF$_3$, —OSO$_2$Et, —OSO$_2$Ph, —OSO$_2$PhMe, —OSO$_2$CH$_2$Ph;

(19) —SO$_2$NH$_2$, —SO$_2$NHMe, —SO$_2$NHEt, —SO$_2$NMe$_2$, —SO$_2$NEt$_2$, —SO$_2$-morpholino, —SO$_2$NHPh, —SO$_2$NHCH$_2$Ph;

(20) —CH$_2$Ph, —CH$_2$Ph-Me, —CH$_2$Ph-OH, —CH$_2$Ph-F, —CH$_2$Ph-Cl;

(21) -Ph, -Ph-Me, -Ph-OH, -Ph-OMe, -Ph-F, -Ph-Cl, -Ph-Br, -Ph-I; pyridyl, pyrazinyl, pyrimidinyl, pyridazinyl; furanyl, thiophenyl, pyrrolyl, imidazolyl, pyrazolyl, oxazolyl, thiazolyl;

(22) pyrrolidinyl, piperidinyl, azepinyl, tetrahydropyranyl, morpholinyl, azetidinyl, piperazinyl, imidazolinyl, piperazinedionyl, and oxazolinonyl;

(23) -Me, -Et, -nPr, -iPr, -nBu, -iBu, -sBu, -tBu, -nPe; -cPr, -cHex; —CH=CH$_2$, —CH$_2$—CH=CH$_2$; —CF$_3$, —CHF$_2$, —CH$_2$F, —CCl$_3$, —CBr$_3$, —CH$_2$CH$_2$F, —CH$_2$CHF$_2$, and —CH$_2$CF$_3$; —CH$_2$OH, —CH$_2$OMe, —CH$_2$OEt, —CH$_2$NH$_2$, —CH$_2$NMe$_2$; —CH$_2$CH$_2$OH, —CH$_2$CH$_2$OMe, —CH$_2$CH$_2$OEt, —CH$_2$CH$_2$CH$_2$NH$_2$, —CH$_2$CH$_2$NMe$_2$;

(24) =O;

(25) =NH, =NMe; =NEt;

(26) =NOH;

(27) —OP(=O)(OH)$_2$, —P(=O)(OH)$_2$, —OP(=O)(OMe)$_2$, —P(=O)(OMe)$_2$.

37. A compound according to claim 1, wherein each $R^P$ is independently selected from:

(1) —C(=O)OH;

(2) —C(=O)OMe, —C(=O)OEt, —C(=O)O(tBu), —C(=O)OPh;

(3) —C(=O)NH$_2$, —C(=O)NHMe, —C(=O)NMe$_2$, —C(=O)NHPh;

(4) —C(=O)Me;

(5) —F, —Cl, —Br, —I;

(6) —CN;

(7) —NO$_2$;

(8) —OH;

(9) —OMe, —OEt, —O(iPr), —O(nPr), —O(tBu), —OPh, —OBn;

(11) —SMe;

(12) —OC(C=O)Me, —OC(C=O)Et, —OC(C=O)(tBu), —OC(C=O)Ph;

(13) —NH$_2$, —NHMe, —NMe$_2$, —NHEt, —NEt$_2$;

(14) —NHC(=O)Me, —NHC(=O)Et, —NHC(=O)Ph;

(17) —S(=O)$_2$Me, —S(=O)$_2$Et, —S(=O)$_2$Ph.

19) —SO$_2$NH$_2$,

(21) -Ph;

(23) -Me, -Et, -iPr, -nPr, -cPr, -tBu, —CF$_3$;

(27) —P(=O)(OMe)$_2$.

38. A compound according to claim 25, wherein each $R^P$ is independently selected from: -Me, —F, —Cl, —Br, —I, —OH, —OMe, —NH$_2$, —NMe$_2$, —NO$_2$, and —CN.

39. A compound according to claim 27, wherein each $R^P$ is independently selected from: -Me, —F, —Cl, —Br, —I, —OH, —OMe, —NH$_2$, —NMe$_2$, —NO$_2$, and —CN.

40. A compound according to claim 28, wherein each $R^P$ is independently selected from: -Me, —F, —Cl, —Br, —I, —OH, —OMe, —NH$_2$, —NMe$_2$, —NO$_2$, and —CN.

41. A compound according to claim 29, wherein each $R^P$ is independently selected from: -Me, —F, —Cl, —Br, —I, —OH, —OMe, —NH$_2$, —NMe$_2$, —NO$_2$, and —CN.

42. A compound according to claim 30, wherein each $R^P$ is independently selected from: -Me, —F, —Cl, —Br, —I, —OH, —OMe, —NH$_2$, —NMe$_2$, —NO$_2$, and —CN.

43. A compound according to claim 31, wherein each $R^P$ is independently selected from: -Me, —F, —Cl, —Br, —I, —OH, —OMe, —NH$_2$, —NMe$_2$, —NO$_2$, and —CN.

44. A compound according to claim 32, wherein each $R^P$ is independently selected from: -Me, —F, —Cl, —Br, —I, —OH, —OMe, —NH$_2$, —NMe$_2$, —NO$_2$, and —CN.

45. A compound according to claim 33, wherein each $R^P$ is independently selected from: -Me, —F, —Cl, —Br, —I, —OH, —OMe, —NH$_2$, —NMe$_2$, —NO$_2$, and —CN.

46. A compound according to claim 34, wherein each $R^P$ is independently selected from: -Me, —F, —Cl, —Br, —I, —OH, —OMe, —NH$_2$, —NMe$_2$, —NO$_2$, and —CN.

47. A compound according to claim 35, wherein each $R^P$ is independently selected from: -Me, —F, —Cl, —Br, —I, —OH, —OMe, —NH$_2$, —NMe$_2$, —NO$_2$, and —CN.

48. A compound according to claim 34, wherein each $R^P$ is independently selected from: —F, —Cl, —Br, and —I.

49. A compound according to claim 35, wherein each $R^P$ is independently selected from: —F, —Cl, —Br, and —I.

50. A compound according to claim 1, wherein said compound is selected from the following compounds, and pharmaceutically acceptable salts, amides, esters, and ethers thereof:

(ABD-68)
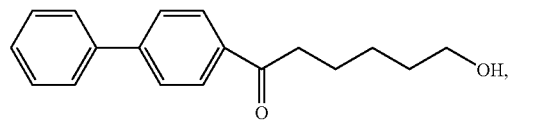

(ABD-81)
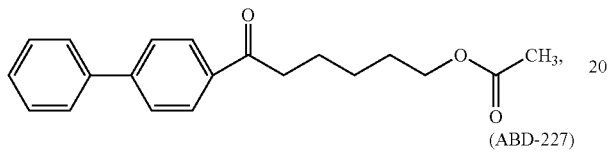

(ABD-227)
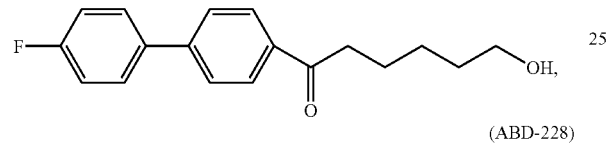

(ABD-228)
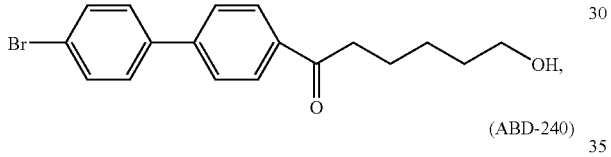

(ABD-240)
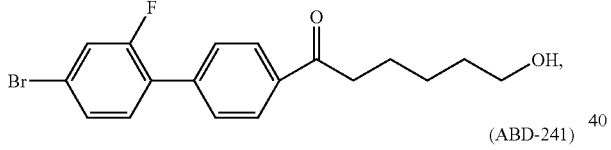

(ABD-241)
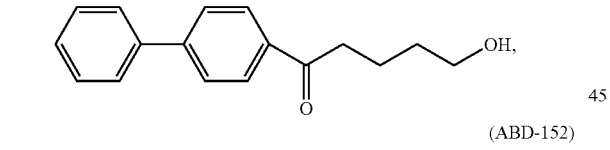

(ABD-152)
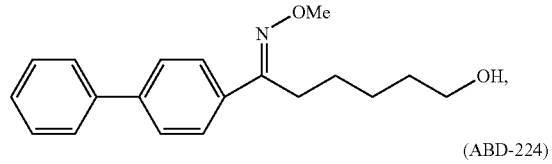

(ABD-224)
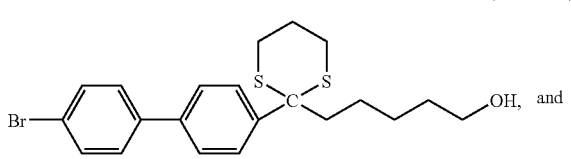

(ABD-229)
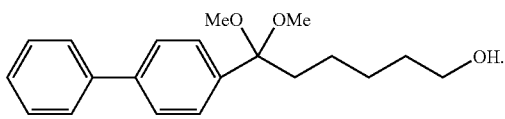

51. A compound according to claim 1, wherein said compound is selected from the following compounds, and pharmaceutically acceptable salts, amides, esters, and ethers thereof:

(ABD-150)
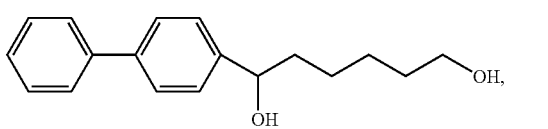

(ABD-177)
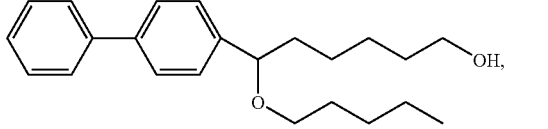

(ABD-182)

(ABD-195)
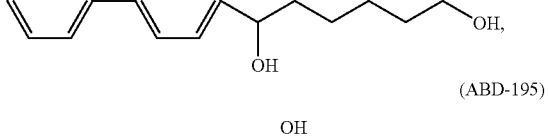

(ABD-235)
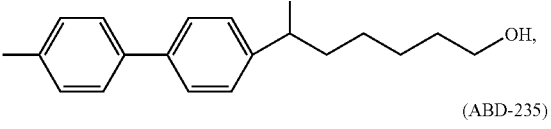

(ABD-236)
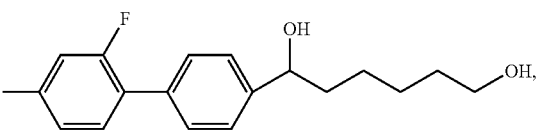

52. A composition comprising a compound according to claim 1 and a pharmaceutically acceptable carrier or diluent.

\* \* \* \* \*